(12) United States Patent
Chang et al.

(10) Patent No.: US 8,716,491 B2
(45) Date of Patent: May 6, 2014

(54) BENZIMIDAZOLIUM DYES AND THEIR USE AS FLUORESCENT CHEMOSENSORS

(75) Inventors: Young-Tae Chang, New York, NY (US); Shenliang Wang, New York, NY (US)

(73) Assignee: New York University, New York, NY (US)

( * ) Notice: Subject to any disclaimer, the term of this patent is extended or adjusted under 35 U.S.C. 154(b) by 1219 days.

(21) Appl. No.: 11/779,630

(22) Filed: Jul. 18, 2007

(65) Prior Publication Data
US 2008/0160521 A1    Jul. 3, 2008

Related U.S. Application Data

(60) Provisional application No. 60/807,642, filed on Jul. 18, 2006.

(51) Int. Cl.
*C07D 235/04* (2006.01)
*C07D 235/16* (2006.01)
*C07D 403/06* (2006.01)

(52) U.S. Cl.
USPC .............. 548/309.7; 548/305.1; 436/172

(58) Field of Classification Search
USPC ........................................ 548/309.7
See application file for complete search history.

(56) References Cited

U.S. PATENT DOCUMENTS

| | | |
|---|---|---|
| 2005/0054006 A1 | 3/2005 | Chang et al. |
| 2005/0227293 A1 | 10/2005 | Chang |
| 2008/0064037 A1 | 3/2008 | Chang et al. |

OTHER PUBLICATIONS

Gao et al., "Modified DNA Analogues that Sense Light Exposure with Color Changes," J. Am. Chem. Soc. 126 (40):12748-9 (2004).
Kim et al., "A Fluorescent Cavitand for the Recognition of GTP," Tetrahedron Letters 46:6617-20 (2005).
Kwon et al., "Fluorescent GTP-Sensing in Aqueous Solution of Physiological pH," J. Am. Chem. Soc. 126(29):8892-3 (2004).
Li et al., "Solid-Phase Synthesis of Styryl Dyes and Their Application as Amyloid Sensors," Angew. Chem. Int. Ed. 43:6331-5 (2004).
McCleskey et al., "Differential Receptors Create Patterns Diagnostic for ATP and GTP," 125(5):1114-5 (2003).
Rosania et al., "Combinatorial Approach to Organelle-Targeted Fluorescent Library Based on the Styryl Scaffold," J. Am. Chem. Soc. 125(5):1130-1 (2003).
Sauceda et al., "Designing Fluorescent Sensors of Heparin," ChemBioChem 8:391-4 (2007).
Wang et al., "Combinatorial Synthesis of Benzimidazolium Dyes and Its Diversity Directed Application Toward GTP-Selective Fluorescent Chemosensors," J. Am. .Chem. Soc. 128(32):10380-1 (2006).
Wright et al., "A Functional Assay for Heparin in Serum Using a Designed Synthetic Receptor," Angew. Chem. Int. Ed. 44:5679-82 (2005).
Zhong et al., "A Colorimetric Sensing Ensemble for Heparin," J. Am, Chem. Soc. 124:9014-5 (2002).
Zhu et al., "Combinatorial Discovery of Novel Fluorescent Dyes Based on Dapoxyl," Tetrahedron Letters 43:5083-6 (2002).
Vurbanova et al., CA 107:217455, "Synthesis of new N-alkylammonium salts of 2-(alkoxy- and alkoxyhydroxystyryl) quinolines" Doklady Bolgarskoi Akademii Nauk 39(12):63-65 (1986) Abstract.

*Primary Examiner* — Laura L Stockton
(74) *Attorney, Agent, or Firm* — LeClairRyan, a Professional Corporation

(57) ABSTRACT

The present invention is directed toward benzimidazolium dye compounds of formula (I) as follows:

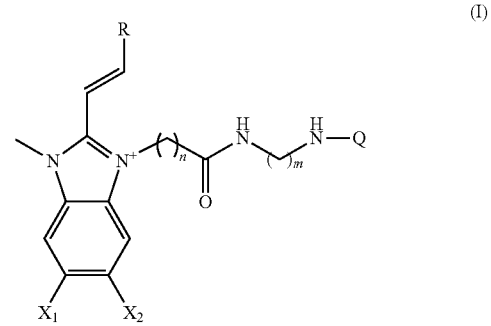

wherein,
n is an integer from 2-10,
m is an integer from 2-10,
$X_1$ and $X_2$ are independently a halogen,
Q is H or a resin, and
R is $(aromatic)_o$-$(linker)_p$-with the linker being saturated or unsaturated C1-C5 hydrocarbons, each aromatic independently being a substituted or unsubstituted aromatic or heteroaromatic, o being 1 or 2, and p being 0 or 1. Methods of making and using these compounds are also disclosed.

46 Claims, 46 Drawing Sheets

BENZIMIDAZOLIUM DYES AND THEIR USE AS FLUORESCENT CHEMOSENSORS

This application claims the benefit of U.S. Provisional Patent Application Ser. No. 60/807,642; filed Jul. 18, 2006.

The subject matter of this application was made with support from the United States Government under National Institute of Health, Grant No. P20GM072029. Components of this work were conducted in a Shared Instrumentation Facility constructed with support from Research Facilities Improvement Grant C06 RR-16572 from the NCRR/NIH. The U.S. Government has certain rights.

FIELD OF THE INVENTION

The present invention relates to benzimidazolium dye compounds and their use as fluorescent chemosensors.

BACKGROUND OF THE INVENTION

Fluorescent chemosensors are dye molecules whose fluorescence excitation/emission changes in response to the surrounding medium or through specific molecular recognition events. See *Molecular Fluorescence: Principles and Applications.*, Valeur, B.; Wiley-VCH: New York (2001). Due to their simplicity and high sensitivity, fluorescent sensors have been widely utilized as popular tools for chemical, biological, and medical applications. See *Molecular Fluorescence: Principles and Applications.*, Valeur, B.; Wiley-VCH: New York (2001); *Principles of Fluorescence Spectroscopy*, 2nd ed., Lakowicz, J. R., Kluwer Academic/Plenum: New York (1999); and *Fluorescent Chemosensors for Ion and Molecule Recognition*, Czarnik, A. W., American Chemical Society: Washington, DC (1993). The most general strategy for fluorescent sensor design is to combine fluorescent dye molecules with designed receptors for specific analytes, in hopes that the recognition event between receptor and analyte will lead to a fluorescence property change of the dye moiety. Although many fluorescent sensors have been successfully developed through this approach, each individual development requires a major effort in both the design and synthesis of the sensors. Also, the sensor's scope of application is limited to the selected specific analytes that the sensor was rationally designed for; these are so-called Analyte Directed Sensors. See Srinivasan, N., et al., *Curr. Opin. Chem. Biol.*, 8: 305 (2004); Rurack, K., et al., *Chem. Soc. Rev.*, 31, 116 (2002); Valeur, B., et al., *Coord. Chem. Rev.*, 205: 3 (2000); Martinez-Manez, R., et al., *Chem. Rev.*, 103: 4419 (2003); and de Silva, A. P., et al., *Chem. Rev.*, 97: 1515 (1997). Combinatorial dye library synthesis offers one of the most promising alternatives, once an efficient synthetic route can be developed for a diverse set of dyes. Sensors developed using this approach are called Diversity Directed Sensors. Combinatorial chemistry is now widely being used in the chemical biology and medicinal/pharmaceutical field for the discovery of biologically active molecules or drug candidates, yet the application of this method to fluorescent dyes is only in its infancy. See Li, Q., et al., *Angew. Chem. Int. Edit.*, 43: 6331 (2004); Gao, J., et al., *J. Am. Chem. Soc.*, 126: 12748 (2004); Rosania, G. R., et al., *J. Am. Chem. Soc.*, 125: 1130 (2003); and Zhu, Q., et al., *Tetrahedron Lett.*, 43: 5083 (2002).

Nucleotide anion detection has long intrigued researchers and witnessed continuous growth. See Li, C., et al., *Angew. Chem. Int. Edit.*, 44: 6371 (2005); Descalzo, A. B., et al., *J. Mater. Chem.*, 15: 2721 (2005); Mizukami, S., et al., *J. Am. Chem. Soc.*, 124: 3920 (2002); Ojida, A., et al., *Tetrahedron Lett.*, 43: 6193 (2002); Sancenon, F., et al., *Helv. Chim. Acta*, 85: 1505 (2002); Thanh, N., et al., *Anal Lett.*, 35: 2499 (2002); Turkewitsch, P., et al., *J. Photochem. Photobiol.*, 117: 199 (1998); Kim, S. K., et al., *Tetrahedron Lett.*, 46: 6617 (2005); Kwon, J. Y., et al., *J. Am. Chem. Soc.*, 126: 8892 (2004); McCleskey, S. C., et al., *J. Am. Chem. Soc.*, 125: 1114 (2003); and Amemiya, S., et al., *Chem. Commun.*, 1027 (1997). Although GTP plays an important role in biological processes, very little work has been done on the development of fluorescent sensors for it. See Kim, S. K., et al., *Tetrahedron Lett.*, 46: 6617 (2005); Kwon, J. Y., et al., *J. Am. Chem. Soc.*, 126: 8892 (2004); McCleskey, S. C., et al., *J. Am. Chem. Soc.*, 125: 1114 (2003); Amemiya, S., et al., *Chem. Commun.*, 1027 (1997); Burma, D. P., *J. Sci. Ind. Res.*, 47: 65 (1988); and Pogson, C. I., *Am. J. Clin. Nutr.*, 27: 380 (1974). Thus far, the best reported GTP sensor, which was designed rationally, showed around 90% quenching response at around mM concentration of GTP, and most of the known GTP sensors compete with ATP to some extent. See Kwon, J. Y., et al., *J. Am. Chem. Soc.*, 126: 8892 (2004). Currently, no turn-on fluorescent sensors for GTP have been reported yet.

Heparin is a naturally occurring polysaccharide which has been used as a major anticoagulant to prevent and treat thrombotic diseases since early 20th century. See Capila, I., et al., *Angew. Chem., Int. Ed.*, 41: 391 (2002); Whitelock, J. M., et al., *Chem. Rev.*, 105: 2745 (2005); and Rabenstein, D. L., *Nat. Prod. Rep.*, 19: 312 (2002). It is considered second only to insulin in the terms of being a very successful natural therapeutic agent. See Rabenstein, D. L., *Nat. Prod. Rep.*, 19: 312 (2002). Despite its long history and wide use, closely monitoring and control of the Heparin blood levels during the application of unfractionated heparin (UFH) and Low Molecular Weight Heparin (LMWH) is of crucial importance due to the risk of adverse effects such as hemorrhages and heparin-induced thrombocytopenia (HIT) resulting from overdoses. See Warkentin, T. E., et al., *New England Journal of Medicine*, 332: 1330-1335 (1995); Hoppensteadt, D., et al., *Hematology-Oncology Clinics of North America*, 17: 313 (2003); and Pineo, G. F., et al., *Medical Clinics of North America*, 82: 587 (1998). Various assays have been established to monitor the heparin concentration, including the most commonly used assays: activated partial thromboplastin time (aPTT), anti-Xa, and activated clotting time (ACT) assays. See Simko, R. J., et al., *Annals of Pharmacotherapy*, 29: 1015-1021 (1995); Murray, D. J., et al., *Journal of Cardiothoracic and Vascular Anesthesia*, 11: 24-28 (1997); and Marci, C. D., et al., *American Journal of Clinical Pathology*, 99:546-550 (1993). Although the evolution of methods for monitoring heparin has been improving through the decades, which method is the ideal remains controversial. See Kitchen, S., *British Journal of Haematology*, 111: 397-406 (2000); and Francis, J. L., et al., *Pharmacotherapy*, 24: 108-119 (2004).

Fluorescent chemosensors have witnessed a continuous progress together with the development of supermolecular chemistry and molecular recognition throughout the decades. See Lakowicz, J. R., Principles of Fluorescence Spectroscopy, 2nd ed., Kluwer Academic/Plenum: New York (1999); and Valeur, B., Molecular Fluorescence: Principles and Applications, Wiley-VCH: Weinheim; New York (2002). Various chemosensors have been developed and successfully utilized in diverse chemical, biological and medical applications. The properties of fluorescence, such as simplicity and high sensitivity, are highly appreciated. An important field for chemosensors is the targeting of bio-relevant analytes. The development of chemosensors for heparin assay was marked by the pioneering work of Anslyn's Group. See Zhong, Z. L., et al., *J. Am. Chem. Soc.*, 124: 9014 (2002); and Wright, A. T., et al., *Angewandte Chemie-International Edition*, 44: 5679-

5682 (2005). A tripodal boronic acid based small molecule with intramolecular boron-nitrogen interaction was designed and synthesized for heparin assay and was demonstrated as a fluorescence quenching sensor, which for the first time raised the question of fluorescent sensing heparin. Along these lines, a peptide based sensor was developed based on a heparin-specific peptide sequence AG73. See Sauceda, J. C., et al., *Chembiochem*, 8: 391-394 (2007). Chloride anion quenched fluorescence was regenerated when heparin introduced. However, these sensors were carefully designed for the specific purpose and, as previously noted, Analyte Directed Sensors. Combinatorial dye library synthesis offers one of the most promising alternatives as Diversity Directed Sensors, once an efficient synthetic route can be developed for a diverse set of dyes.

The present invention is directed to overcoming these and other deficiencies in the art.

SUMMARY OF THE INVENTION

One aspect of the present invention is directed toward a compound according to formula (I)

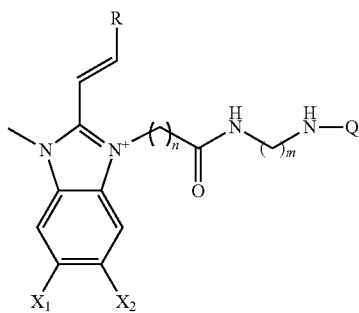

(I)

wherein, n is an integer from 2-10, m is an integer from 2-10, $X_1$ and $X_2$ are independently a halogen, Q is H or a resin, and R is (aromatic)$_o$-(linker)$_p$-with the linker being saturated or unsaturated C1-C5 hydrocarbons, each aromatic independently being a substituted or unsubstituted aromatic or heteroaromatic, o being 1 or 2, and p being 0 or 1.

Another aspect of the present invention is directed toward a method of detecting the presence of GTP in a sample. The method includes introducing a compound of formula (I), as described above, into a sample, where the compound does not fluoresce in the absence of a threshold amount of GTP. The sample is then exposed to light at a wavelength suitable to induce fluorescent emissions by the compound and fluorescent emissions are detected by the compound, where fluorescence indicates the presence of the threshold amount of GTP.

A further aspect of the present invention is directed toward a method of detecting the presence of heparin in a sample. The method includes introducing a compound of formula (I), as described above, into a sample, where the compound does not fluoresce in the absence of a threshold amount of heparin. The sample is then exposed to light at a wavelength suitable to induce fluorescent emissions by the compound. Fluorescent emissions by the compound are detected, where fluorescence indicates the presence of heparin.

A further aspect of the present invention is directed toward a method of making a compound of formula (I) where Q is H. The method includes treating the compound of formula (I) wherein Q is a resin under conditions effective to cleave the resin.

A still further aspect of the present invention is directed toward a method of making a compound of formula (I). The method includes reacting a compound according to formula (II)

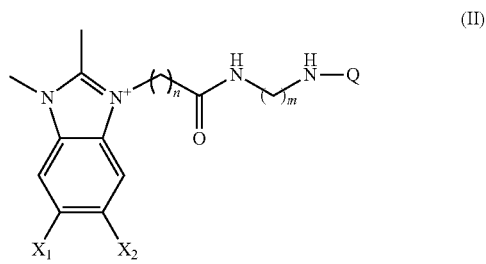

(II)

with R—(CO)H under conditions effective to form the compound of formula (I).

DETAILED DESCRIPTION OF THE INVENTION

Figure 1:
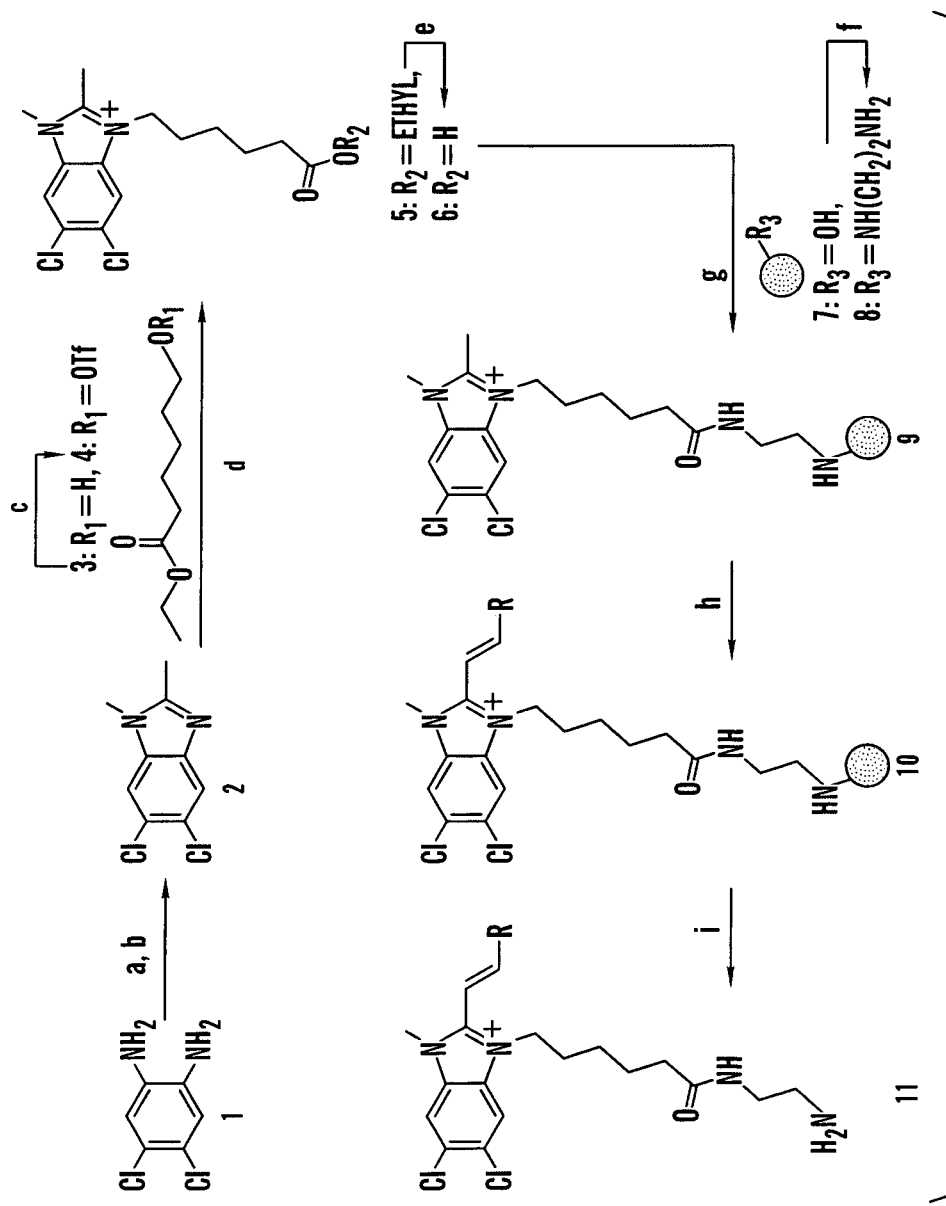
FIG. 1 is a reaction scheme illustrating the synthesis of benzimidazolium hemicyanine dyes. (a) is triethyl orthoacetate, H$^+$, toluene, reflux; (b) is KOH, MeI, acetone; (c) is Tf$_2$O, poly(4-vinylpyridine), DCM; (d) is 4, DCM; (e) is 48% HBr, 65° C.; (f) is 2-chlorotrityl alcohol resin sequentially treated with thionyl chloride in DCM and ethylene diamine in DCM; (g) is 8, O-(7-Azabenzotriazole-1-yl)-N,N,N',N'-tetramethyluronium hexafluorophosphate (HATU), diisopropylamine (DIPEA), 30% N, N-dimethylformamide/dichloromethane (DMF/DCM); (h) is R-CHO (96-aromatic aldehydes, see FIG. 2), pyrrolidine, NMP; and (i) is 5% TFA/DCM.

One aspect of the present invention is directed toward a compound according to formula (I)

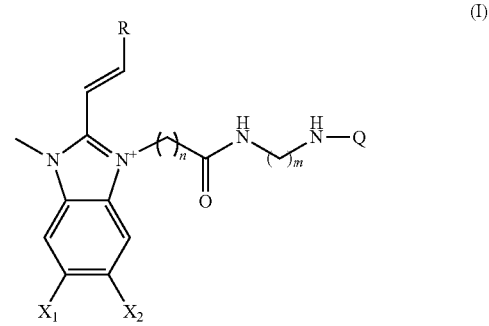

(I)

wherein, n is an integer from 2 -10, m is an integer from 2-10, $X_1$ and $X_2$ are independently a halogen, Q is H or a resin, and R is (aromatic)$_o$-(linker)$_p$-with the linker being saturated or unsaturated C1-C5 hydrocarbons, each aromatic independently being a substituted or unsubstituted aromatic or heteroaromatic, o being 1 or 2, and p being 0 or 1.

In preferred embodiments, the halogen may be F, Cl, Br, or I. Preferably n is an integer from 3 to 8, most preferably, n is 5. In another preferred embodiments, m is an integer from 2 to 5, most preferably, m is 2. In certain embodiments, Q is H, p is 0, and the aromatic is a heteroaromatic ring.

In certain embodiments, the hetero atom in the heteroaromatic ring is an N, S, or O hetero atom or the heteroaromatic ring may be substituted. The substituent can comprise one or more of hydroxy, saturated or monounsaturated hydrocarbon, (halo)alkoxy, haloalkyl, dihaloalkyl, trihaloalkyl, amine, alkylamine, dialkylamine, nitro, halo, or cyano groups. In certain embodiments, the heteroaromatic ring is a multi-ring or fused ring.

In some embodiments, the aromatic is an aromatic ring which does not include a hetero atom. The aromatic ring may be substituted and the substituent may comprise one or more of hydroxy, saturated or monounsaturated hydrocarbon, (halo)alkoxy, haloalkyl, dihaloalkyl, trihaloalkyl, amine, alkylamine, dialkylamine, nitro, halo, or cyano groups. Also, the aromatic ring may be a multi-ring or fused ring.

In certain embodiments, the R group may be any of the following groups from Table 1 (below) and the bond with the crossing dashed line may illustrate the bond formed joining R to the molecule of formula (I). A molecule of formula (I) containing an R group from Table 1 (below) will be refered to as molecule "G#" where # is the number of the R group from Table 1. See Table 1.

TABLE 1

Benzimidazolium dye library member list.

| Compound Code | Purity (%)† | $\lambda_{ex}$ (nm)‡ | $\lambda_{em}$ (nm)‡ |
|---|---|---|---|
| G1 | 99.2 | 460 | 580 |
| G2 | 96.4 | 390 | 470 |
| G3 | 94.2 | 370 | 470 |
| G4 | 96.3 | 390 | 490 |
| G5 | 98.7 | 360 | 560 |
| G6 | 98.5 | 360 | 560 |
| G7 | 98.6 | 420 | 490 |
| G8 | 98.8 | 410 | 480 |
| G9 | 92.1 | 420 | 560 |
| G10 | 97.4 | 450 | 540 |
| G11 | 93.5 | 420 | 520 |
| G12 | 98.9 | 450 | 550 |
| G13 | 97.6 | 450 | 600 |
| G14 | 94.5 | 390 | 490 |
| G15 | 92.3 | 390 | 490 |
| G16 | 92.9 | 430 | 540 |
| G17 | 96.3 | 390 | 500 |
| G18 | 96.8 | 370 | 460 |
| G19 | 91.1 | 360 | 450 |
| G20 | 97.6 | 360 | 440 |
| G21 | 98.0 | 380 | 470 |
| G22 | 97.6 | 390 | 480 |
| G23 | 97.8 | 420 | 530 |
| G24 | 92.0 | 460 | 540 |
| G25 | 95.4 | 450 | 600 |
| G26 | 97.1 | 390 | 540 |
| G27 | 95.6 | 460 | 550 |
| G28 | 98.7 | 380 | 470 |
| G29 | 95.0 | 380 | 560 |
| G30 | 97.1 | 390 | 480 |
| G31 | 90.5 | 380 | 430 |
| G32 | 96.8 | 450 | 520 |
| G33 | 98.2 | 450 | 540 |
| G34 | 98.7 | 380 | 450 |
| G35 | 95.5 | 450 | 560 |
| G36 | 95.1 | 360 | 460 |
| G37 | 96.5 | 460 | 520 |
| G38 | 80.3 | 360 | 510 |
| G39 | 97.3 | 430 | 480 |
| G40 | 99.7 | 400 | 520 |
| G41 | 98.4 | 380 | 490 |
| G42 | 95.8 | 420 | 490 |
| G43 | 98.7 | 400 | 490 |
| G44 | 98.5 | 390 | 480 |
| G45 | 98.7 | 410 | 470 |

TABLE 1-continued

Benzimidazolium dye library member list.

| Compound Code | Purity (%)† | $\lambda_{ex}$ (nm)‡ | $\lambda_{em}$ (nm)‡ |
|---|---|---|---|
| G46 | 99.2 | 380 | 440 |
| G47 | 99.7 | 380 | 470 |
| G48 | 98.0 | 430 | 530 |
| G49 | 96.5 | 450 | 520 |
| G50 | 92.6 | 370 | 450 |
| G51 | 96.4 | 360 | 550 |
| G52 | 99.4 | 410 | 470 |
| G53 | 98.9 | 380 | 520 |
| G54 | 96.2 | 380 | 640 |
| G55 | 99.6 | 370 | 440 |
| G56 | 98.6 | 370 | 440 |
| G57 | 98.0 | 400 | 520 |
| G58 | 98.4 | 360 | 470 |
| G59 | 97.6 | 450 | 540 |
| G60 | 96.0 | 430 | 490 |
| G61 | 97.5 | 400 | 510 |
| G62 | 94.0 | 460 | 550 |
| G63 | 74.3 | 490 | 620 |
| G64 | 97.8 | 460 | 560 |
| G65 | 94.6 | 460 | 560 |
| G66 | 97.2 | 450 | 650 |
| G67 | 98.1 | 460 | 550 |
| G68 | 97.1 | 350 | 460 |
| G69 | 96.3 | 460 | 560 |
| G70 | 92.0 | 380 | 560 |
| G71 | 90.6 | 460 | 560 |
| G72 | 99.4 | 380 | 560 |
| G73 | 93.7 | 380 | 460 |
| G74 | 98.0 | 410 | 500 |
| G75 | 99.0 | 380 | 630 |
| G76 | 95.4 | 390 | 470 |
| G77 | 95.5 | 400 | 560 |
| G78 | 98.7 | 430 | 520 |
| G79 | 93.7 | 420 | 470 |
| G80 | 97.4 | 400 | 490 |
| G81 | 99.0 | 490 | 530 |
| G82 | 99.6 | 430 | 490 |
| G83 | 98.3 | 350 | 460 |
| G84 | 95.4 | 420 | 500 |
| G85 | 98.1 | 390 | 500 |
| G86 | 96.0 | 450 | 510 |
| G87 | 99.4 | 380 | 470 |
| G88 | 99.6 | 380 | 480 |
| G89 | 95.8 | 380 | 540 |
| G90 | 99.0 | 410 | 510 |
| G91 | 98.7 | 380 | 470 |
| G92 | 95.8 | 450 | 550 |
| G93 | 99.1 | 380 | 440 |
| G94 | 98.5 | 390 | 480 |
| G95 | 93.4 | 360 | 440 |
| G96 | 98.1 | 420 | 500 |

†Products were collected without further purification. Purity of each product was calculated based on LC-MS 350 nm trace area sizes.
‡All fluorescence excitation and emission data were recorded on a Gemini XS fluorescent plate reader with 1 mM compounds in methanol (100 µL) in Grainer 96 well black polypropylene plates.

In certain embodiments, the R group may be

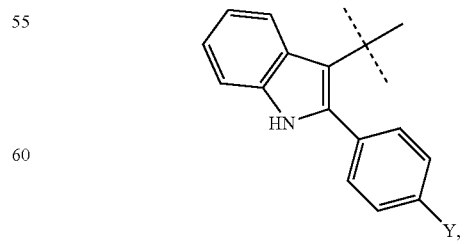

Y is H or halogen, and the bond with the crossing dashed line illustrates the bond formed joining R to the molecule of formula (I). Or the Y group is a halogen (i.e. F, Cl, Br, or I).

In certain embodiments, the R group may be

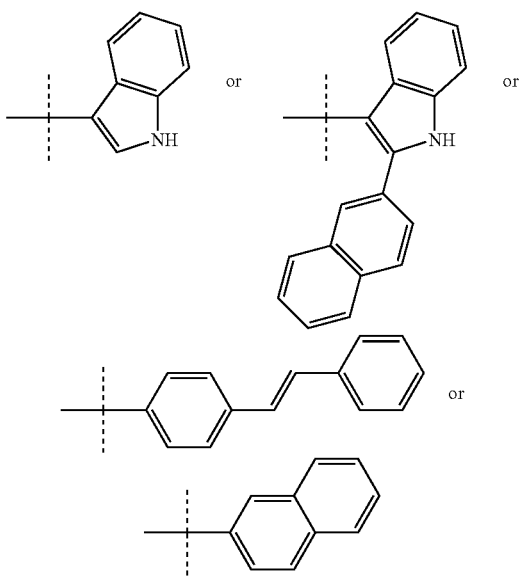

and the bond with the crossing dashed line may illustrate the bond formed joining R to the molecule of formula (I).

Another aspect of the present invention is directed toward a method of detecting the presence of GTP in a sample. The method includes introducing a compound of formula (I), as described above, into a sample, where the compound does not fluoresce in the absence of a threshold amount of GTP. The sample is then exposed to light at a wavelength suitable to induce fluorescent emissions by the compound and fluorescent emissions are detected by the compound, where fluorescence indicates the presence of the threshold amount of GTP.

In certain embodiments the threshold amount is about $2 \times 10^{-5}$ M GTP. The compound produces substantially no fluorescent emissions in the presence of adenosine, uridine, cytosine, guanosine, AMP, ADP, ATP, UMP, UDP, UTP, CMP, CDP, CTP, GMP, or GDP.

The sample may comprise a cell extract or whole cells. The whole cells may be present in an ex vivo tissue sample or in an in vitro cell sample.

Assuming the cationic hemicyanine dye is a potential receptor of nucleotides due to electrostatic interactions, the benzimidazolium motif was chosen as the library scaffold of the fluorescent sensors. Condensation of benzimidazolium ring with 96 aromatic aldehydes provides extended conjugation and structural diversity. To achieve longer wavelengths of the final fluorophore, which may be more useful for possible biological application, two Cl groups were introduced to the benzimidazolium ring (green-red range of emission) rather than using an unsubstituted benzimidazolium ring (UV-blue range of emission). It is noteworthy that the diversity elements (from aldehydes) constitute part of the conjugation system of the dye products, and will also serve as recognition motifs for analyte binding. Without linking two separate motifs as in common analyte directed sensors, these diversity directed sensors can be smaller in size and may respond more directly to their conformational change upon analyte binding.

To facilitate the synthetic procedure, securing high purity compounds without further purification, a novel solid phase synthesis pathway was developed for the benzimidazolium library. The optimized synthetic procedure is described in Examples 2 through 9 and shown in FIG. 1. The benzimidazolium scaffold with linker was prepared in solution phase and loaded onto ethylene diamine derivatized 2-chlorotrityl polystyrene solid support. Various lengths of the linker were tested and optimized for best loading of the benzimidazolium compound onto the resin.

Aromatic aldehyde building blocks were then coupled to benzimidazolium ring on solid support and final products were collected by acidic cleavage. The purity of the 96 compounds was very high (average purity of 96.4% without further purification) and due to the structural diversity, various excitation/emission wavelengths were observed.

Figure 2A:
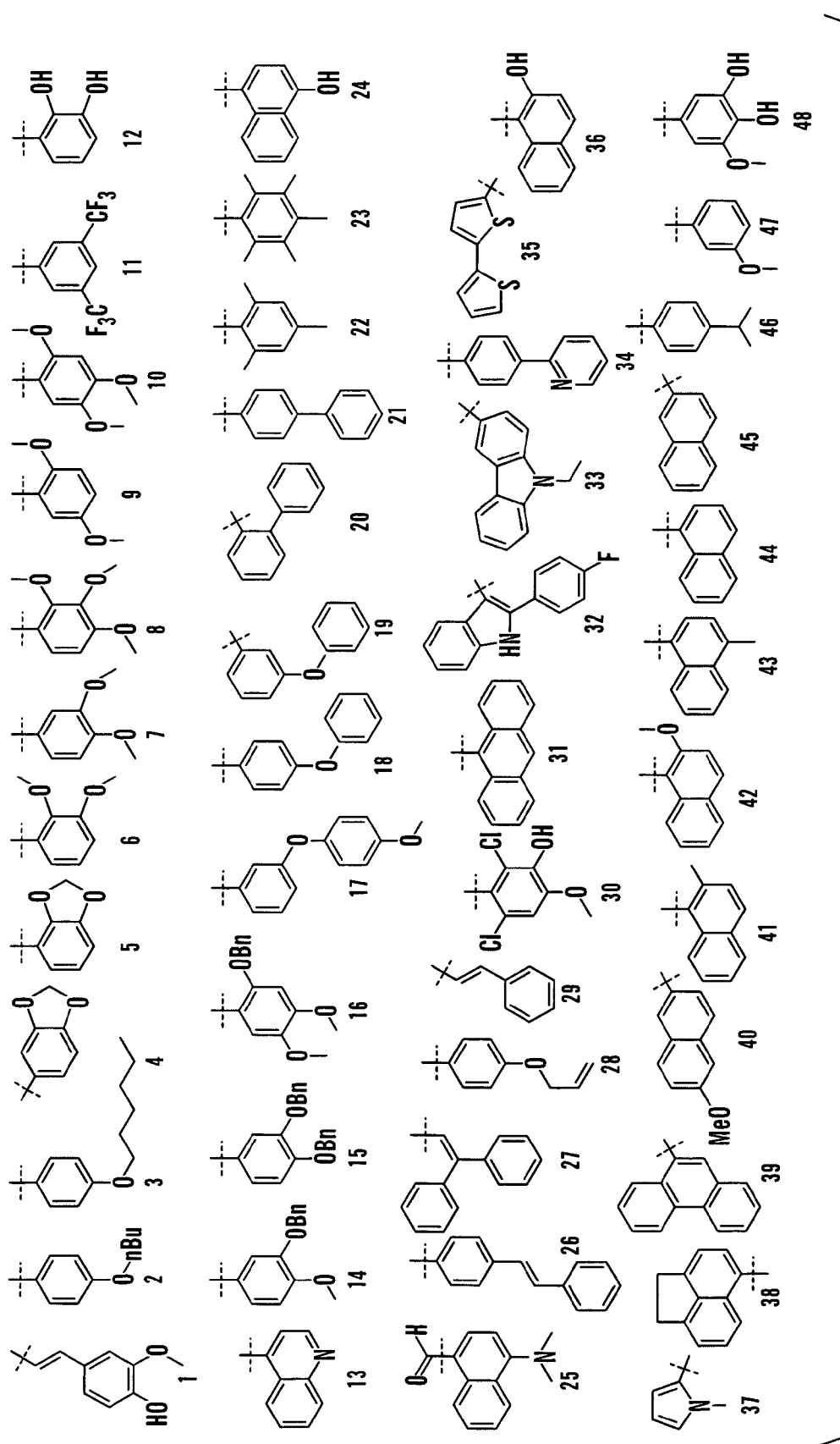
FIG. 2 shows structural formulae for the R group aldehyde building blocks for benzimidazolium dye library. The bond with the crossing dashed line illustrates the bond formed joining R to CHO in the aldehyde formula R—CHO.
Figure 2B:
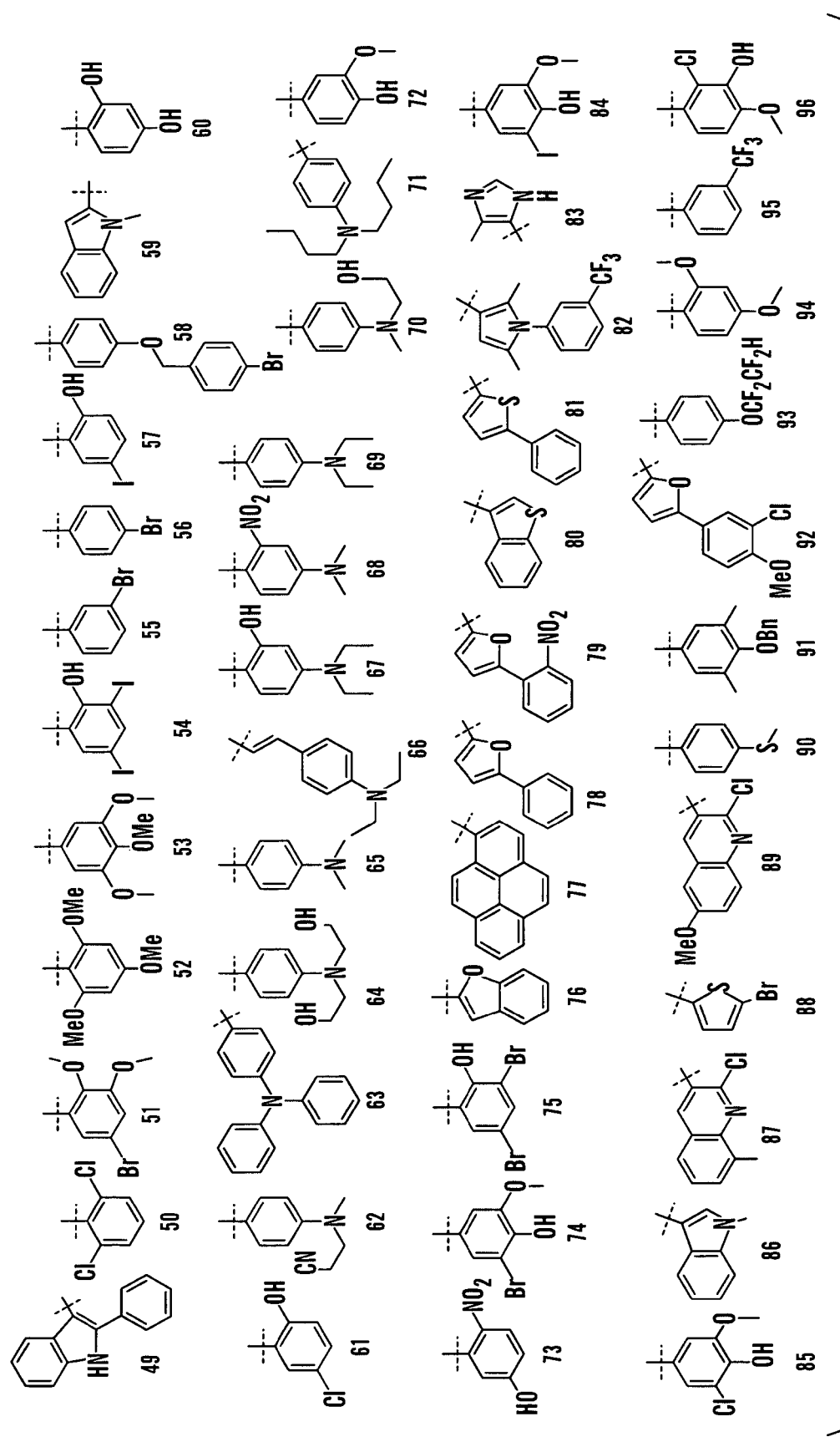

For a primary screening, the synthesized dye compounds were tested for AMP, ADP, ATP, UTP, CTP, and GTP in 384-well microplates using a fluorescence plate reader. Two structurally related compounds (G32 and G49, see FIG. 2) showed dramatically increased fluorescence upon addition of GTP, while not responding to other nucleotides.

A further aspect of the present invention is directed toward a method of detecting the presence of heparin in a sample. The method includes introducing a compound of formula (I), as described above, into a sample, where the compound does not fluoresce in the absence of a threshold amount of heparin. The sample is then exposed to light at a wavelength suitable to induce fluorescent emissions by the compound. Fluorescent emissions by the compound are detected, where fluorescence indicates the presence of heparin.

In certain embodiments, the fluorescence may indicate the presence of the threshold amount of heparin. The threshold amount is about 0.1 μM. In certain embodiments, the detecting is quantitative.

In certain embodiments the sample may comprise blood plasma and the heparin may be unfractionated heparin or low molecular weight heparin.

A further aspect of the present invention is directed toward a method of making a compound of formula (I) where Q is H. The method includes treating the compound of formula (I) wherein Q is a resin under conditions effective to cleave the resin. For example, a compound of formula (I) wherein Q is a resin can be cleaved from the resin by suspending the compound in a 5% trifluoroacetic acid/dichloromathane cleavage cocktail. The resin is then filtered off and washed in dichloromethane and methanol. The solutions are combined and evaporated to obtain the compound.

A still further aspect of the present invention is directed toward a method of making a compound of formula (I). The method includes reacting a compound according to formula (II)

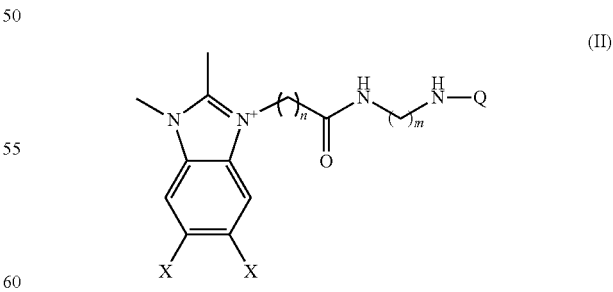

(II)

with R—(CO)H under conditions effective to form the compound of formula (I). Each aldehyde (see FIG. 2) in a 1-methyl-2-pyrrolidinone solution is reacted in pyrrolidine with a compound according to formula (II). The mixture is shaken in the dark and under a positive pressure of nitrogen for 24 hrs. Then the resin is filtered and washed with N, N-dimethylformamide (DMF), alternatively dichloromethane (DCM) and methanol, dichloromethane and dried in vacuum.

In certain embodiments the method includes reacting a resin-bound (aminoalkyl)amine with an intermediate carboxylic acid according to formula (III)

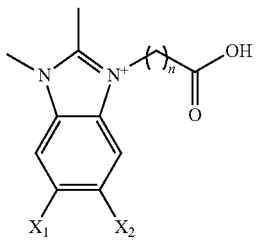

(III)

under conditions effective to form the compound according to formula (II). 1-(5-carboxypentyl)- 5,6-dichloro- 2,3-dimethyl-benzoimidazo hum bromide (6) is reacted with diisopropylamine (DIPEA) and O-(7-Azabenzotriazole-1-yl)-N, N, N', N'-tetramethyluronium hexafluorophosphate (HATU) in dichloromethane and DMF and shaken at room temperature. Resin bound 2-amino-ethylamine is added to this solution and shaken at room temperature overnight. The resin is then filtered and washed with dichloromethane and methanol alternatively and dried in vacuum.

In certain embodiments, the method includes reacting ethyl 6-(trifluoromethylsulfonyloxy)alkanoate with 5,6-dihalo-1,2-dimethyl-benzoimidazole under conditions effective to form the compound according to formula (III). 5,6-dichloro-1,2-dimethyl-benzoimidazole (2) is reacted with ethyl 6-(trifluoromethylsulfonyloxy)hexanoate (4) in dichloromethane and stirred in dark for 24 hrs at room temperature. The solvent was evaporated under reduced pressure and the residue was recrystalized from MeOH/diethyl ether.

As a further demonstration of the disclosed method, herein is communicated the development of the first ratio-metric and turn-on fluorescent chemosensors for heparin assay via high-throughput screening of a combinatorial library, from which a fluorescent chemosensor for GTP was discovered. See Wang, S. L., et al., *Journal of the American Chemical Society*, 128: 10380-10381 (2006), which is hereby incorporated by reference in its entirety.

Figure 3B:
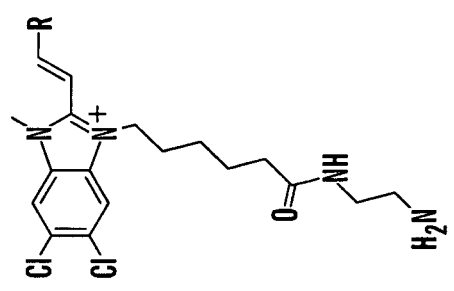
FIGS. 3A-B show (A) the structure of the repeating unit of heparin and (B) the benzimidazolium dye library general scaffold structure.
Figure 3A:
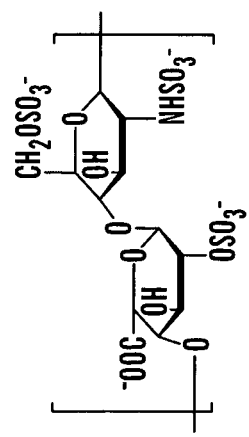

Heparin is a linear, highly-sulfated glycosaminoglycan mixture and is known as the natural macromolecule with the highest negative charge density. See Whitelock, J. M., et al., *Chem. Rev.*, 105: 2745 (2005), which is hereby incorporated by reference in its entirety. Both unfractionated heparin (UFH) and Low Molecular Weight Heparin (LMWH) are largely accounted for by repeating sequences of the trisulfated disaccharide L-iduronic acid and D-glucosamine (see FIG. 3A), with UFH of an average molecular weight of 15000 (range 15 to 100 monosaccharides) and LMWH of molecular weights between 4000 and 6500 (range 4 to 40 monosaccharides). Due to the complexity of heparin, the average of monosaccharide molecular weight (half of the repeating unit molecular weight) was used as the molecular weight of heparin. Assuming the cationic hemicyanine dye is a potential receptor of heparin due to electrostatic interactions, a benzimidazolium dye library was used for the screening. See FIG. 3B.

EXAMPLES

Example 1

Materials

Chemicals and solvents were purchased from Sigma-Aldrich or Acros and used without further purification. 2-Chlorotrityl alcohol resin (1.37 mmol/g) was purchased from BeadTech Inc., Korea. Compounds were tested with LC-MSD (ChemStation 1100, Agilent Technologies.) equipped with a Phenomenex Luna 3 µC18 column (20×4.0 mm). $^1$H-NMR and $^{13}$C-NMR spectra were obtained on a Bruker Avance 400 NMR spectrometer and were recorded at 400 and 100 MHz, respectively. Chemical shifts are reported relative to internal chloroform ($^1$H δ 7.26 ppm, $^{13}$C δ 77.0 ppm) or dimethyl sulfoxide ($^1$H δ 2.50 ppm, $^{13}$C δ 39.43 ppm). All analytes were purchased from Sigma with the highest purity available. Nonlinear fits were performed by GraphPad Prism 4 (GraphPad Software, Inc.) with variable slope sigmoidal dose-response equation:

$$Y = \text{Bottom} + \frac{(\text{Top} - \text{Bottom})}{1 + 10^{\log EC_{50} - X} \times HillSlope}$$

Example 2

5,6-Dichloro-1,2-Dimethyl-Benzoimidazole (2)

Figure 9:
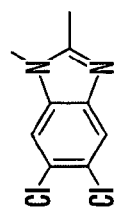
FIG. 9 shows the structural formula of 5,6-dichloro-1,2-dimethyl-benzoimidazole (2).

Triethyl orthoacetate (4.6 g, 1 eq) was added drop wise to a refluxing mixture of 4,5-dichloro-1,2-phenylenediamine (5 g, 1 eq) and a catalytic amount of p-toluenesulfonic acid in toluene (40 mL). The mixture was refluxed for 3 hrs and 5.7 g black solid was collected after evaporation of the solvents under reduced pressure and used directly in the following step without further purification. ESI-MS (m/z) calcd (found): 200.0 (201.1) for [M+H]$^+$. To the crude 5,6-dichloro-2-methyl-benzoimidazole (5.7 g, 1 eq) (see FIG. 9) and grinded potassium hydroxide (4.8 g, 3 eq) in acetone (50 mL) was added iodomethane (5.2 g, 1.4 eq) drop wise and the mixture was stirred overnight. The solvent was evaporated under reduced pressure and the residue was partitioned between dichloromethane (200 mL) and water (200 mL). The aqueous phase was washed two times with dichloromethane (200 mL) and the combined organic phase was dried over Na$_2$SO$_4$ and evaporated to dryness. The crude product was recrystallized from ethyl acetate. 5.5 g product was collected as pale flakes with 90.6% yield for two steps. $^1$H NMR: (CDCl$_3$) 2.55 (s, 3H), 3.63 (s, 3H), 7.28 (s, 1H), 7.68 (s, 1H). $^{13}$C NMR: (CDCl$_3$): 13.82, 30.05, 110.20, 120.00, 125.58, 125.75, 134.97, 141.83, 153.93. ESI-MS (m/z) calcd (found): 214.0 (215.1) for [M+H]$^+$.

Example 3

Ethyl 6-(Trifluoromethylsulfonyloxy)Hexanoate (4)

Figure 10:
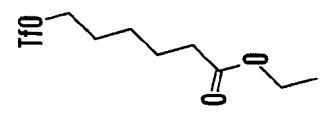
FIG. 10 shows the structural formula of ethyl 6-(trifluoromethylsulfonyloxy)hexanoate (4).

To the suspension of poly(4-methylpyridine) (2.24 g, 2 eq) in newly dried dichloromethane (25 mL) at 0° C. was added trifluoromethanesulfonic anhydride (5 g, 1 eq) drop wise over 30 mins. Ethyl 6-hydroxyhexanoate (2.76 g, 0.95 eq) was then added in drop wise via a syringe. The mixture was stirred at 0° C. for 4 hrs and the polymer was filtered off by a frit. The solvent was evaporated under reduced pressure (without heating) and the crude product was subjected to a short silica gel pad with 1:4 (v/v) diethyl ether/hexane as the eluent solvent. The solvent was evaporated (without heating) and the product was used directly in the following step. (3.9 g, 75% yield based on ethyl 6-hydroxyhexanoate.) See FIG. 10.

Example 4

5,6-Dichloro-1-(6-Ethoxy-6-Oxohexyl)-2,3-Dimethyl-Benzoimidazolium Trifluoromethane-sulfonate (5)

Figure 11:
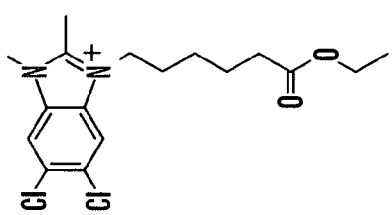
FIG. 11 shows the structural formula of 5,6-dichloro-1-(6-ethoxy-6-oxohexyl)-2,3-dimethyl-benzoimidazolium trifluoromethanesulfonate (5).

To 2 (2 g, 1 eq) in 10 mL dichloromethane was added 4 (2.8 g, 1 eq) and stirred in dark for 24 hrs at room temperature. Solvent was evaporated under reduced pressure and the residue was recrystalized from MeOH/diethyl ether to get the white powder as product (4.1 g, 87% yield.) See FIG. 11. $^1$H NMR: (DMSO) 1.16 (t, 3H), 1.37 (m, 2H), 1.57 (m, 2H), 1.75 (m, 2H), 2.28 (t, 2H), 2.88 (s, 3H), 3.96 (s, 3H), 4.04 (q, 2H), 4.46 (t, 2H), 8.48 (s, 1H), 8.52 (s, 1H). $^{13}$C NMR: (DMSO): 10.61, 13.98, 23.90, 25.04, 28.11, 31.98, 33.20, 45.09, 59.58, 114.73, 114.78, 128.76, 128.79, 130.06, 130.91, 154.24, 172.63. ESI-MS (m/z) calcd (found): 357.1 (357.3) for [M]$^+$.

Example 5

1-(5-Carboxypentyl)-5,6-Dichloro-2,3-Dimethyl-Benzoimidazolium Bromide (6)

Figure 12:
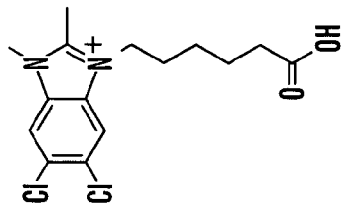
FIG. 12 shows the structural formula of 1-(5-carboxypentyl)-5,6-dichloro-2,3-dimethyl-benzoimidazolium bromide (6).

5 (4 g) was dissolved in 48% HBr aqueous solution (5 mL) and heated at 65° C. for 2 hrs and then evaporated to dryness. The residue was recrystalized from acetone to yield 2.5 g white crystal, yield 77%. See FIG. 12. $^1$H NMR: (DMSO) 1.36 (m, 2H), 1.54 (m, 2H), 1.74 (m, 2H), 2.21 (t, 2H), 2.87 (s, 3H), 3.95 (s, 3H), 4.46 (t, 2H), 8.49 (s, 1H), 8.54 (s, 1H). $^{13}$C NMR: (DMSO): 10.75, 23.92, 25.14, 28.19, 32.08, 33.37, 45.13, 114.78, 114.82, 128.73, 128.76, 130.04, 130.91, 154.26, 174.20. ESI-MS (m/z) calcd (found): 329.1 (329.1) for [M]$^+$.

Example 6

Resin Bound 2-Amino-Ethylamine (8)

Figure 13:
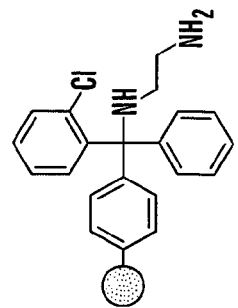
FIG. 13 shows the structural formula of resin bound 2-amino-ethylamine (8).
Figure 16A:
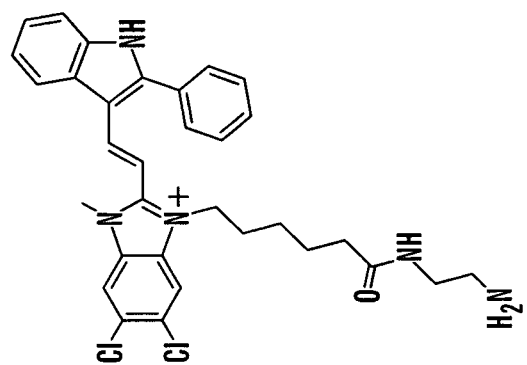
FIGS. 16A-C show the (A) structural formula; (B) LC-MS spectrum; and (C) ESI-MS (m/z) calcd (found): 574.2 (574.4) for [M]$^+$ of G49.
Figure 16B:
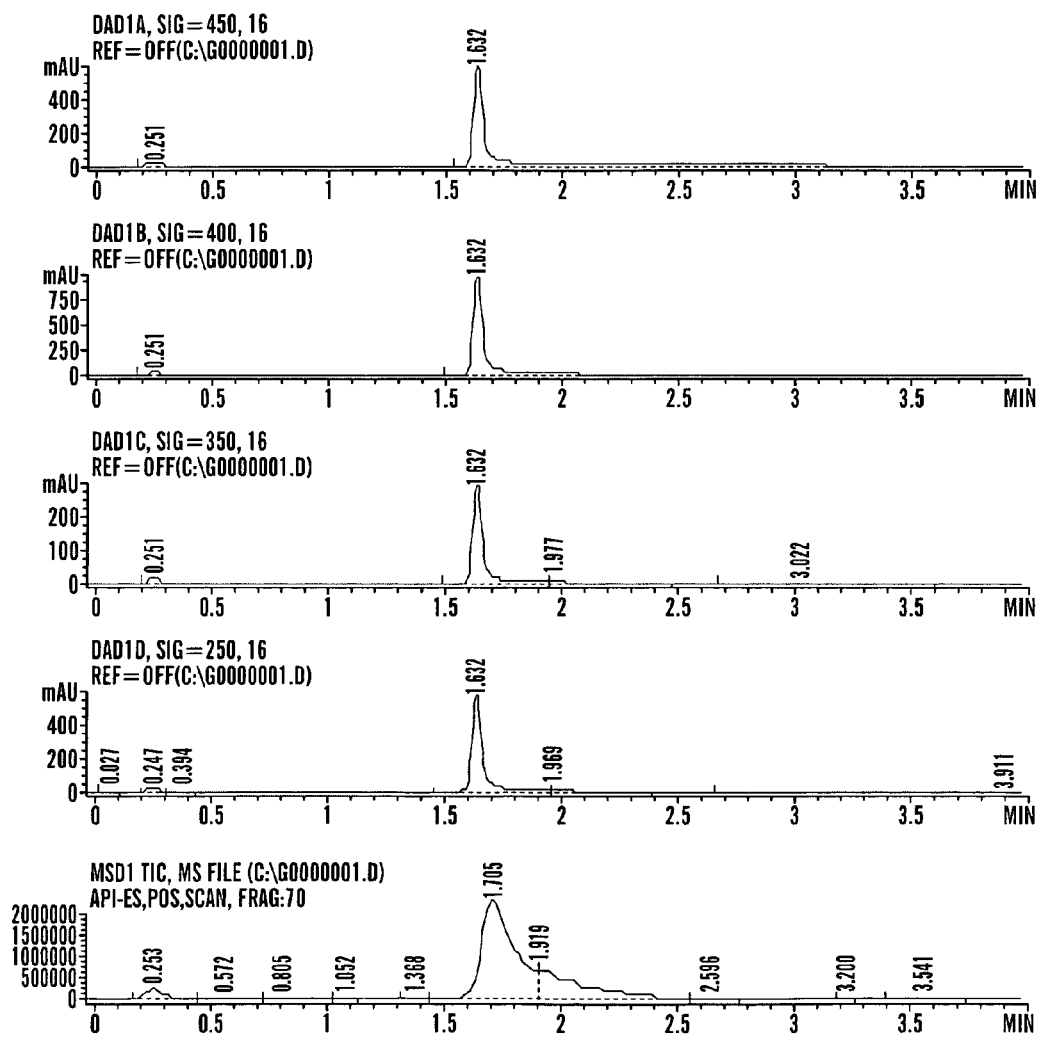
Figure 16C:
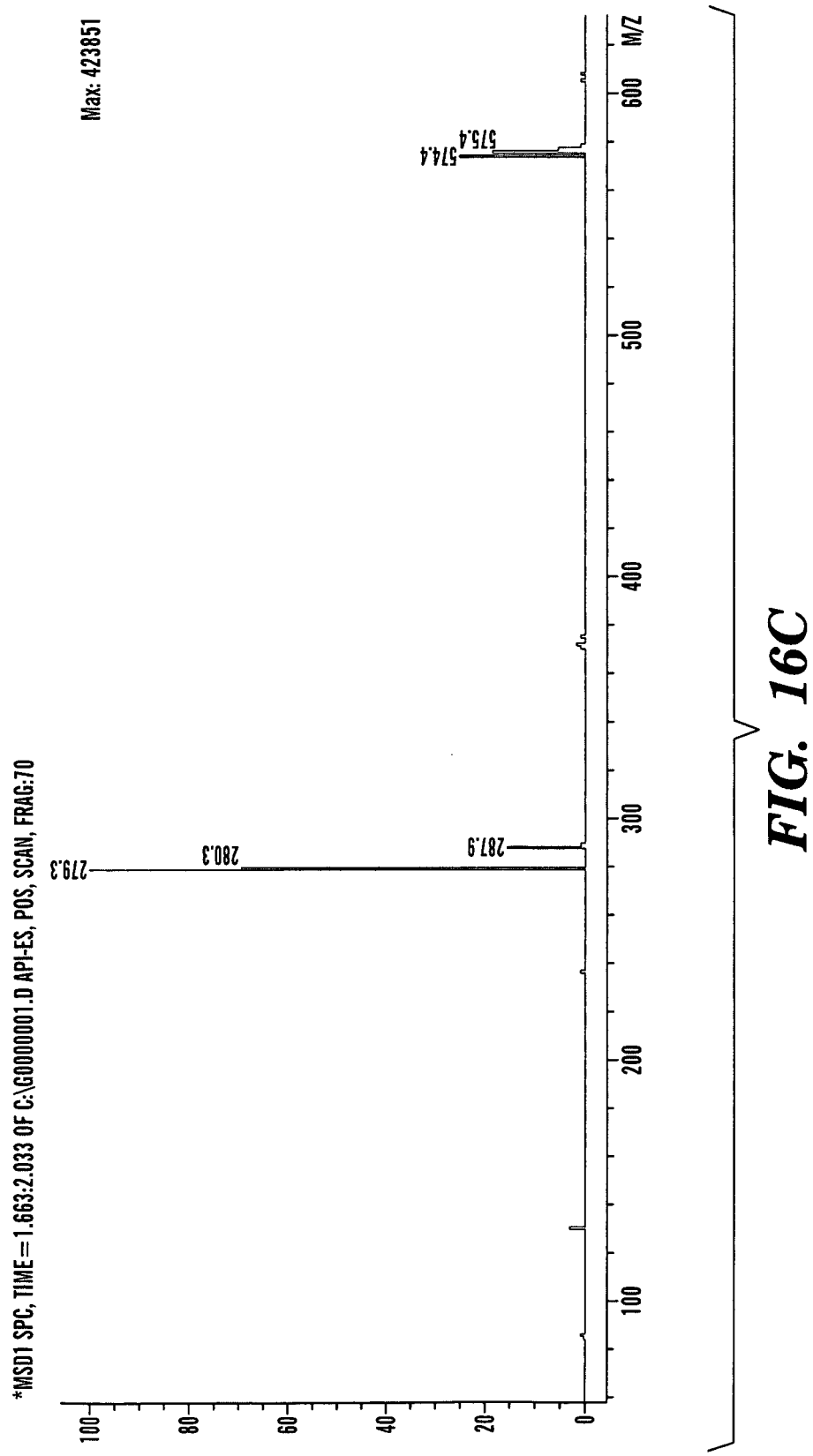
Figure 17A:
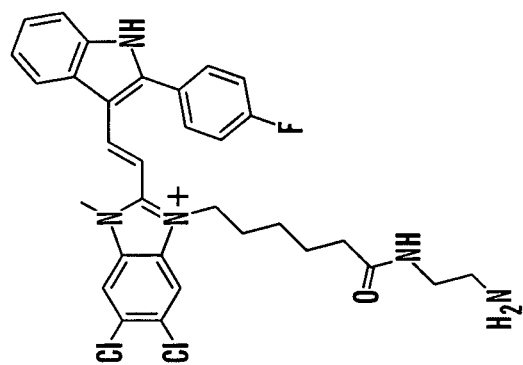
FIGS. 17A-C show the (A) structural formula; (B) LC-MS spectrum; and (C) ESI-MS (m/z) calcd (found): 592.2 (592.1) for [M]$^+$ of G32.
Figure 17B:
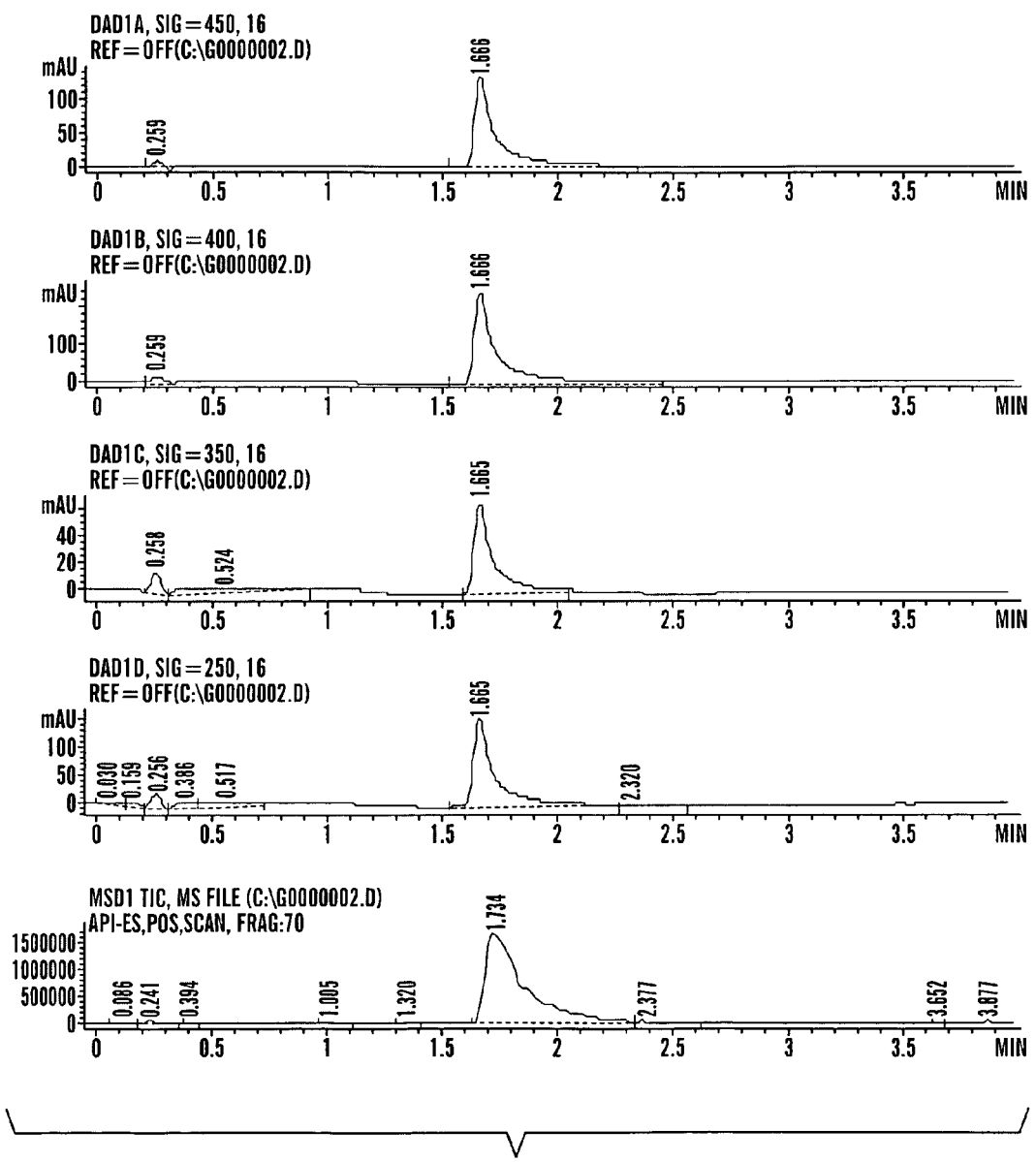
Figure 17C:
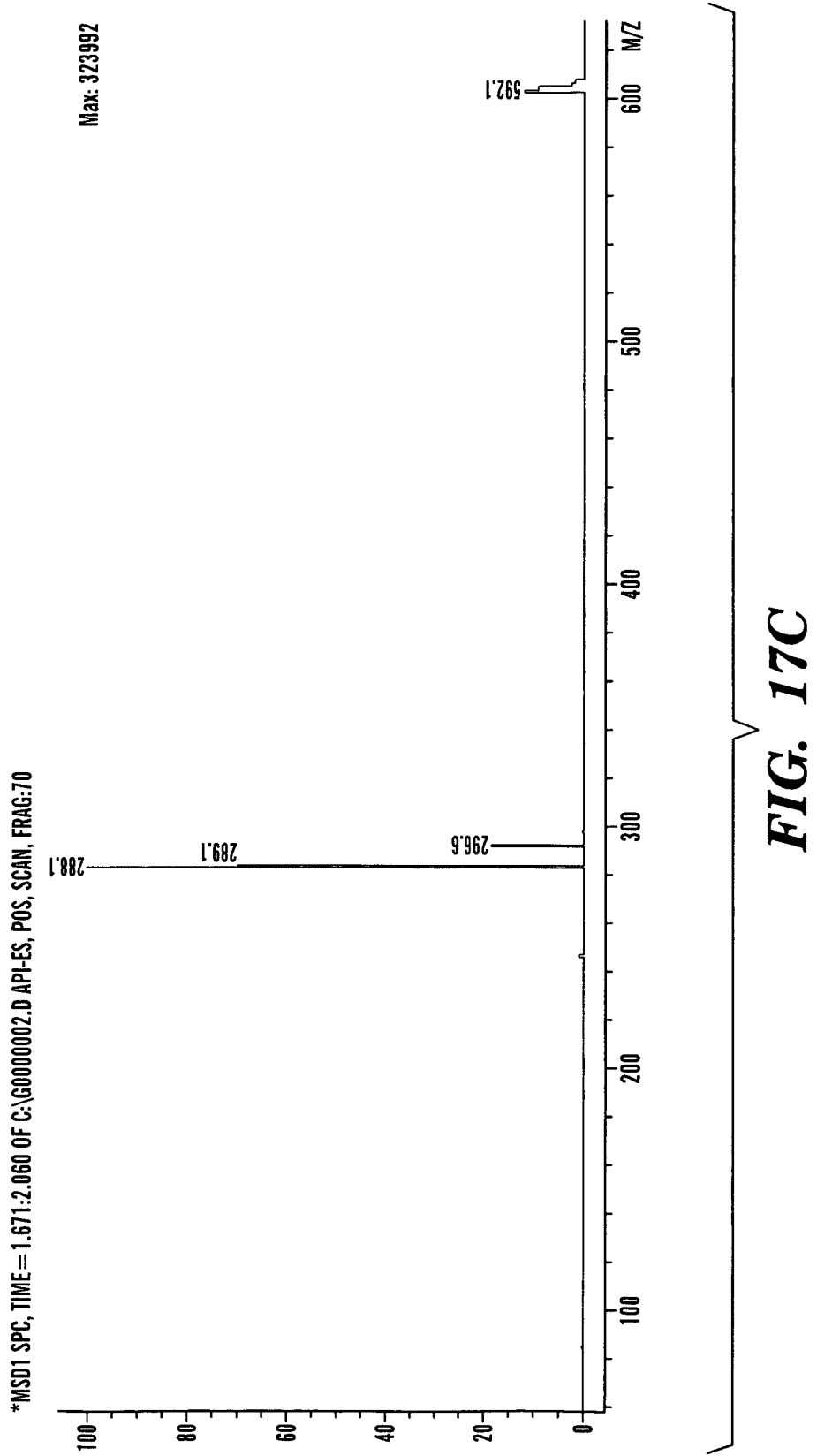
Figure 18:
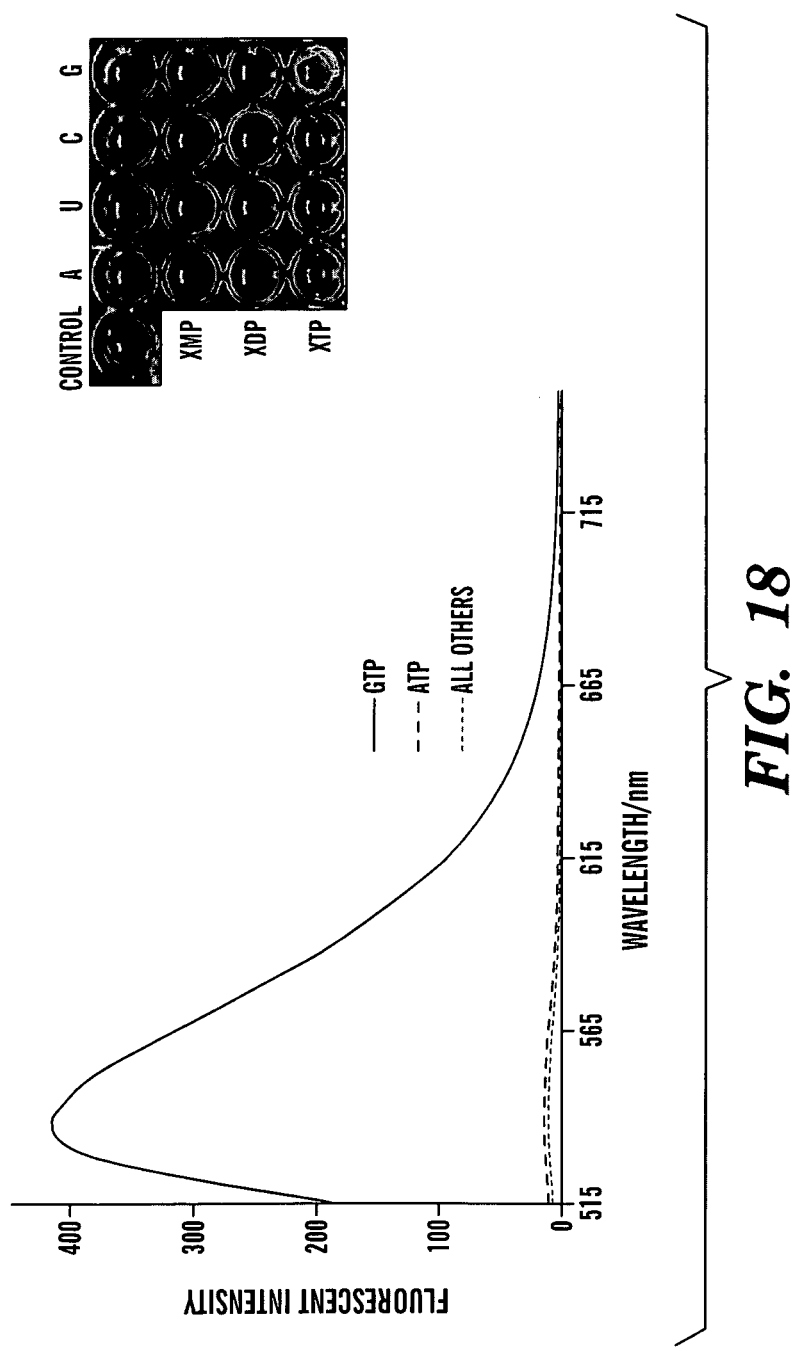
FIG. 18 shows fluorescence emission spectra (excitation: 480 nm, cutoff: 515 nm) of G49 (1 μM) with 100 μM of GTP, ATP, all other 14 analytes and blank control in 10 mM HEPES buffer (pH=7.4) with 1% DMSO. (inset: 96-well photo taken using 5 μM of G49 for better visualization, otherwise in the same condition, under 365 nm UV lamp light.)
Figure 19B:
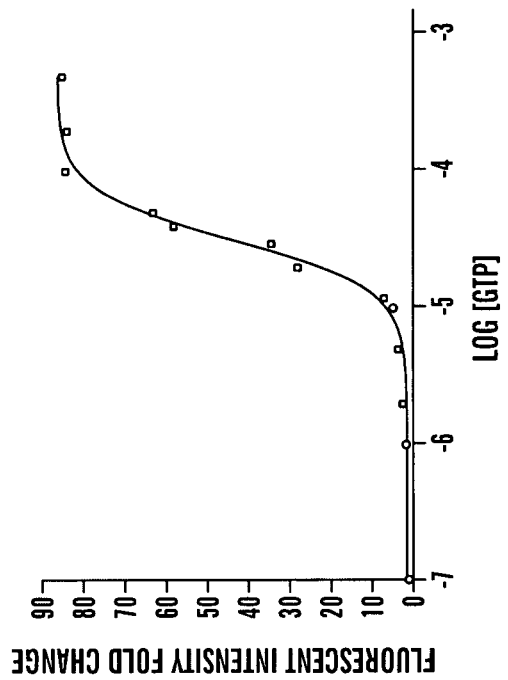
FIGS. 19A-B show plots of (A) fluorescent intensity for G32 and (B) G32 titration experiment with GTP.
Figure 19A:
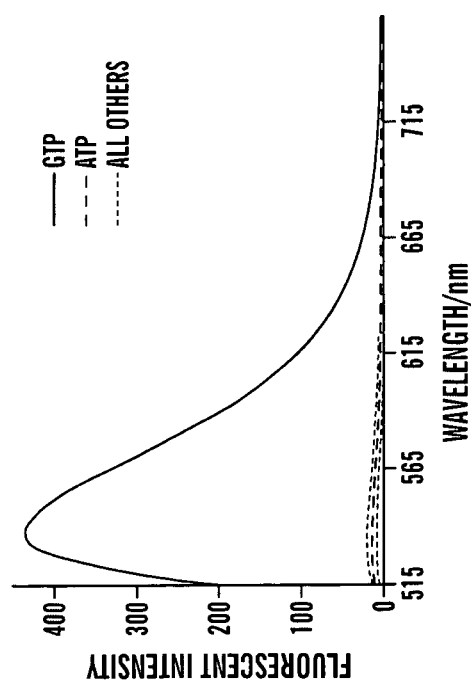

To 2-chlorotrityl alcohol resin 7 (1 g, 1.37 mmol/g) presuspended in dichloromethane (10 mL) in a 20 mL vial for 10 min was added thionyl chloride (1 mL, 10 eq), and the vial was shaken for 2 hrs at room temperature. The resin was filtered and washed with dichloromethane and acetonitrile alternatively for 5 times and dried in vacuum. The resin was then suspended in dichloromethane (10 mL) for 10 min and was added ethylenediamine (400 µL, 4 eq) and shaken at room temperature for 3 hrs. The resin was filtered and washed with dichloromethane and methanol alternatively for 5 times and dried in vacuum. See FIG. 13.

Example 7

Resin Bound Benzimidazolium Block (9)

Figure 14:
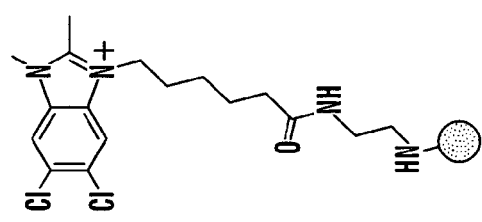
FIG. 14 shows the structural formula of resin bound benzoimidazolium block (9).

DIPEA (800 µL, 3 eq), HATU (1.56 g, 3 eq) and 6 (1.64 g, 3 eq) in 60 mL dichloromethane and 20 ml DMF were shaken at room temperature for 30 mins. To this solution was added resin 8 (1 g, 1 eq) and shaken at room temperature overnight. The resin was filtered and washed with dichloromethane and methanol alternatively for 5 times and dried in vacuum. To an aliquot of the resin was added 100 µL 5% trifluoroacetic acid/dichloromethane cleavage cocktail solution and shook for 15 mins. The solution was subjected to LC-MS. ESI-MS (m/z) calcd (found): 371.1 (371.3) for [M]$^+$. See FIG. 14.

Example 8

Resin Bound Benzimidazolium Dyes (10)

Figure 15:
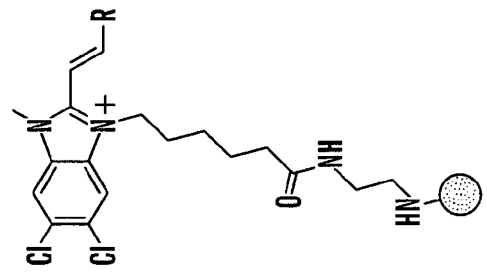
FIG. 15 shows the structural formula of resin bound benzimidazolium dyes (10).

To resin 9 (10 mg, 1 eq) was added each aldehyde (see FIG. 2) (10 eq) in 1-methyl-2-pyrrolidinone (300 µL) solution and pyrrolidine (2 µL). The reaction was shaken in the dark and under a positive pressure of nitrogen for 24 hrs. The resin was filtered and washed with DMF (5 times), alternatively dichloromethane and methanol (5 times), dichloromethane (5 times) and dried in vacuum. See FIG. 15.

Example 9

Cleavage of Benzimidazolium Dyes From Resin (11)

Resin 10 (10 mg) was suspended in 5% trifluoroacetic acid/dichloromethane cleavage cocktail solution (0.5 mL) and shaken for 15 min. The resin was filtered off and washed with dichloromethane (1 mL) and methanol (1 mL). The solutions were collected and evaporated to dryness to obtain the benzimidazolium dyes. See Table 2 below.

TABLE 2

Benzimidazolium dye library member list.

| Compound Code | Purity (%)† | $\lambda_{ex}$ (nm)‡ | $\lambda_{em}$ (nm)‡ |
|---|---|---|---|
| G1 | 99.2 | 460 | 580 |
| G2 | 96.4 | 390 | 470 |
| G3 | 94.2 | 370 | 470 |
| G4 | 96.3 | 390 | 490 |
| G5 | 98.7 | 360 | 560 |
| G6 | 98.5 | 360 | 560 |
| G7 | 98.6 | 420 | 490 |
| G8 | 98.8 | 410 | 480 |
| G9 | 92.1 | 420 | 560 |
| G10 | 97.4 | 450 | 540 |
| G11 | 93.5 | 420 | 520 |
| G12 | 98.9 | 450 | 550 |
| G13 | 97.6 | 450 | 600 |
| G14 | 94.5 | 390 | 490 |
| G15 | 92.3 | 390 | 490 |
| G16 | 92.9 | 430 | 540 |
| G17 | 96.3 | 390 | 500 |
| G18 | 96.8 | 370 | 460 |
| G19 | 91.1 | 360 | 450 |
| G20 | 97.6 | 360 | 440 |
| G21 | 98.0 | 380 | 470 |
| G22 | 97.6 | 390 | 480 |
| G23 | 97.8 | 420 | 530 |
| G24 | 92.0 | 460 | 540 |
| G25 | 95.4 | 450 | 600 |
| G26 | 97.1 | 390 | 540 |
| G27 | 95.6 | 460 | 550 |
| G28 | 98.7 | 380 | 470 |
| G29 | 95.0 | 380 | 560 |
| G30 | 97.1 | 390 | 480 |
| G31 | 90.5 | 380 | 430 |
| G32 | 96.8 | 450 | 520 |
| G33 | 98.2 | 450 | 540 |
| G34 | 98.7 | 380 | 450 |
| G35 | 95.5 | 450 | 560 |
| G36 | 95.1 | 360 | 460 |
| G37 | 96.5 | 460 | 520 |
| G38 | 80.3 | 360 | 510 |
| G39 | 97.3 | 430 | 480 |
| G40 | 99.7 | 400 | 520 |
| G41 | 98.4 | 380 | 490 |

TABLE 2-continued

Benzimidazolium dye library member list.

| Compound Code | Purity (%)[†] | $\lambda_{ex}$ (nm)[‡] | $\lambda_{em}$ (nm)[‡] |
|---|---|---|---|
| G42 | 95.8 | 420 | 490 |
| G43 | 98.7 | 400 | 490 |
| G44 | 98.5 | 390 | 480 |
| G45 | 98.7 | 410 | 470 |
| G46 | 99.2 | 380 | 440 |
| G47 | 99.7 | 380 | 470 |
| G48 | 98.0 | 430 | 530 |
| G49 | 96.5 | 450 | 520 |
| G50 | 92.6 | 370 | 450 |
| G51 | 96.4 | 360 | 550 |
| G52 | 99.4 | 410 | 470 |
| G53 | 98.9 | 380 | 520 |
| G54 | 96.2 | 380 | 640 |
| G55 | 99.6 | 370 | 440 |
| G56 | 98.6 | 370 | 440 |
| G57 | 98.0 | 400 | 520 |
| G58 | 98.4 | 360 | 470 |
| G59 | 97.6 | 450 | 540 |
| G60 | 96.0 | 430 | 490 |
| G61 | 97.5 | 400 | 510 |
| G62 | 94.0 | 460 | 550 |
| G63 | 74.3 | 490 | 620 |
| G64 | 97.8 | 460 | 560 |
| G65 | 94.6 | 460 | 560 |
| G66 | 97.2 | 450 | 650 |
| G67 | 98.1 | 460 | 550 |
| G68 | 97.1 | 350 | 460 |
| G69 | 96.3 | 460 | 560 |
| G70 | 92.0 | 380 | 560 |
| G71 | 90.6 | 460 | 560 |
| G72 | 99.4 | 380 | 560 |
| G73 | 93.7 | 380 | 460 |
| G74 | 98.0 | 410 | 500 |
| G75 | 99.0 | 380 | 630 |
| G76 | 95.4 | 390 | 470 |
| G77 | 95.5 | 400 | 560 |
| G78 | 98.7 | 430 | 520 |
| G79 | 93.7 | 420 | 470 |
| G80 | 97.4 | 400 | 490 |
| G81 | 99.0 | 490 | 530 |
| G82 | 99.6 | 430 | 490 |
| G83 | 98.3 | 350 | 460 |
| G84 | 95.4 | 420 | 500 |
| G85 | 98.1 | 390 | 500 |
| G86 | 96.0 | 450 | 510 |
| G87 | 99.4 | 380 | 470 |
| G88 | 99.6 | 380 | 480 |
| G89 | 95.8 | 380 | 540 |
| G90 | 99.0 | 410 | 510 |
| G91 | 98.7 | 380 | 470 |
| G92 | 95.8 | 450 | 550 |
| G93 | 99.1 | 380 | 440 |
| G94 | 98.5 | 390 | 480 |
| G95 | 93.4 | 360 | 440 |
| G96 | 98.1 | 420 | 500 |

[†]Products were collected without further purification. Purity of each product was calculated based on LC-MS 350 nm trace area sizes.
[‡]All fluorescence excitation and emission data were recorded on a Gemini XS fluorescent plate reader with 1 mM compounds in methanol (100 μL) in Grainer 96 well black polypropylene plates.

Example 10

Primary Screening Procedure

A primary screening of the dye library was performed with 4 μM, 10 μM, 20 μM and 40 μM Heparin in 10 mM HEPES buffer (pH 7.4) in 96 well microplates using a fluorescence plate reader. Different concentrations of heparin were selected to address the detection limits and also get a basic impression about the binding affinity. Forty-three out of 96 compounds showed responses to heparin, including fluorescence quenching, fluorescence increase, and fluorescence emission red-shifts. At the same time a protamine assay was performed to check the reversibility of the binding events. Protamine (0.1 mg/ml) was added to the assay solution of 10 μM dyes equilibrated with 20μM heparin.

Figure 4B:
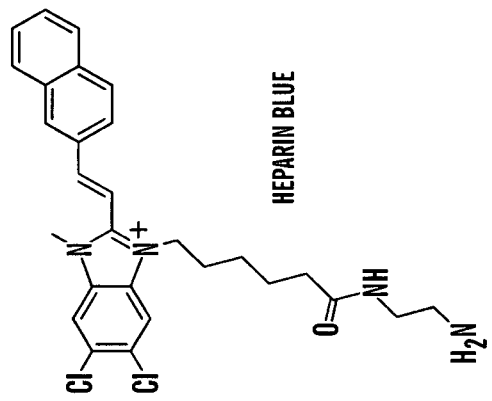
FIGS. 4A-J show (A) structure of Heparin Orange; (B) structure of Heparin Blue; (C) fluorescence emission spectra (excitation: 380 nm, cutoff: 420 nm) of Heparin Orange (10 µM) with 0, 0.03, 0.05, 0.1, 0.25, 0.5 µM UFH in 10 mM 4-(2-hydroxyethyl)-1-piperazineethanesulfonic acid (HEPES) buffer (pH=7.4) with 1% dimethyl sulfoxide (DMSO); (D) fluorescence emission spectra (excitation: 380 nm, cutoff: 420 nm) of Heparin Blue (10 µM) with 0, 0.03, 0.05, 0.1, 0.25, 0.5 µM UFH in 10 mM HEPES buffer (pH=7.4) with 1% DMSO; (E) fluorescent emission ratio at 595 nm to 520 nm of Heparin Orange (10 µM) upon addition of LMWH and UFH at 0, 0.02, 0.04, 0.06, 0.1, 0.12, 0.2, 0.3, 0.4, 0.5, 0.6, 0.8, 1, 1.2, 1.5, 1.6, 2, 2.5, 3, 3.2, 4, 5, 6, 8, 10, 16, 20 µM in 10 mM HEPES buffer (pH=7.4) with 1% DMSO; (F) fluorescent emission intensity fold change at 480 nm of Heparin Blue (10 µM) upon addition of LMWH and UF at upon addition of LMWH and UFH at 0, 0.02, 0.04, 0.06, 0.1, 0.12, 0.2, 0.3, 0.4, 0.5, 0.6, 0.8, 1, 1.2, 1.5, 1.6, 2, 2.5, 3, 3.2, 4, 5, 6, 8, 10, 16, 20 µM in 10 mM HEPES buffer (pH=7.4) with 1% DMSO; (G) photo of Heparin Orange (10 µM) with indicated concentrations of UFH and LMWH in 10 mM HEPES buffer (pH=7.4) with 1% DMSO in a 96 well plate under 365 nm UV lamp light; (H) photo of Heparin Blue (10 µM) with indicated concentrations of UFH and LMWH in 10 mM HEPES buffer (pH=7.4) with 1% DMSO in a 96 well plate under 365 nm UV lamp light; (I) fluorescent emission ratio at 595 nm to 520 nm of Heparin Orange (20 μM); (J) fluorescent emission of Heparin Blue (50μM) upon addition of LMWH and UFH at indicated concentrations in 20% pooled human plasma.
Figure 4A:
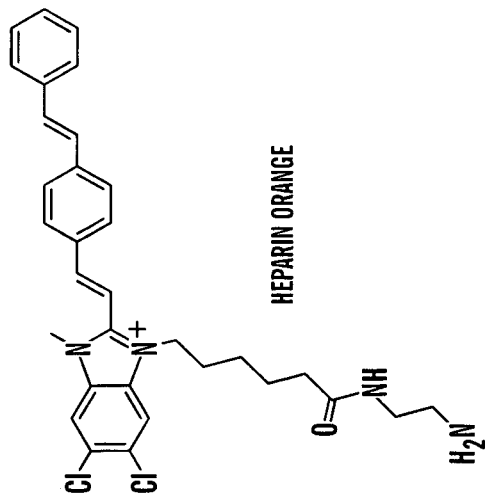

The fluorescent responses were compared with a blank control and 20μM of heparin. To further test whether the real application of the hit compounds in blood plasma assay is possible, a Heparin assay in blood plasma was performed. Briefly, 4 μM, 10 μM, 20 μM and 40 μM Heparin in 20% Human plasma/HEPES buffer was tested. Seven out of 43 compounds show response to heparin in human plasma. Two compounds (G26 and G45, see FIGS. 4A-B) show very impressive response to heparin: one, a fluorescent turn-on response in the blue range while the other, a dramatic red-shift.

Figure 4D:
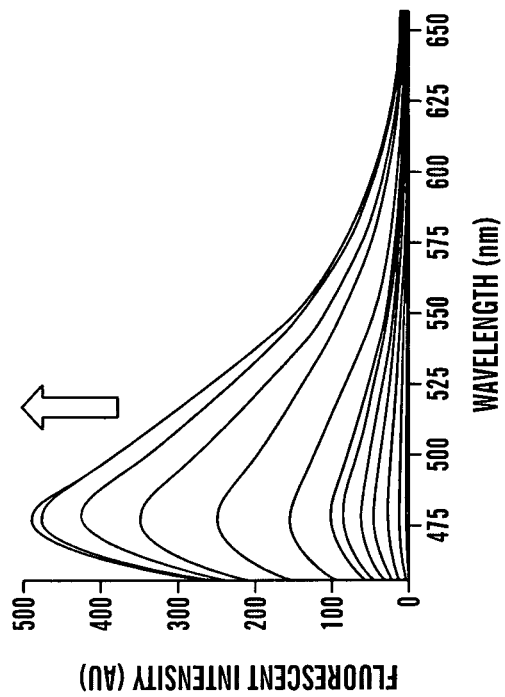
Figure 4C:
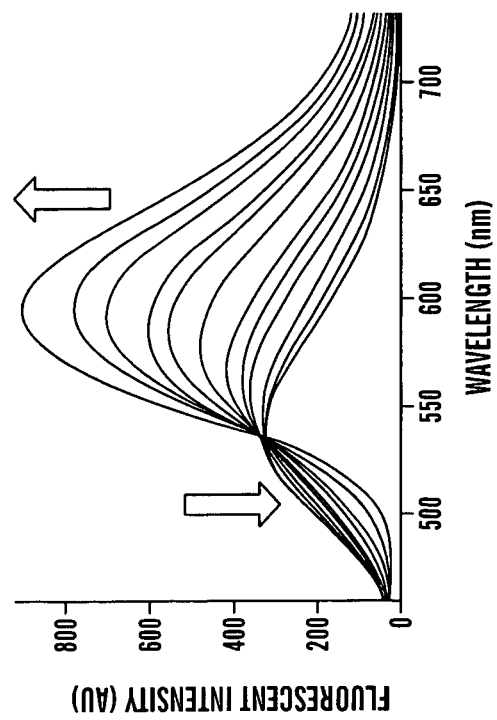
Figure 4F:
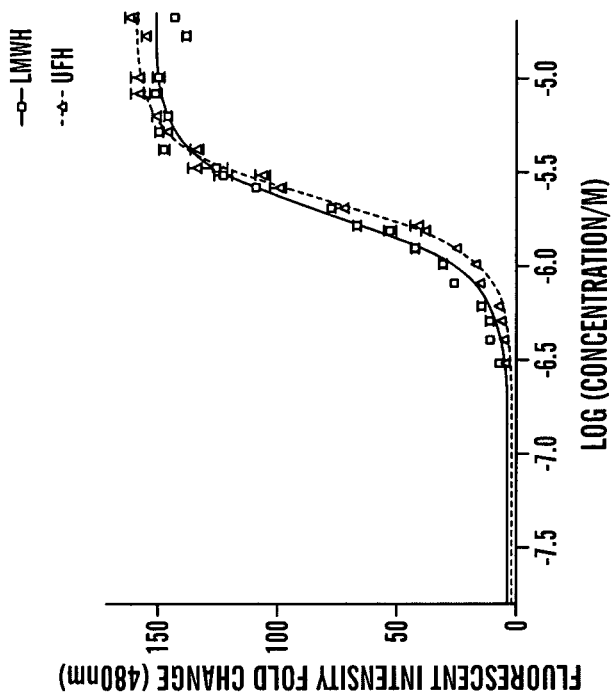
Figure 4E:
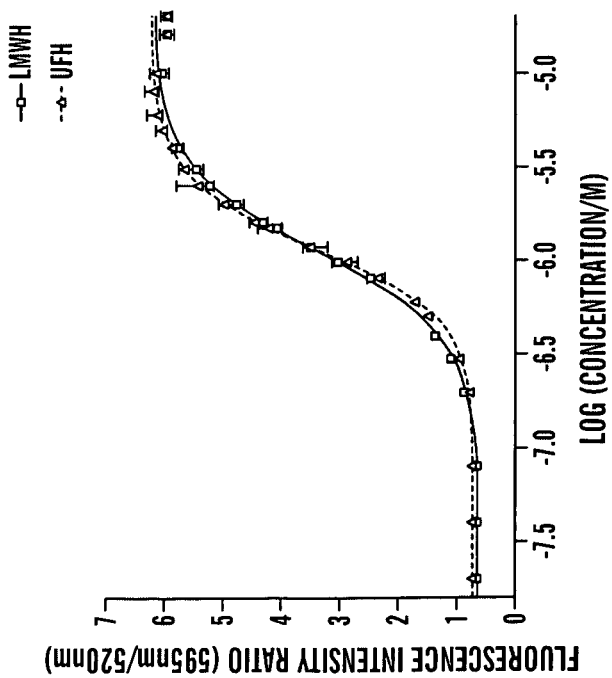
Figure 4G:
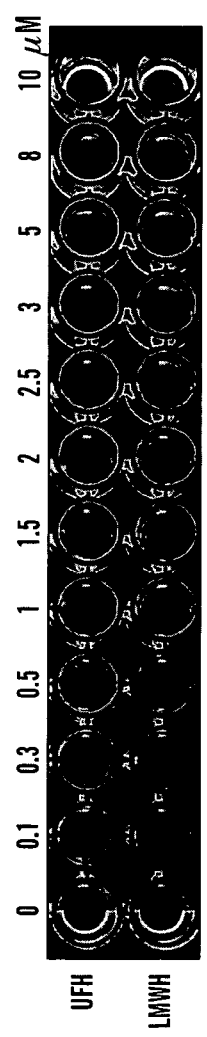

Compound G26 (see FIG. 4A) shifts from green fluorescence (520 nm) to orange (595 nm) upon addition of either UFH or LMWH (See FIG. 4C). The response is so obvious and unique that the result could be even easily distinguished by naked eyes (see FIG. 4G), thus the proposed name for this compound is Heparin Orange.

Figure 5A:
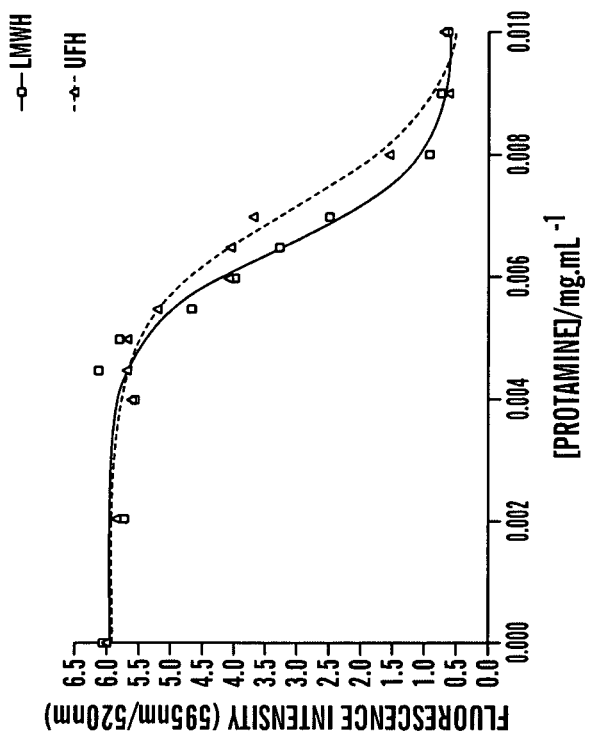
FIGS. 5A-B show plots of protamine titrations of Heparin Orange and Heparin Blue.
Figure 5B:
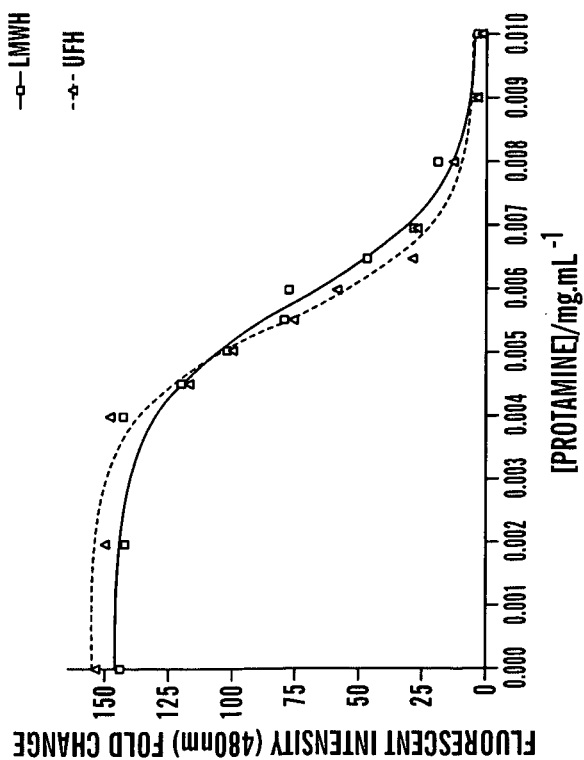
Figure 6:
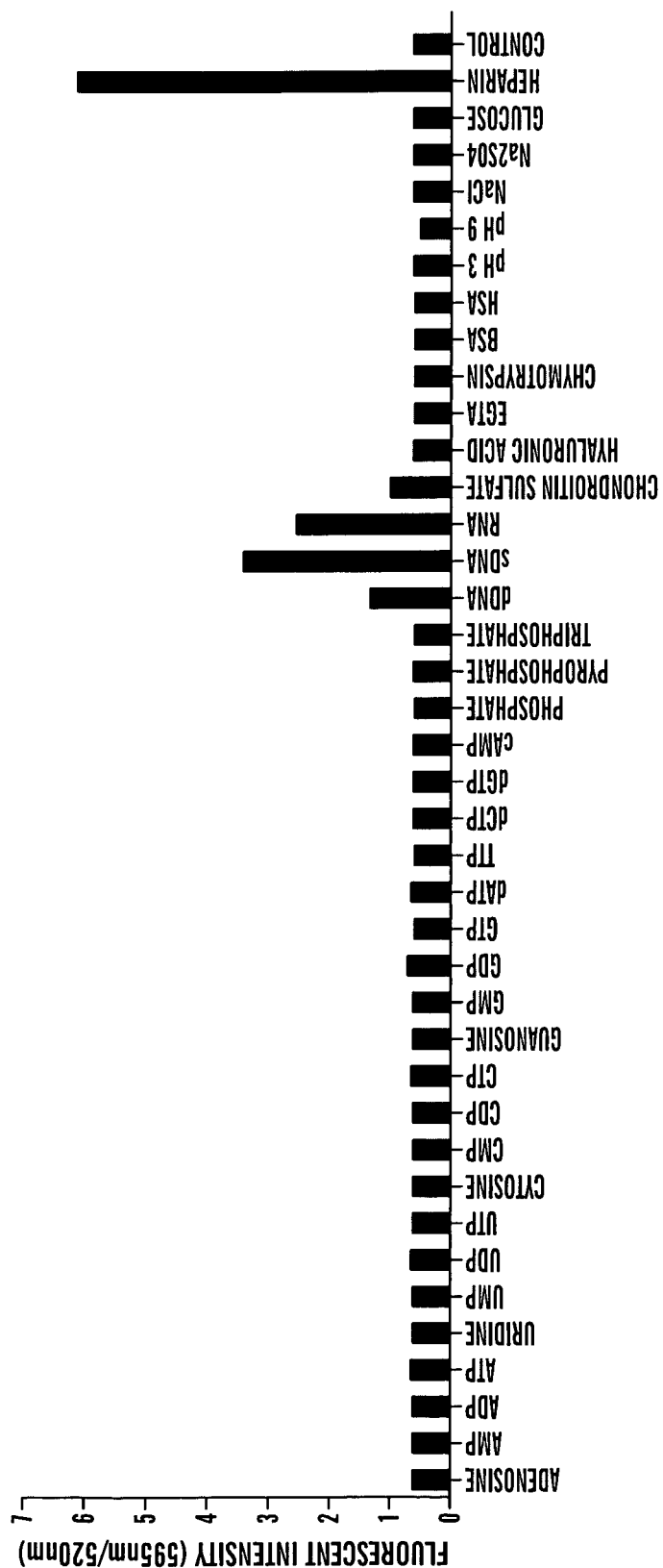
FIG. 6 shows a bar graph illustrating the selectivity of Heparin Orange to heparin from relevant biological analytes.
Figure 7:
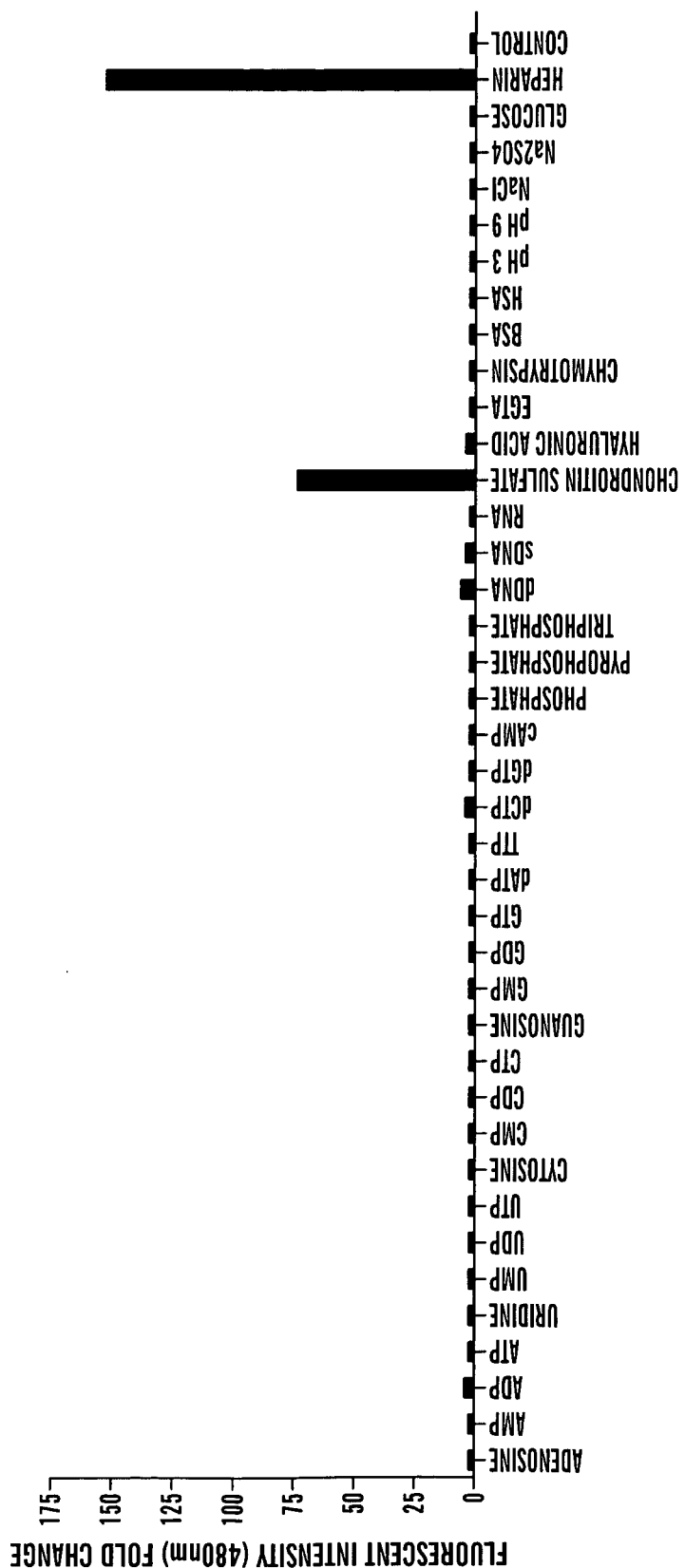
FIG. 7 shows a bar graph illustrating the selectivity of Heparin Blue to heparin from relevant biological analytes.
Figure 8A:
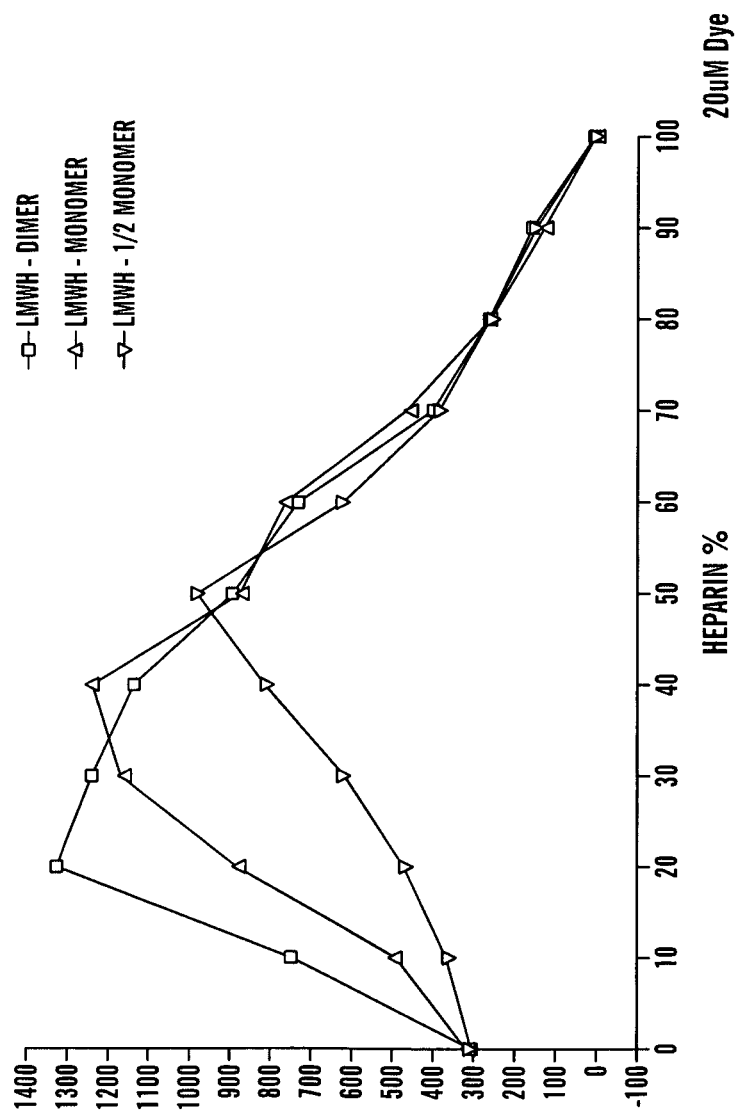
FIGS. 8A-C show Job's plots of Heparin Orange and Heparin Blue with different concentrations of UFH and LMWH.
Figure 8B:
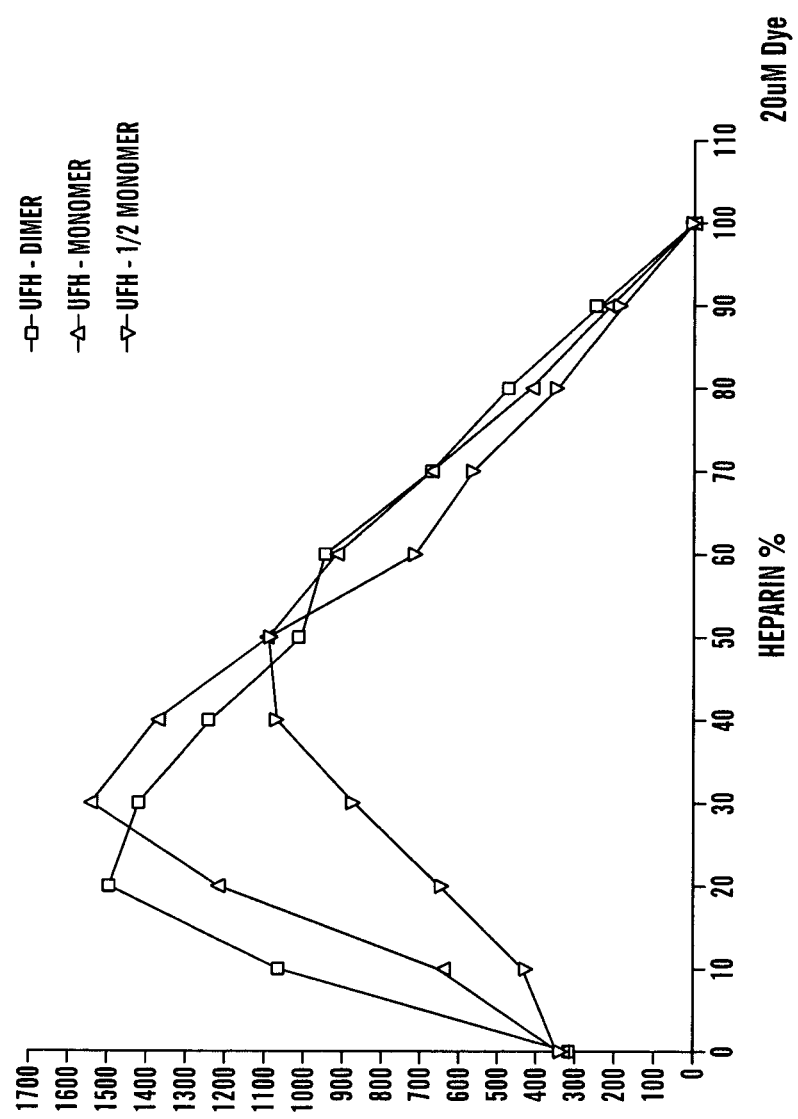
Figure 8C:
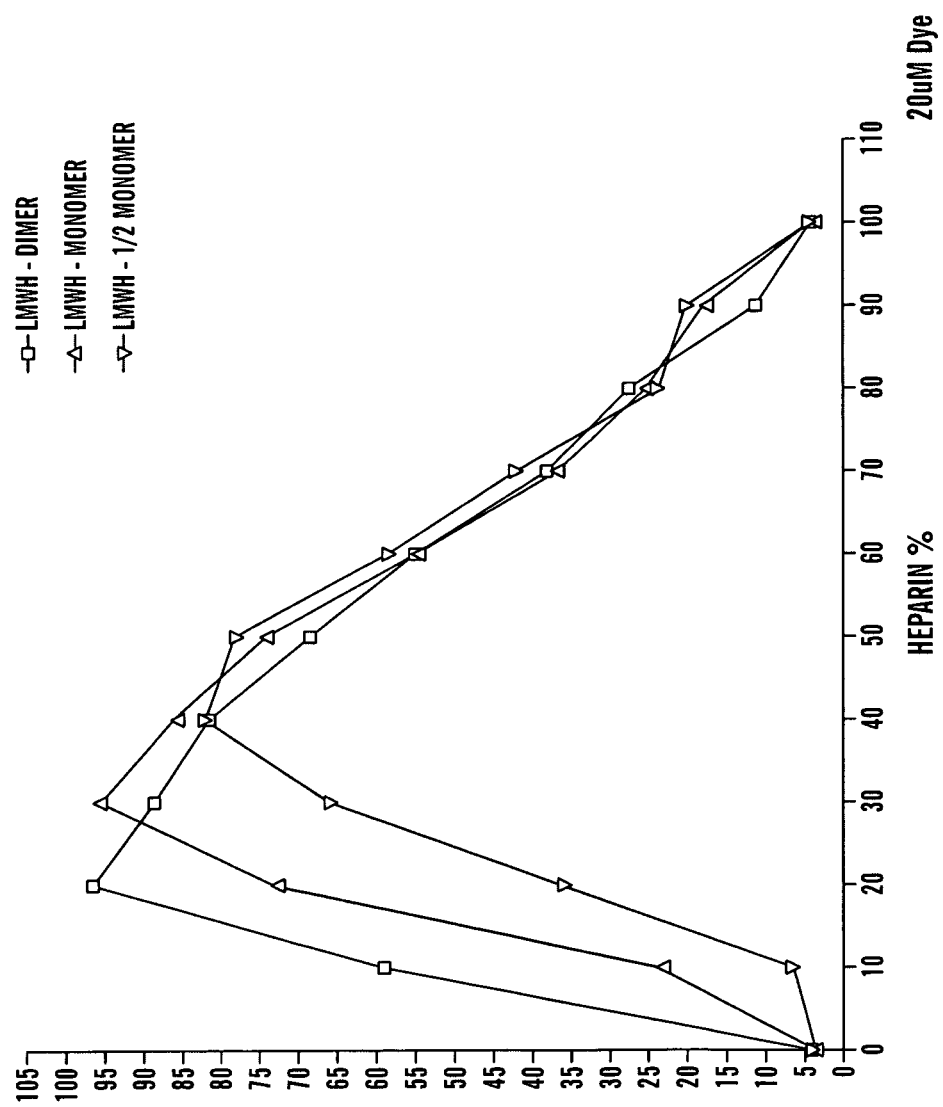

The quantum yields (Φ) of Heparin Orange before and after addition of heparin are 0.024 and 0.076, respectively. Job's plot demonstrated that Heparin Orange binds with heparin in a manner that one sugar monomer binds with two molecules of Heparin Orange. See FIG. 5A. This is congruent with the charge number of both molecules thus it was proposed that this is a charge interaction between the analyte and the sensor. However, the high selectivity between heparin and Heparin Orange indicated that the interaction between the two cannot only be attributed to electrostatic interaction. See FIGS. 6 and 7. Also, protamine titration experiment demonstrated that the binding event is reversible. The detection range of Heparin Orange in HEPES buffer covers from 0 to 5 μM.

Figure 4H:
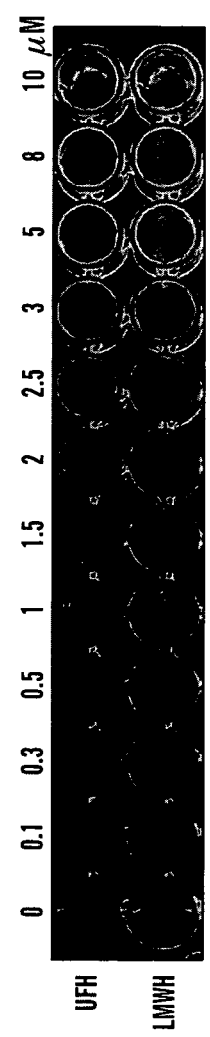
Figure 4J:
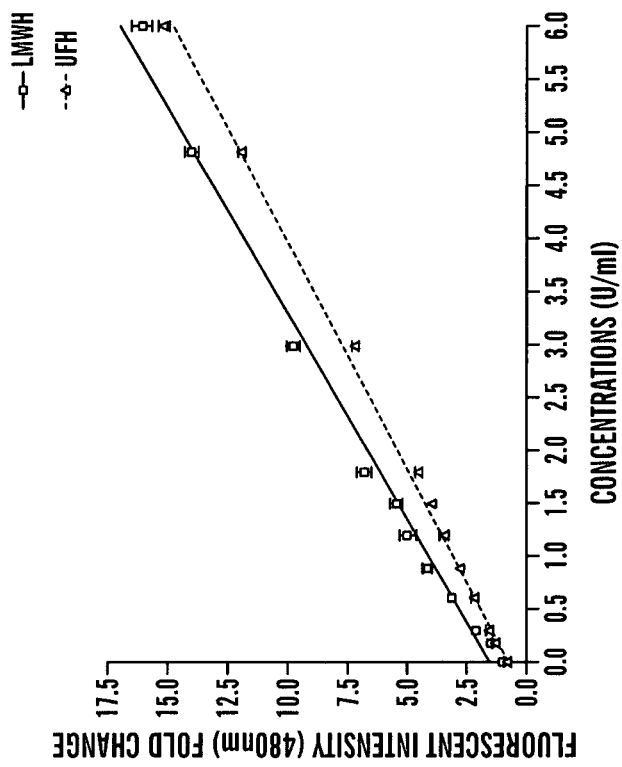
Figure 4I:
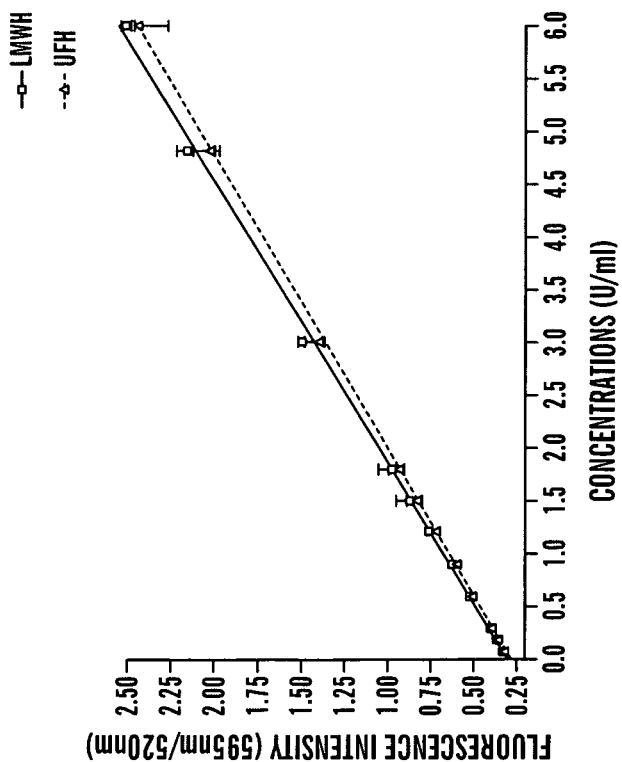

Compound G45 (see FIG. 4B) showed a dramatic increase of the fluorescence emission at 480 nm after addition of either UF or LMWH (see FIG. 4D) and was dubbed Heparin Blue. The response is also very obvious and that the result could be even noticed and distinguished by naked eyes (see FIG. 4H). The quantum yields (Φ) of Heparin Blue before and after are 0.034 and 0.145, respectively. Job's titration and protamine titration were also performed with Heparin Blue and similar results were obtained. See FIGS. 5B and 8A-C. The detection range of Heparin Blue in HEPES buffer is from 0 to 5 μM.

Example 11

Detection of Heparin in Blood Plasma

Standard detection curves for Heparin Orange and Heparin Blue were set up in 20% pooled human plasma. Briefly, indicated concentrations of UFH and LMWH were adopted into the pooled human plasma and then diluted five times with 10 mM HEPES buffer (pH=7.4). One μL of 2 mM Heparin Orange or 10 mM Heparin Blue in DMSO was added into 100 μL of the sample and fluorescent emission was recorded in the same conditions as in the buffer test. Due to the turbidity and fluorescent background of plasma, higher concentrations of chemosensors were applied. Heparin is administered at therapeutic dosing levels of 2-8 U/mL (13-53.4 μM) during cardiopulmonary surgery and 0.2-2 U/mL (1.3-13 μM) in post-operative and long-term care, and standard curves of UFH and LMWH were set up for both of the fluorescent chemosensors in the therapeutic range. The response is so obvious that these results could be distinguished by naked eyes thus these compounds has the potential to greatly facilitate the point-of-care detection.

Therefore, in one embodiment of the invention, one ratiometric and one turn-on fluorescent chemosensor for UFH and LMWH, are disclosed and were dubbed Heparin Orange and Heparin Blue respectively. They were discovered from high-throughput screening of a semi-designed combinatorial library, and this again demonstrated the power of diversity direction approach in the discovery of new fluorescent chemosensors.

Example 12

Selectivity of G32 and G49

Figure 21:
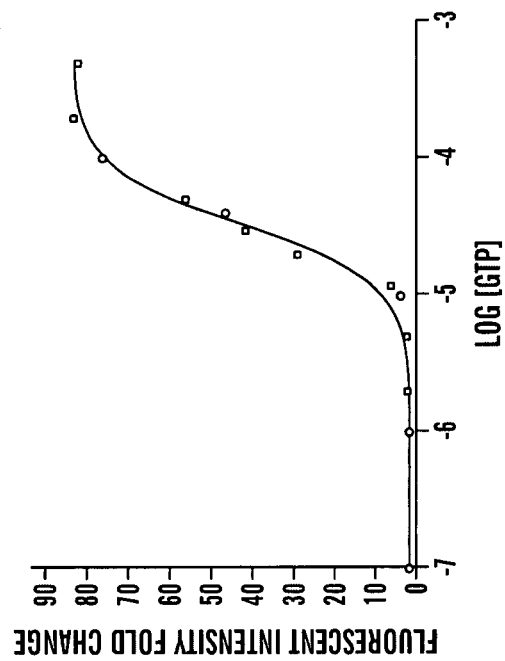
FIG. 21 shows a plot of G49 titration experiment with GTP.
Figure 20:
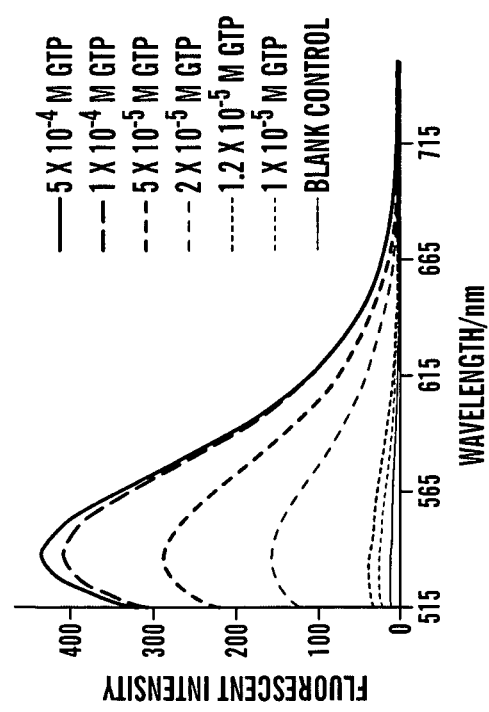
FIG. 20 shows fluorescence emission spectra of G49 with different concentrations of GTP.

To fully check the selectivity of the two hit compounds, all the nucleosides (adenosine, uridine, cytosine, guanosine) and nucleotides (XNP, where X=A, U, C, G, and N=Mono, Di, Tri) were tested systematically in 96 well plate. High selectivity of both G49 and G32 only to GTP was clearly exhibited without any obvious cross response to any of other nucleotides or nucleosides (see FIG. 20 for G49 and FIG. 21 for G32). As observed, G32 suffered from significant photo bleaching under strong irradiation light, so G49 was the focus of further analysis. Upon addition of GTP (100 µM) to G49 (1 µM), a red shift for both $\lambda_{ex}$ (from 450 nm to 480 nm) and $\lambda_{em}$ (from 520 nm to 540 nm) was observed. When excited at 480 nm, an approximately 80 fold fluorescence increase at an emission wavelength of 540 nm was observed only for GTP, while only two (ATP) or fewer fold changes were observed for all other analytes.

The quantum yields ($\Phi$) of G49 before and after addition of GTP were 0.003 and 0.074 respectively, by reference to fluorescein in 0.1 N NaOH ($\Phi$=0.95) with excitation at 450 nm. See Fery-Forgues, S., et al., *J. Chem. Edu.*, 76: 1260 (1999); and Brannon, J. H., et al., *J. Phys. Chem.*, 82, 705 (1978), which are hereby incorporated by reference in their entirety. A visual distinction was also possible when 5 µM of G49 was used (see FIG. 20, inset). Thus, the best turn-on GTP fluorescent sensor thus far from a semi-designed diversity-directed sensor approach is disclosed. Based on this unprecedented high selectivity of G49 to GTP and its visual green fluorescence increase, the compound is dubbed "GTP Green."

Benzimidazolium compounds were transferred to Grainer 384 well black polypropylene plates (final concentration as 20 µM) and tested against 100 µM AMP, ADP, ATP, UTP, CTP, GTP and blank control in 10 mM HEPES buffer (pH=7.4) with 1% DMSO. Fluorescence emission spectra were recorded on a Gemini XS fluorescent plate reader with excitation at 350 nm (cutoff: 420 nm), 400 nm (cutoff: 435 nm), 450 nm (cutoff: 495 nm).

FIG. 21A shows the results of the G32 selectivity test. Fluorescence emission spectra (excitation: 480 nm, cutoff: 515 nm) of 1 µM G32 with 100 µM GTP, ATP, adenosine, AMP, ADP, uridine, UMP, UDP, UTP, cytosine, CMP, CDP, CTP, guanosine, GMP, GDP and blank control in 10 mM HEPES buffer (pH=7.4) with 1% DMSO.

FIG. 21B shows the results of the G32 titration experiment with GTP. For each data point, 1 µM G32 was tested with indicated concentration of nucleotide in 10 mM HEPES buffer (pH=7.4) with 1% DMSO. Excitation at 480 nm (cutoff: 515 nm) and emission read at 540 nm. From the titration experiment, GTP showed association constants ($K_a$) to G32 as 31,162 $M^{-1}$. See Conners, K. A. *Binding Constants*; Wiley: New York (1987), which is hereby incorporated by reference in its entirety.

Figure 22A:
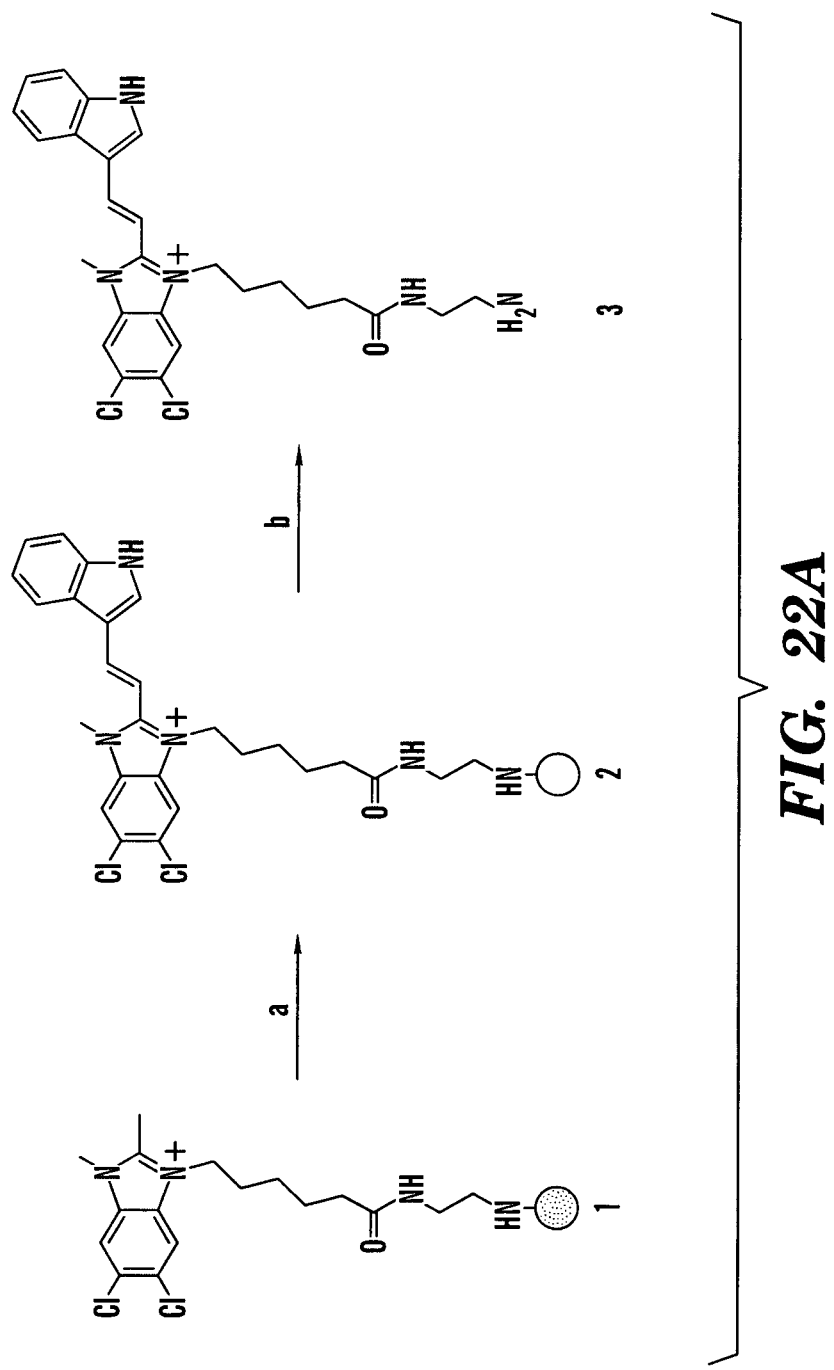
FIGS. 22A-C show (A) a reaction scheme illustrating the synthesis of GTP Green Analog 1 wherein (a) is indole-3-carboxaldehyde, pyrrolidine, NMP; AND (b) is 5% TFA/DCM; (B) LC-MS spectrum; and (C) ESI-MS spectrum of GTP Green Analog 1.
Figure 22B:
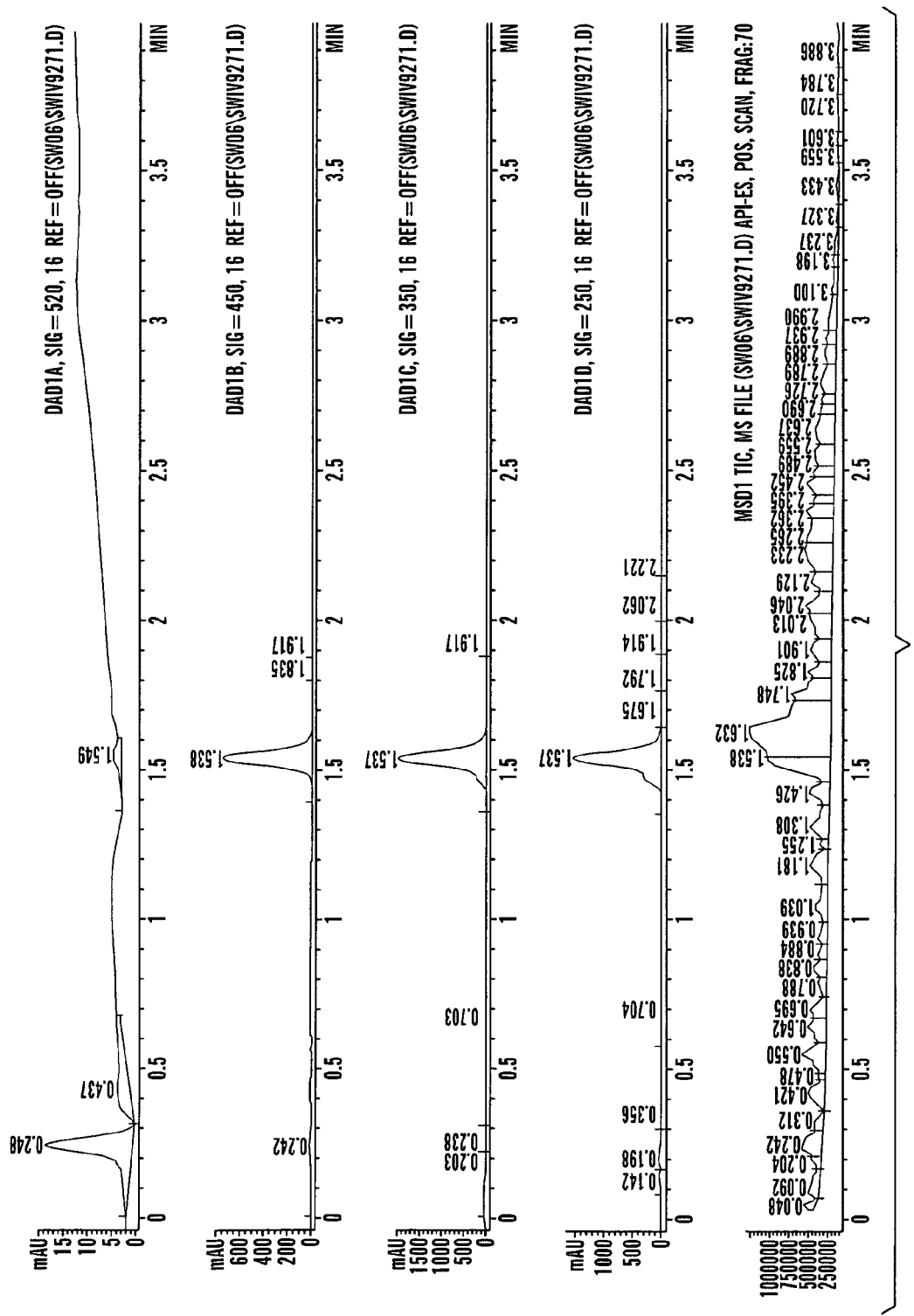
Figure 22C:
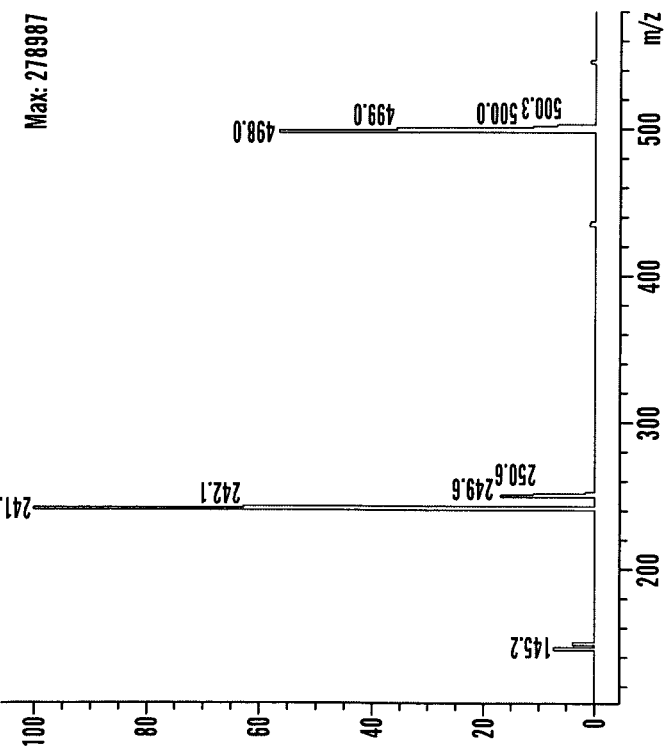

FIG. 22 shows Fluorescence emission spectra of G49 with different concentrations of GTP. Fluorescence emission spectra (excitation: 480 nm, cutoff: 495 nm) of 1 µM G49 with 500 µM, 100 µM, 50 µM, 20 µM, 12 µM, 10 µM GTP and blank control in 10 mM HEPES buffer (pH=7.4) with 1% DMSO.

Figure 23:
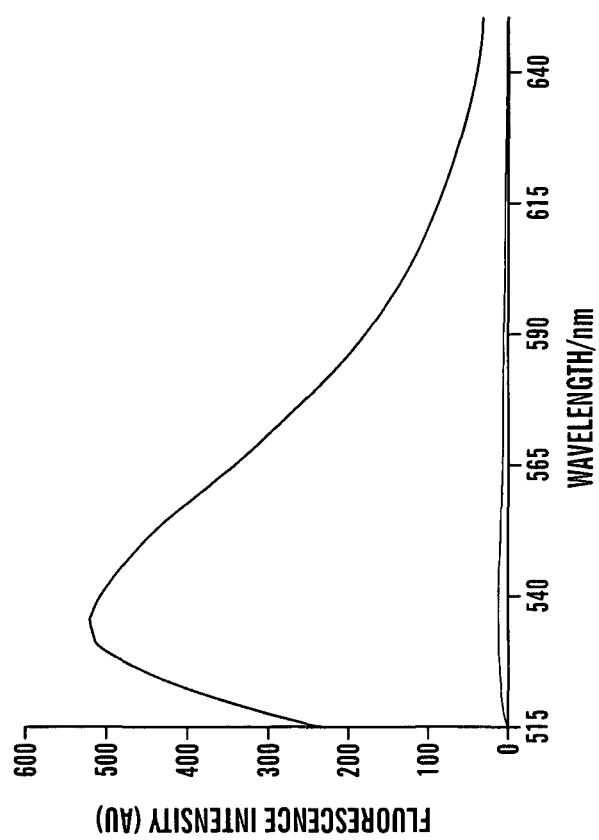
FIG. 23 is fluorescence emission spectra (excitation: 480 nm, cutoff: 515 nm) of 1 μM GTP Green Analog 1 with 100 μM GTP, ATP, adenosine, AMP, ADP, uridine, UMP, UDP, UTP, cytosine, CMP, CDP, CTP, guanosine, GMP, GDP and blank control in 10 mM HEPES buffer (pH=7.4) with 1% DMSO.

FIG. 23 shows the results of the G49 titration experiment with GTP. For each data point, 1 µM G49 was tested with indicated concentration of nucleotide in 10 mM HEPES buffer (pH=7.4) with 1% DMSO. Excitation at 480 nm (cutoff: 515 nm) and emission read at 540 nm. From the titration experiment, GTP showed association constants ($K_a$) to G49 as 30,030 $M^{-1}$. See Conners, K. A., Binding Constants; Wiley: New York (1987), which is hereby incorporated by reference in its entirety.

Example 13

Synthesis of GTP Analog 1

Figure 24A:
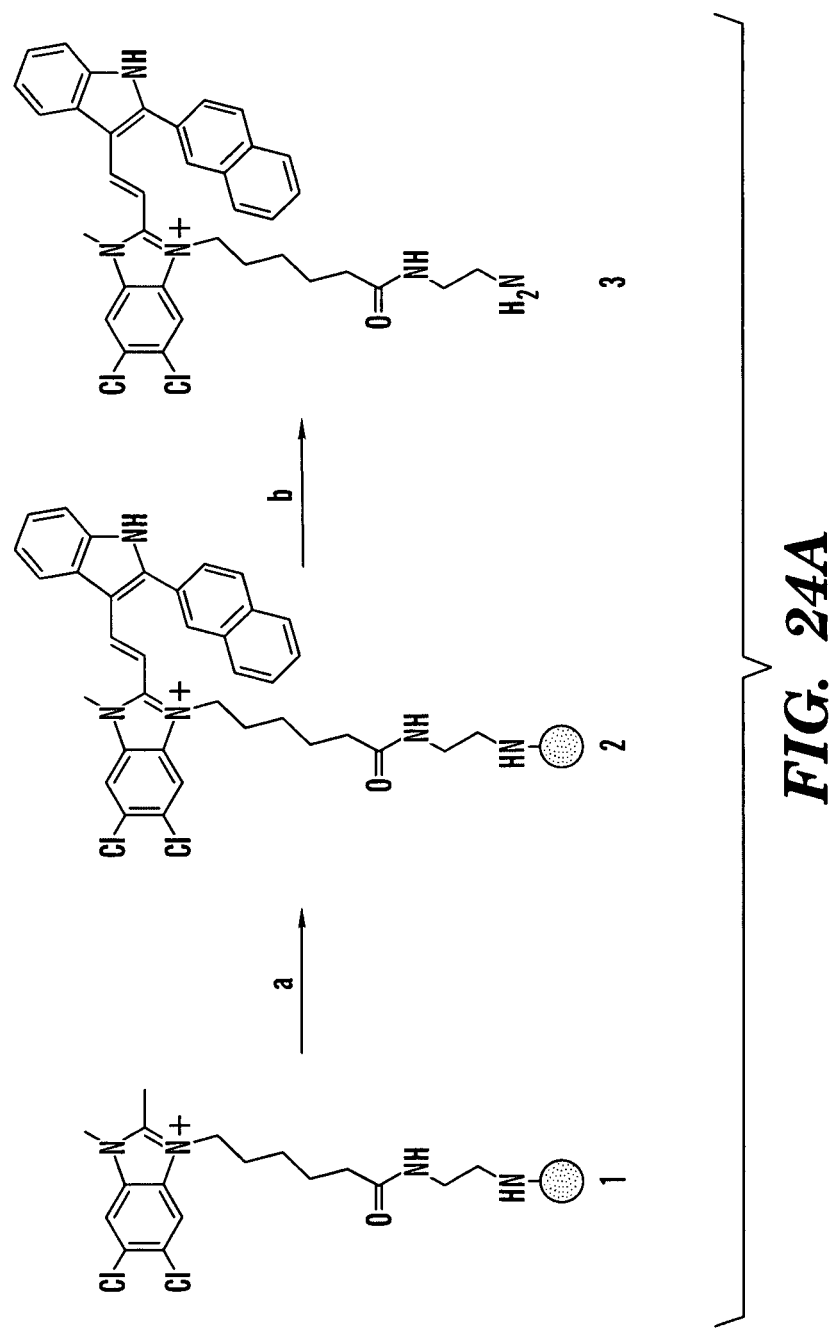
FIGS. 24A-C show (A) the reaction scheme illustrating the synthesis of GTP Green Analog 2, wherein (a) is 2-naphthalene-indole-3-carboxaldehyde, pyrrolidine, NMP; and (b) is 5% TFA/DCM; (B) LC-MS spectrum; and (C) ESI-MS spectrum of GTP Green Analog 2; ESI-MS (m/z) calcd (found): 624.23 (623.9) for [M]+.

To resin 1 (10 mg, 1 eq) was added indole-3-carboxaldehyde (10 eq) in 1-methyl-2-pyrrolidinone (300 µL) solution and pyrrolidine (2 µL). The reaction was shaken in dark and under a positive pressure of nitrogen for 24 hrs. The resin was filtered and washed with DMF (5 times), alternatively dichloromethane and methanol (5 times), dichloromethane (5 times) and dried in vacuum. See FIG. 24A, wherein (a) is indole-3-carboxaldehyde, pyrrolidine, NMP; and (b) is 5% TFA/DCM.

Resin 2 (10 mg) was suspended in 5% trifluoroacetic acid/dichloromethane cleavage cocktail solution (0.5 mL) and shook for 15 min. The resin was filtered off and washed with dichloromethane (1 mL) and methanol (1 mL). The solutions were collected and evaporated to dryness to obtain the benzimidazolium dye 3.

Figure 24B:
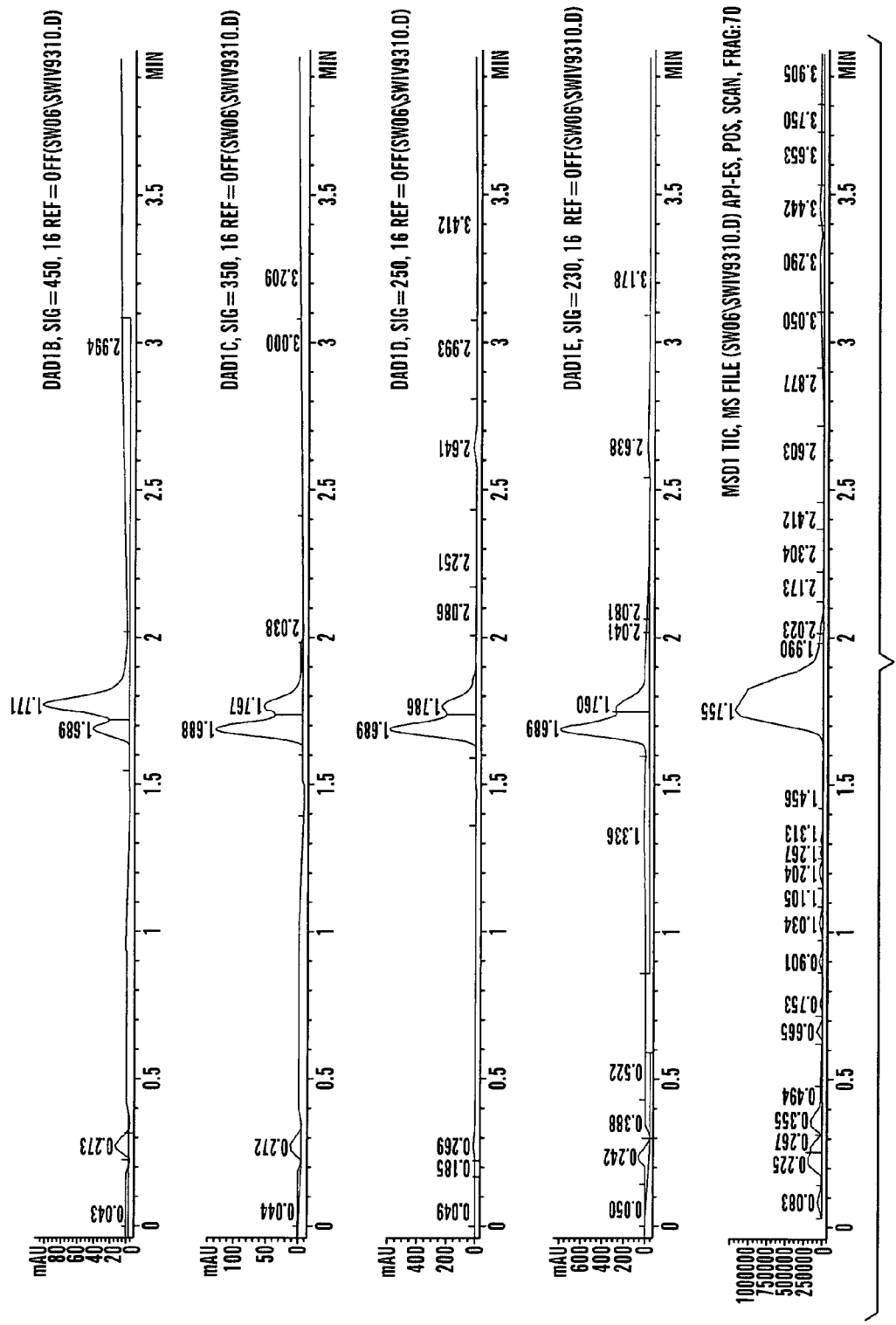
Figure 24C:
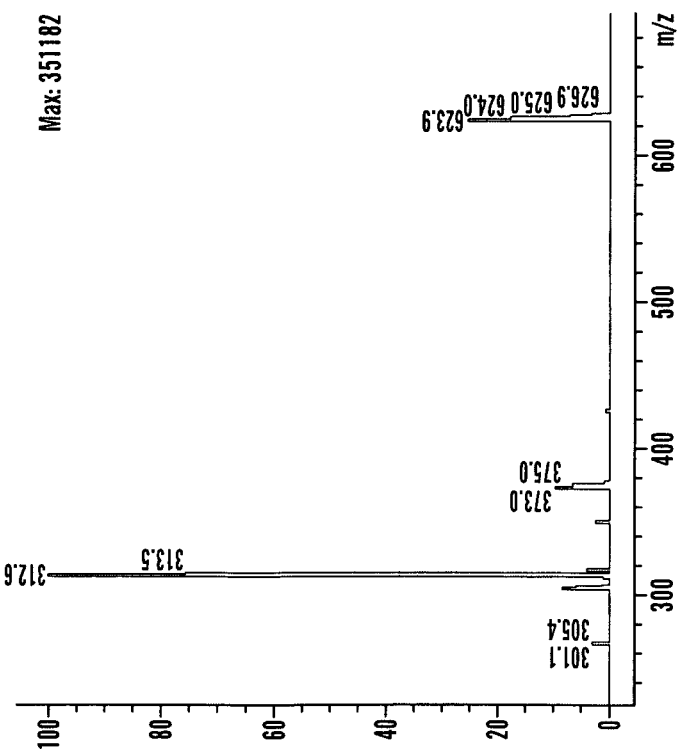

$^1$H NMR (DMSO): 8.507 (s, 2H), 8.248 (s, 1H), 8.138 (m, 1H), 8.084 (d, 1H, J=16 Hz), 7.975 (t, 1H), 7.564 (m, 1H) 7.298 (m, 2H), 7.092 (d, 1H, J=16 Hz), 4.615 (m, 2H), 4.143 (s, 3H), 3.227 (m, 2H), 2.807 (t, 2H), 2.067 (t, 2H), 1.818 (m, 2H), 1.547 (m, 2H), 1.369 (m, 2H). ESI-MS (m/z) calcd (found): 498.18 (498.0) for [M]+. See FIGS. 24B-C.

Figure 25:
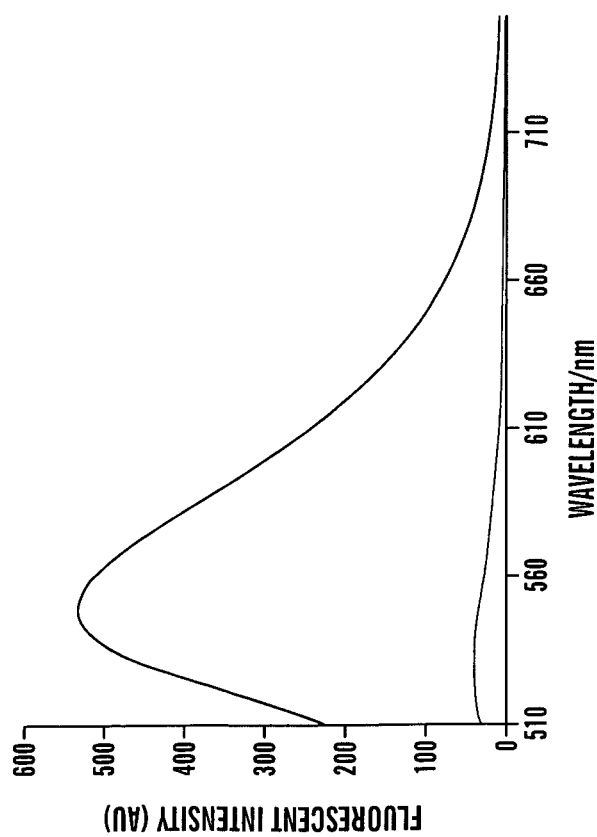
FIG. 25 shows fluorescence emission spectra (excitation: 470 nm, cutoff: 495 nm) of 1 μM GTP Green Analog 2 with 100 μM GTP, ATP, adenosine, AMP, ADP, uridine, UMP, UDP, UTP, cytosine, CMP, CDP, CTP, guanosine, GMP, GDP and blank control in 10 mM HEPES buffer (pH=7.4) with 1% DMSO.

Fluorescence emission spectra (excitation: 480 nm, cutoff: 515 nm) of 1 µM GTP Green Analog 1 with 100 µM GTP, ATP, adenosine, AMP, ADP, uridine, UMP, UDP, UTP, cytosine, CMP, CDP, CTP, guanosine, GMP, GDP and blank control in 10 mM HEPES buffer (pH=7.4) with 1% DMSO. See FIG. 25.

Example 14

Synthesis of GTP Analog 2

Figure 26A:
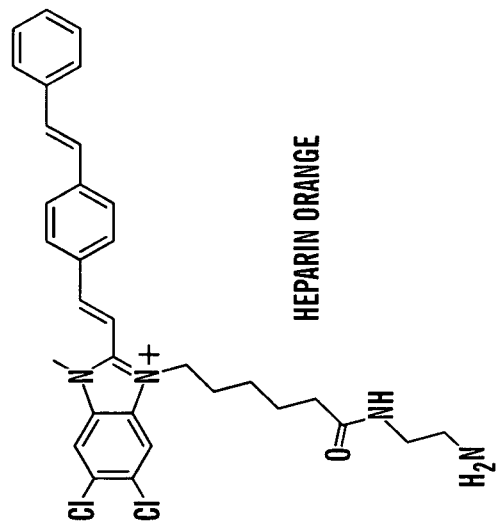
FIGS. 26A-B show the (A) structural formula; and (B) LC-MS spectrum of G26 (Heparin Orange).

To resin 1 (10 mg, 1 eq) was added 2- naphthalene-indole-3-carboxaldehyde (10 eq) in 1-methyl-2-pyrrolidinone (300 µL) solution and pyrrolidine (2 µL). The reaction was shaken in dark and under a positive pressure of nitrogen for 24 hrs. The resin was filtered and washed with DMF (5 times), alternatively dichloromethane and methanol (5 times), dichloromethane (5 times) and dried in vacuum. See FIG. 26A, wherein (a) is 2-napthalene-indole-3-carboxaldehyde, pyrrolidine, NMP; and (b) is 5% TFA/DCM.

Figure 26B:
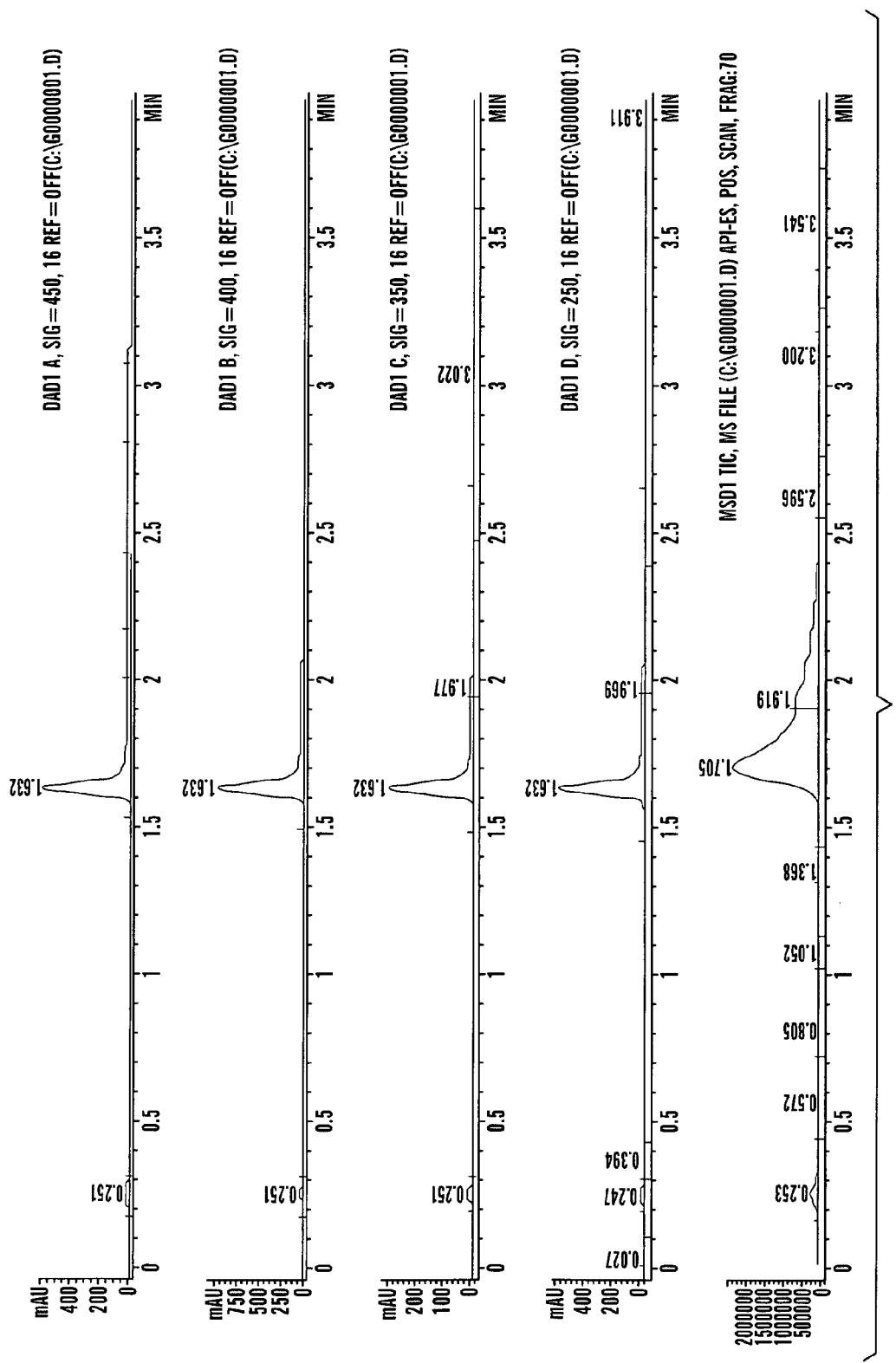

Resin 2 (10 mg) was suspended in 5% trifluoroacetic acid/dichloromethane cleavage cocktail solution (0.5 mL) and shook for 15 min. The resin was filtered off and washed with dichloromethane (1 mL) and methanol (1 mL). The solutions were collected and evaporated to dryness to obtain the benzimidazolium dye 3. ESI-MS (m/z) calcd (found): 624.23 (623.9) for [M]+. See FIGS. 26B-C.

Figure 27A:
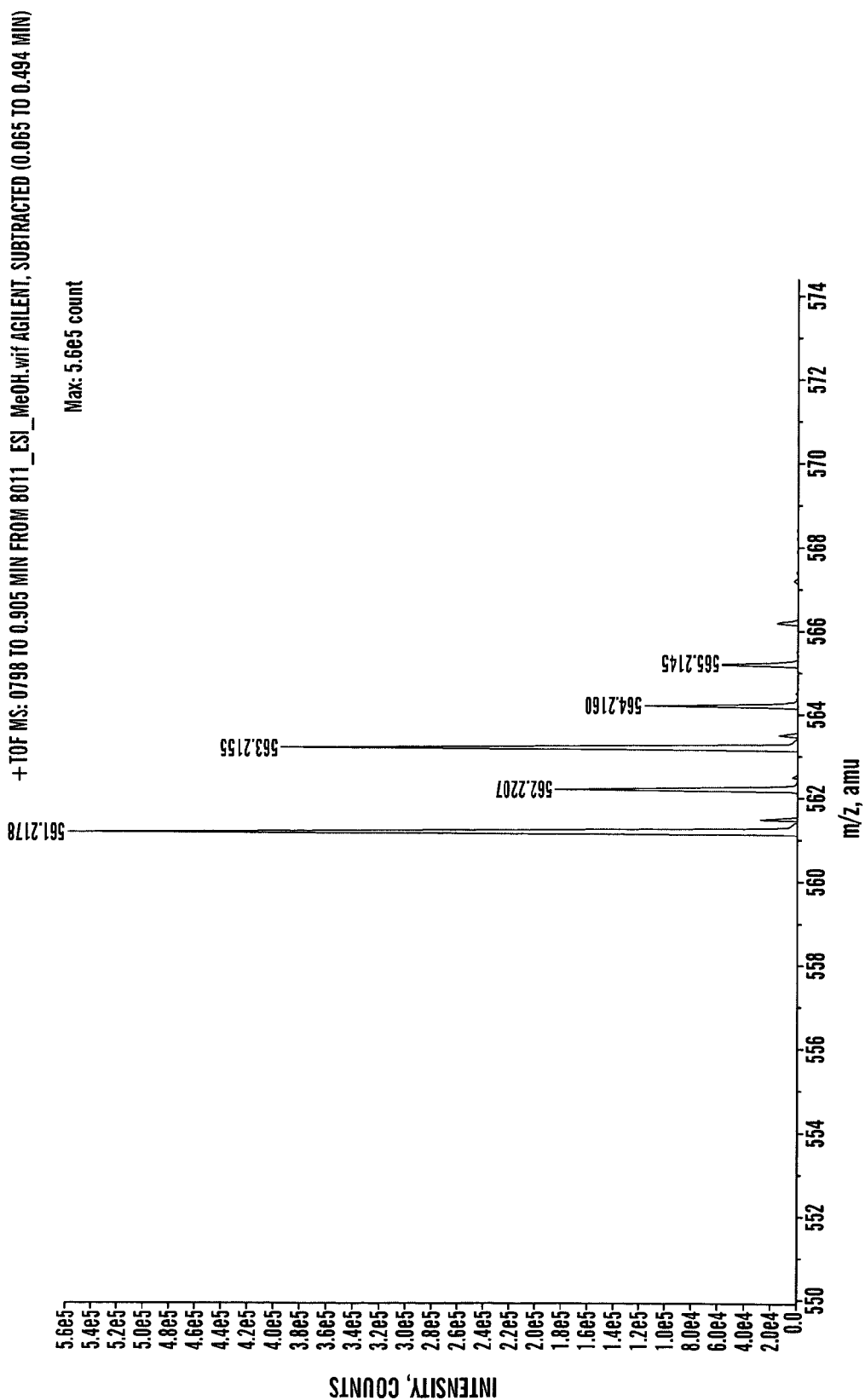
FIGS. 27A-B show (A) the ESI-TOF Mass Spectrum of G26 (Heparin Orange) in MeOH; and (B) the corresponding theoretical calculation.
Figure 27B:
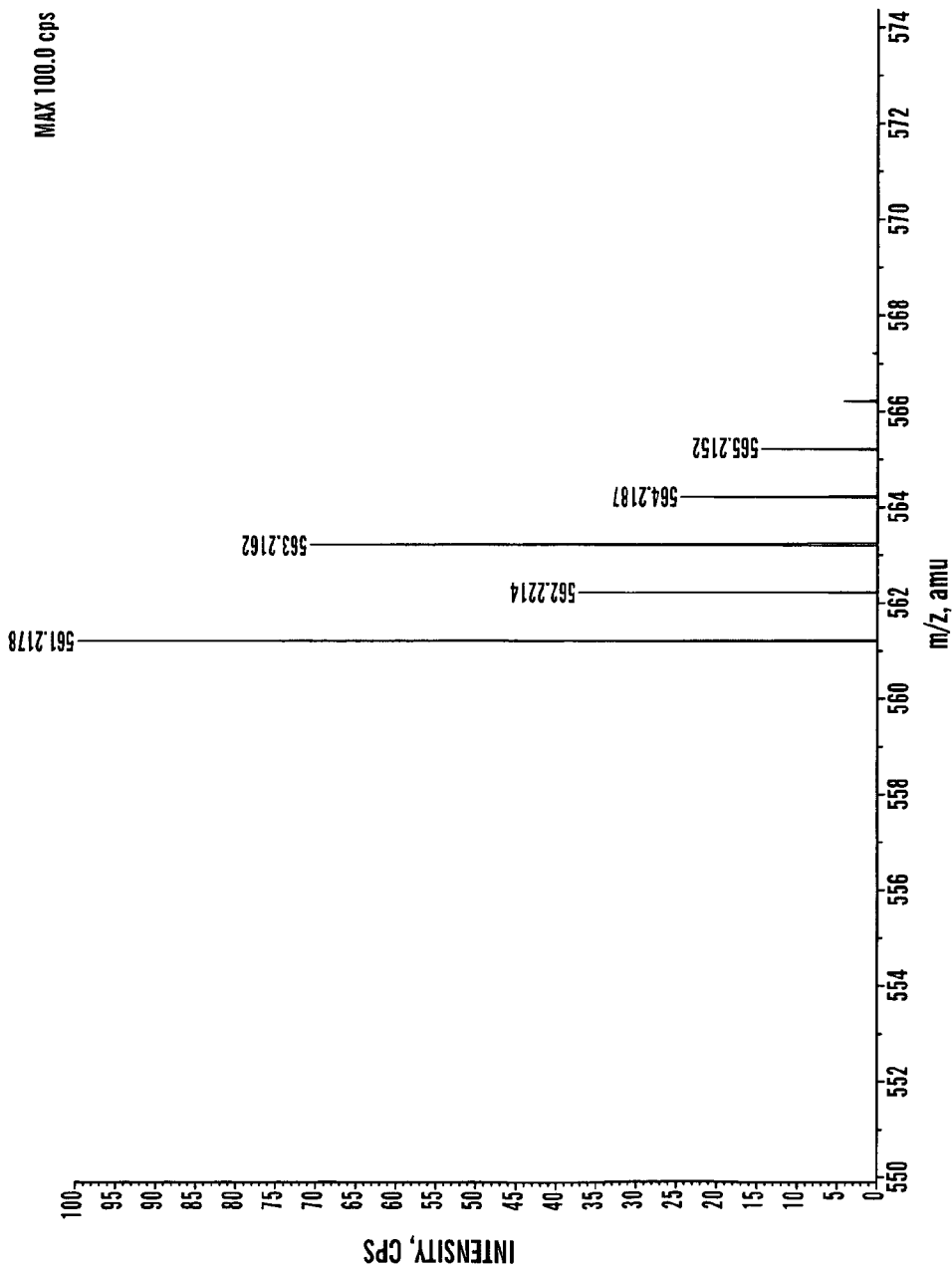
Figure 28:
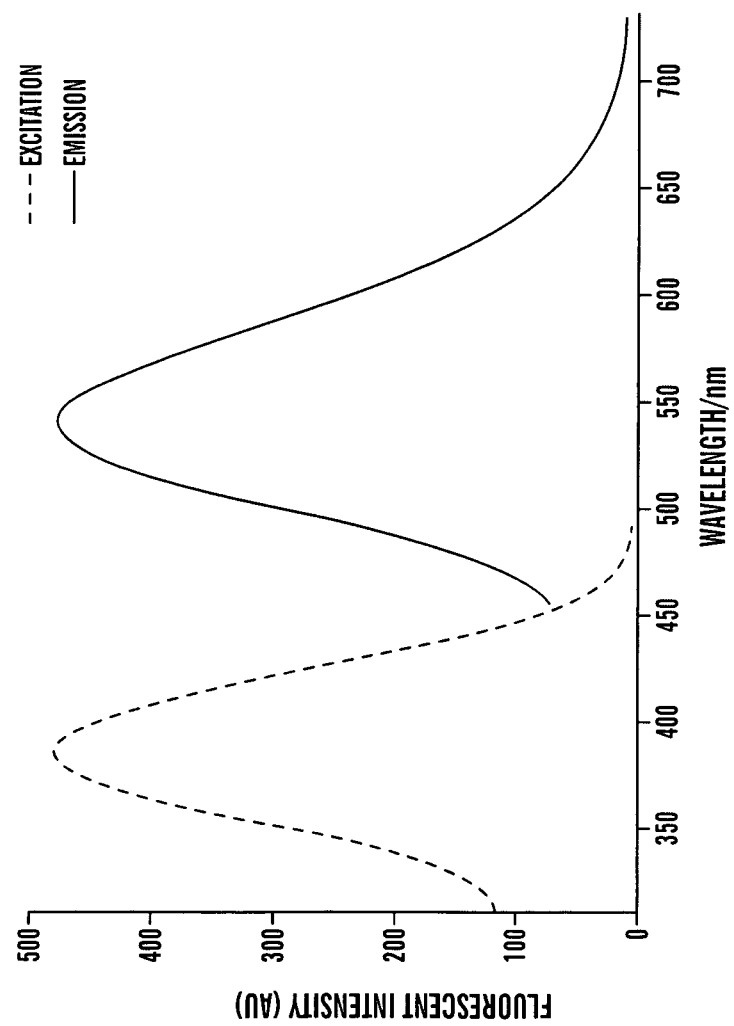
FIG. 28 shows a plot of the fluorescence excitation (emission: 540 nm) and emission (excitation: 390 nm) spectra of 1 mM G26 (Heparin Orange) in methanol (100 μL).
Figure 29:
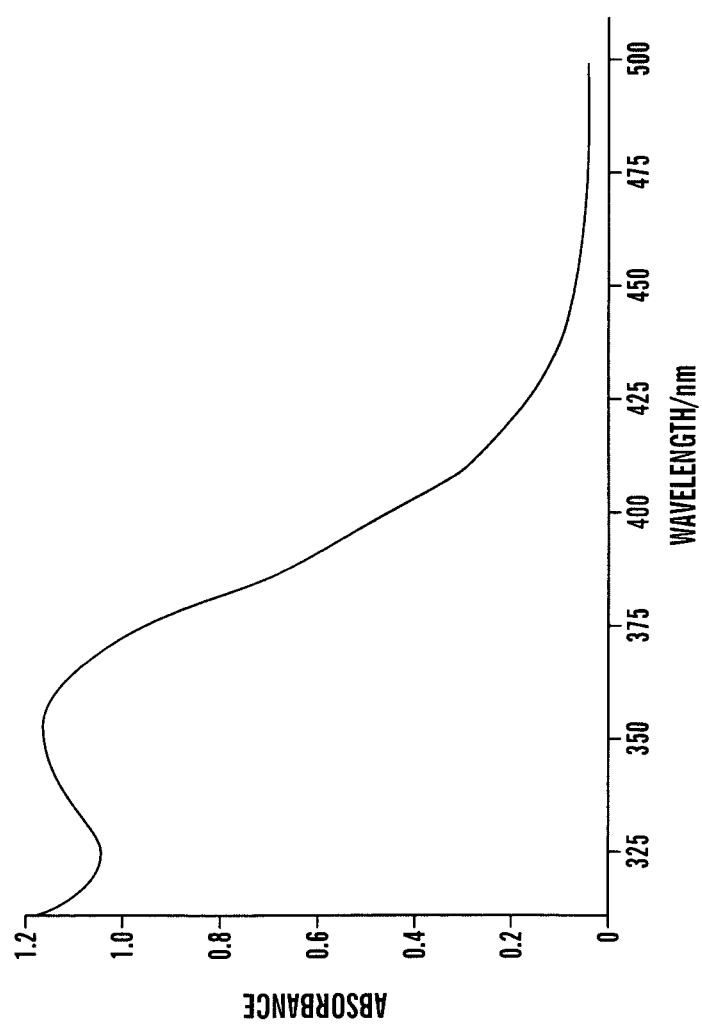
FIG. 29 shows a plot of the UV-Vis absorption spectrum of 1 mM G26 (Heparin Orange) in methanol (100 μL) in a Falcon Microtest flat bottom 96-well polystyrene plate, recorded on a SpectraMax Plus plate reader.
Figure 30A:
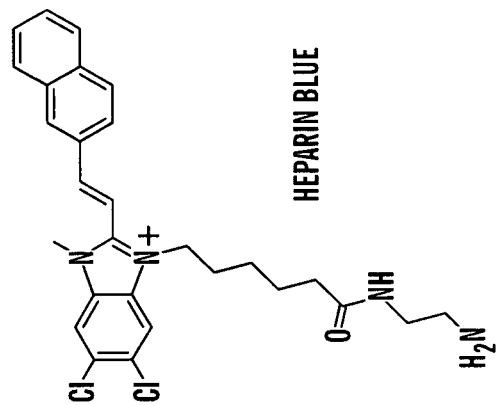
FIGS. 30A-B show (A) structural formula; and (B) LC-MS spectrum of G45(Heparin Blue).
Figure 30B:
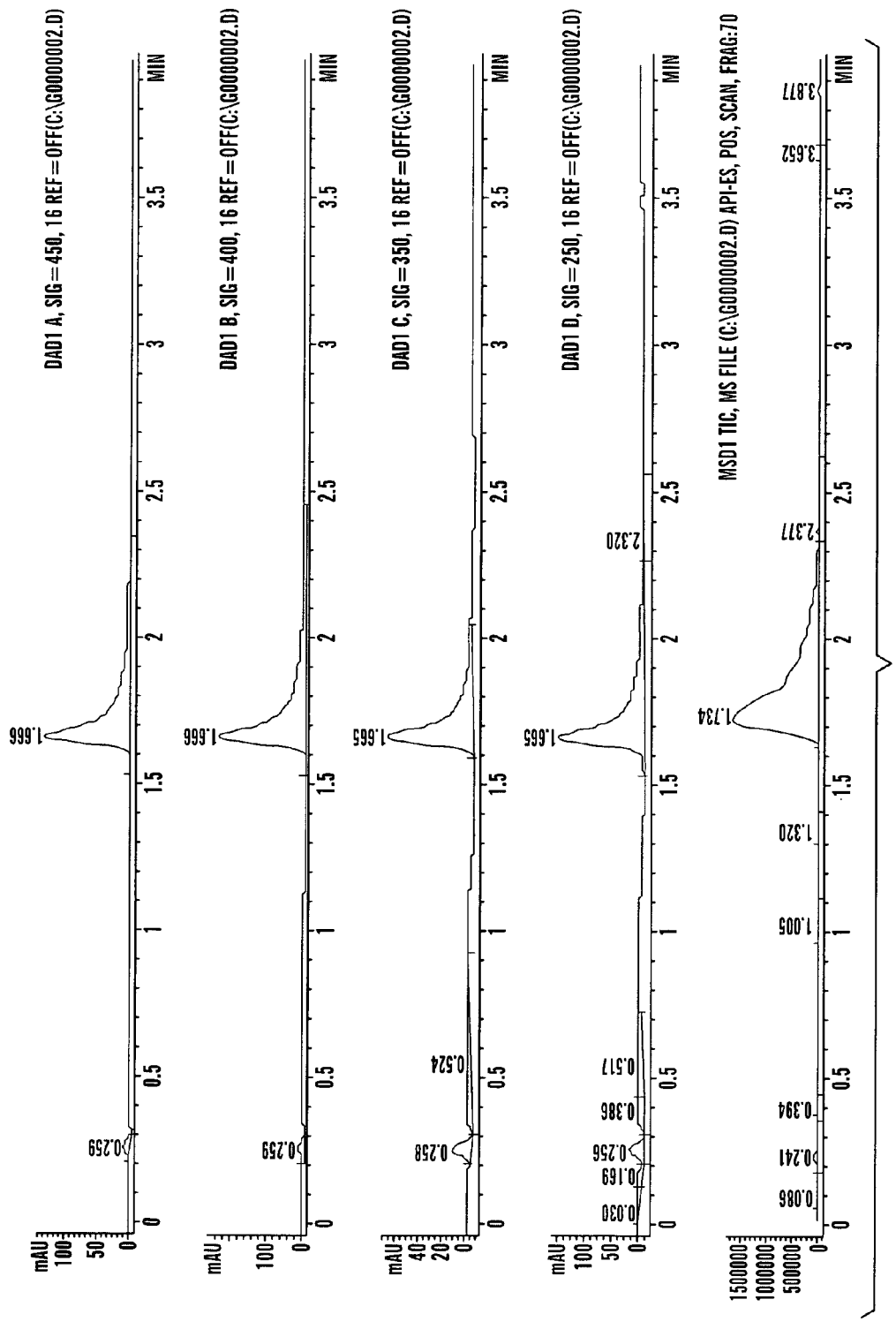
Figure 31A:
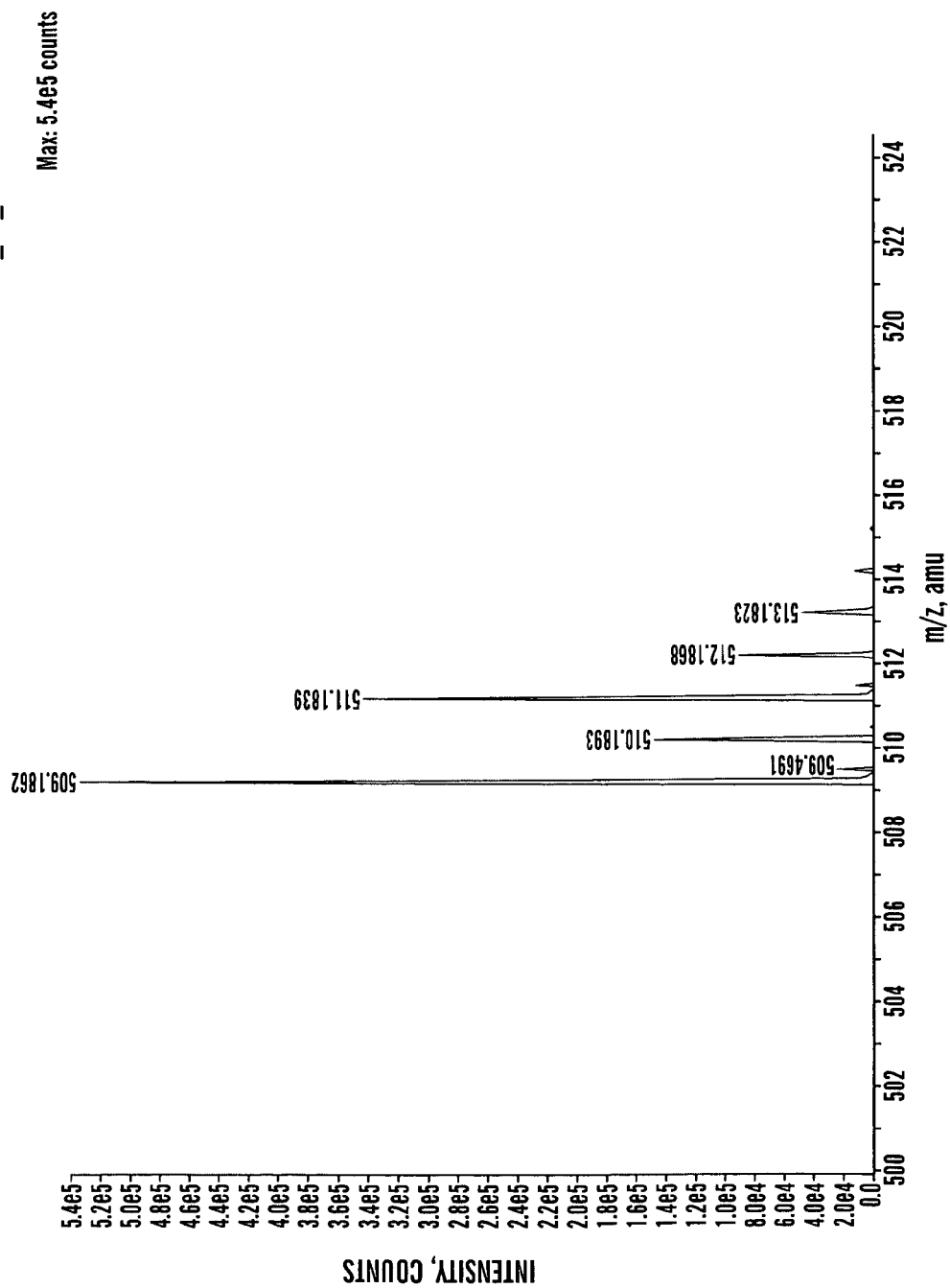
FIGS. 31A-B show (A) the ESI-TOF Mass Spectrum of G45 (Heparin Blue) in MeOH; and (B) the corresponding theoretical calculation.
Figure 31B:
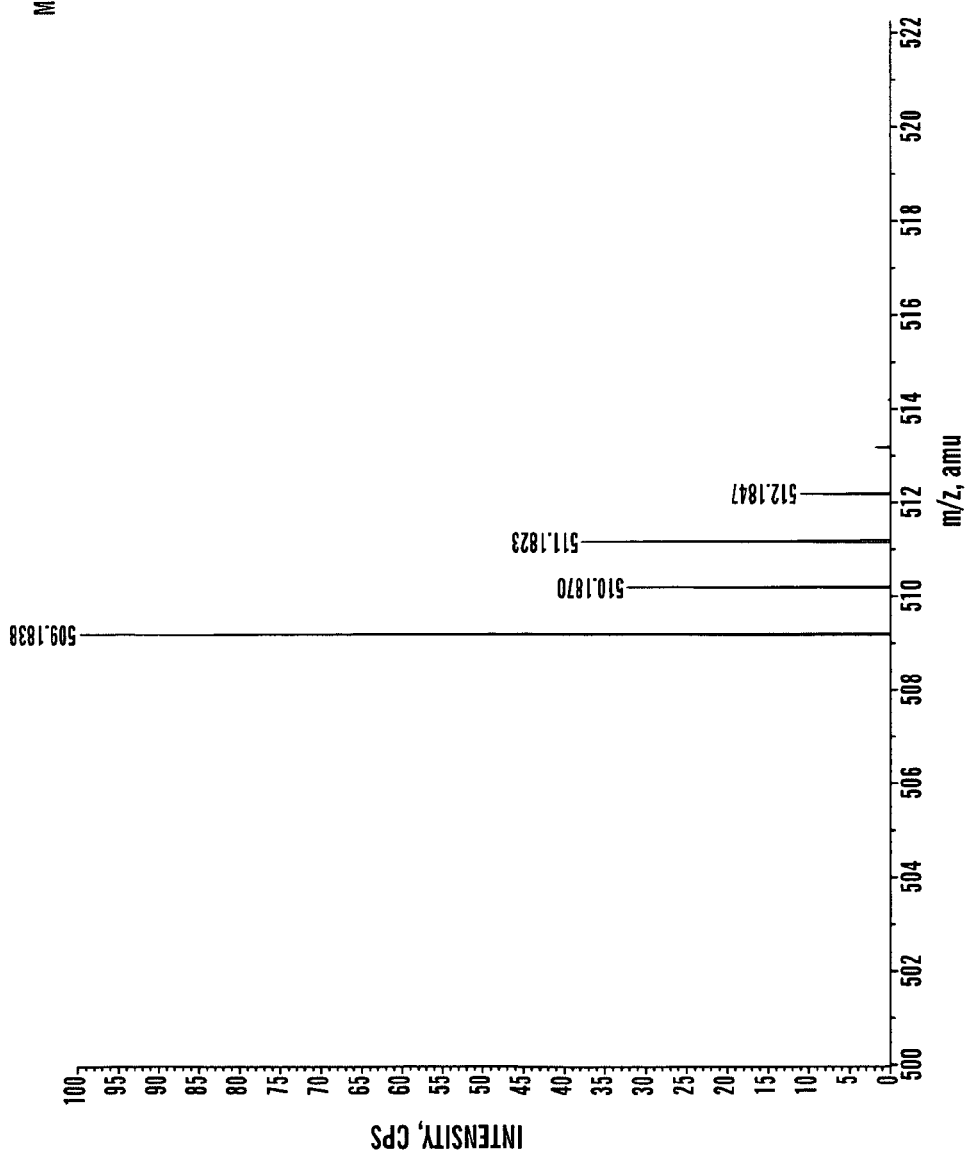
Figure 32:
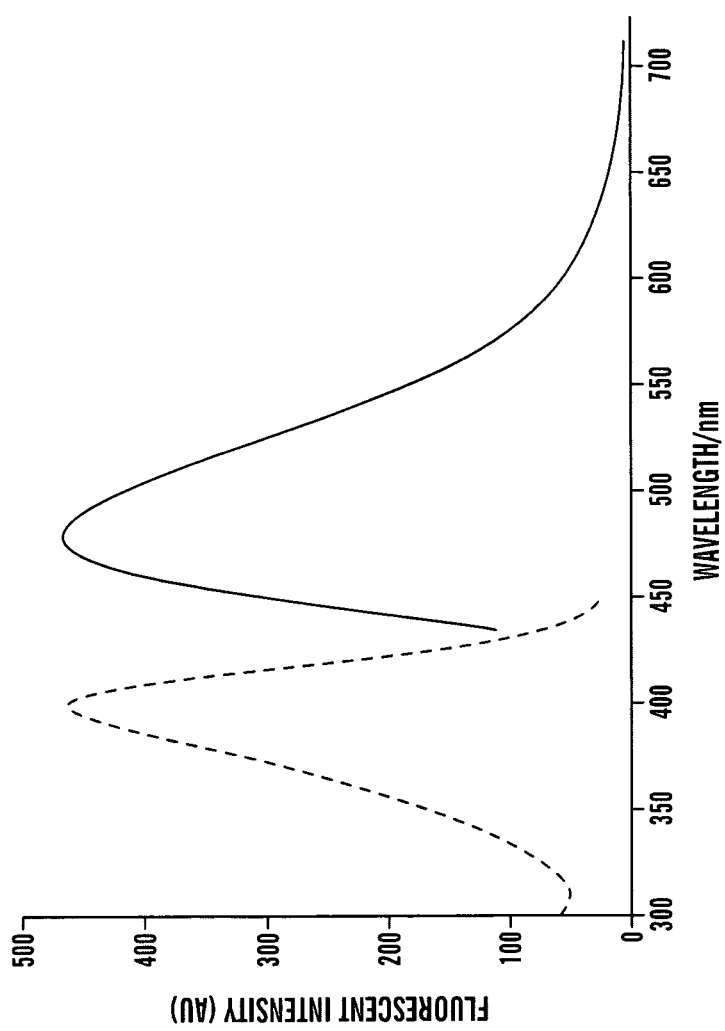
FIG. 32 shows the fluorescence excitation (emission: 477 nm) and emission (excitation: 410 nm) spectra of 1 mM G45 (Heparin Blue) in methanol (100 μL).
Figure 33:
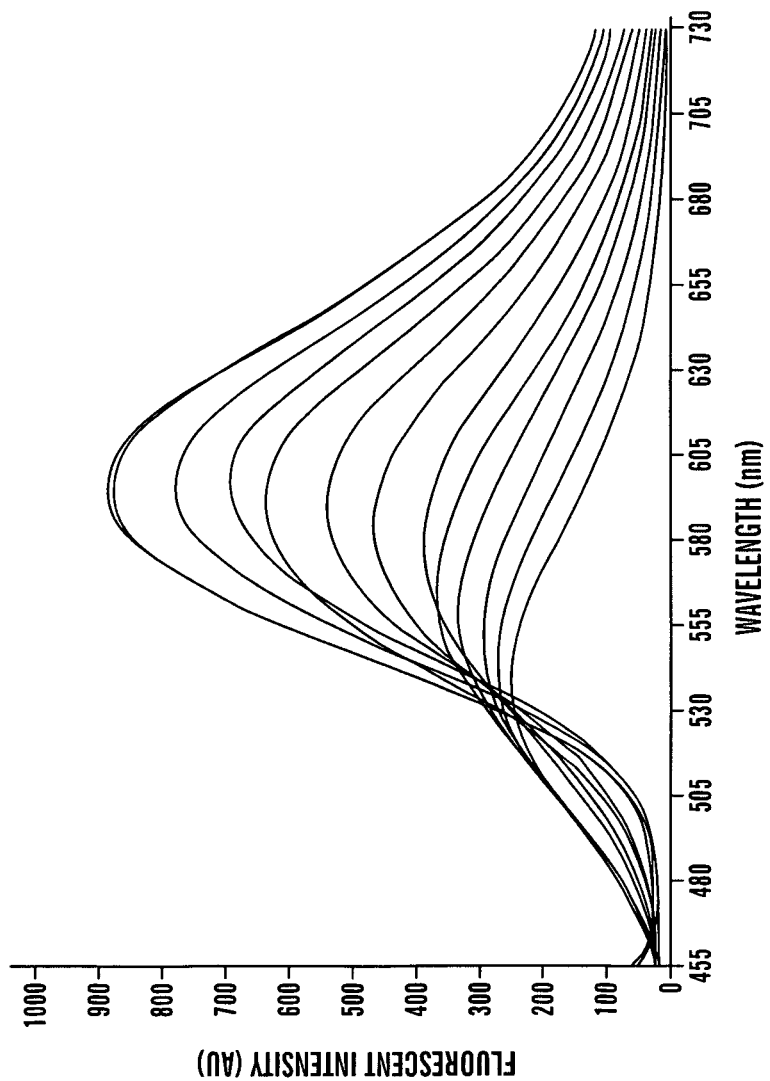
FIG. 33 shows the fluorescence emission spectra (excitation: 380 nm, cutoff: 420 nm) of 10 μM Heparin Orange with 500 μM, 100 μM, 50 μM, 20 μM, 12 μM, 10 μM LMWH and blank control in 10 mM HEPES buffer (pH=7.4) with 1% DMSO.
Figure 34:
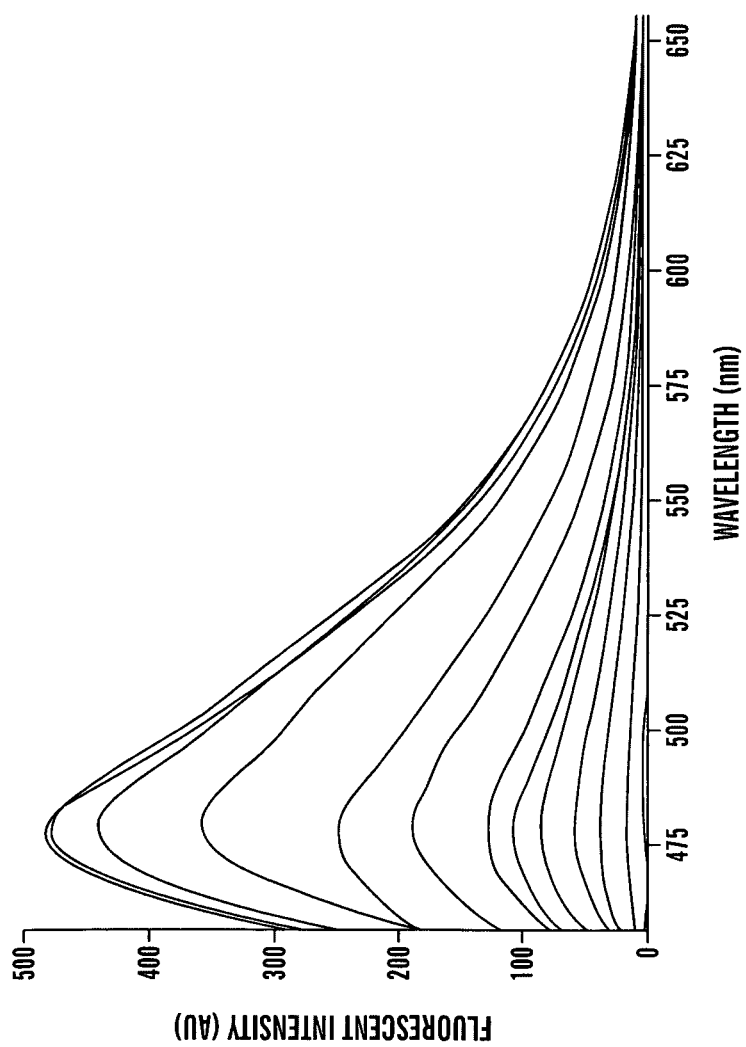
FIG. 34 shows the fluorescence emission spectra (excitation: 420 nm, cutoff: 435 nm) of 10 μM Heparin Blue with 500 M, 100 μM, 50 μM, 20 μM, 12 μM, 10 μM LMWH and blank control in 10 mM HEPES buffer (pH=7.4) with 1% DMSO.
Figure 35A:
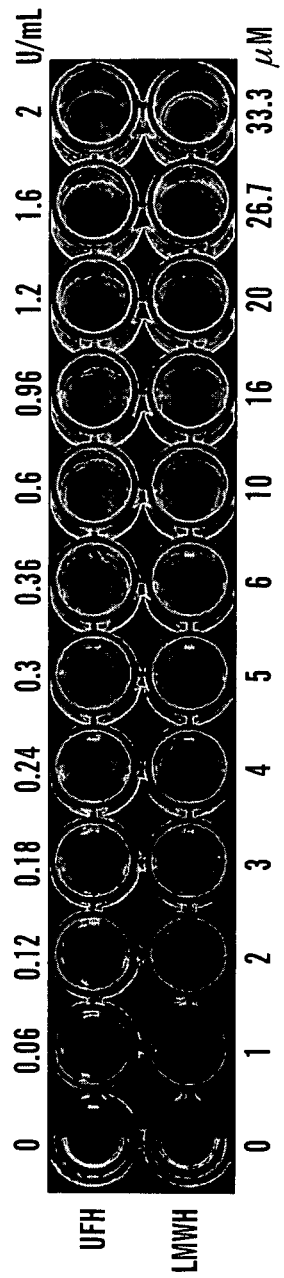
FIGS. 35A-B show photos of (A) Heparin Orange and (B) Heparin Blue with different concentrations of UFH and LMWH in human plasma.
Figure 35B:
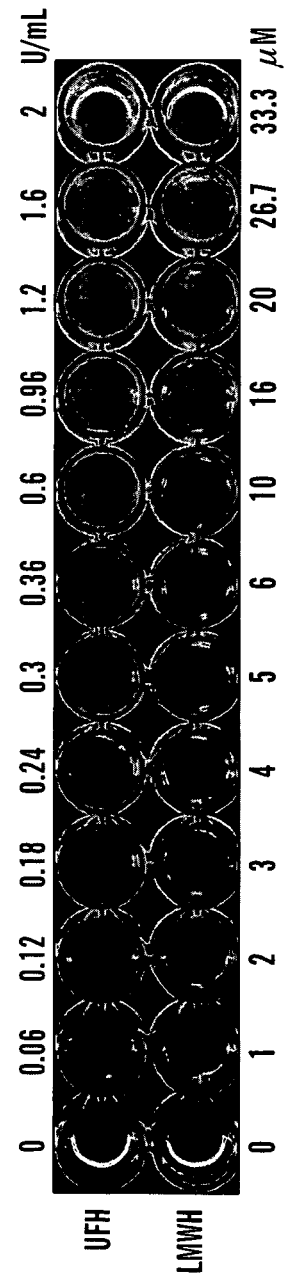

Fluorescence emission spectra (excitation: 470 nm, cutoff: 495 nm) of 1 µM GTP Green Analog 2 with 100 µM GTP, ATP, adenosine, AMP, ADP, uridine, UMP, UDP, UTP, cytosine, CMP, CDP, CTP, guanosine, GMP, GDP and blank control in 10 mM HEPES buffer (pH=7.4) with 1% DMSO. See FIG. 27.

Nucleotide anion detection has long intrigued researchers and witnessed continuous growth. See Li, C., et al., *Angew. Chem. Int. Edit.*, 44: 6371 (2005); Descalzo, A. B., et al., *J. Mater. Chem.*, 15: 2721 (2005); Mizukami, S., et al., *J. Am. Chem. Soc.*, 124: 3920 (2002); Ojida, A., et al., *Tetrahedron Lett.*, 43: 6193 (2002); Sancenon, F., et al., *Helv. Chim. Acta*, 85: 1505 (2002); Thanh, N., et al., *Anal Lett.*, 35: 2499 (2002); Turkewitsch, P., et al., *J. Photochem. Photobiol.*, 117: 199 (1998); Kim, S. K., et al., *Tetrahedron Lett.*, 46: 6617 (2005); Kwon, J. Y., et al., *J. Am. Chem. Soc.*, 126: 8892 (2004); McCleskey, S. C., et al., *J. Am. Chem. Soc.*, 125: 1114 (2003); and Amemiya, S., et al., *Chem. Commun.*, 1027 (1997), which are hereby incorporated by reference in their entirety. Although GTP plays an important role in biological processes, very little work has been done on the development of fluorescent sensors for it. See Kim, S. K., et al., *Tetrahedron Lett.*, 46: 6617 (2005); Kwon, J. Y., et al., *J. Am. Chem. Soc.*, 126: 8892 (2004); McCleskey, S. C., et al., *J. Am. Chem. Soc.*, 125: 1114 (2003); Amemiya, S., et al., *Chem. Commun.*, 1027 (1997); Burma, D. P., *J. Sci. Ind. Res.*, 47: 65 (1988); and Pogson, C. I., *Am. J. Clin. Nutr.*, 27: 380 (1974), which are hereby incorporated by reference in their entirety. Thus far, the best reported GTP sensor, which was designed rationally, showed around 90% quenching response at around mM concentration of GTP, and most of the known GTP sensors compete with ATP to some extent. See Kwon, J. Y., et al., *J. Am. Chem. Soc.*, 126: 8892 (2004), which is hereby incorporated by reference in its entirety. To our knowledge, no turn-on fluorescent sensors for GTP have been reported yet. Embodiments of this invention describe the highly selective fluorescence turn-on GTP sensor, GTP Green, by a diversity directed sensor approach, combined by solid phase combinatorial synthesis of a benzimidazolium library and high-throughput screening.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims that follow.

What is claimed:

1. A compound according to formula (I)

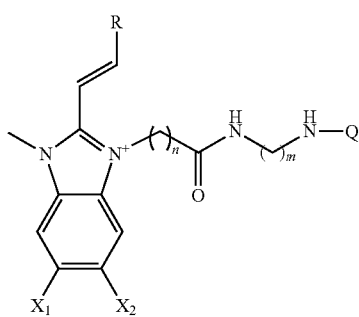

(I)

wherein,
n is an integer from 2-10,
m is an integer from 2-10,
$X_1$ and $X_2$ are independently a halogen,
Q is H or a resin, and
R is (aromatic)$_o$-(linker)$_p$-with the linker being saturated or unsaturated C1-C5 hydrocarbons, each aromatic independently being a substituted or unsubstituted aromatic or heteroaromatic, o being 1 or 2, and p being 0 or 1; and a counterion.

2. The compound according to claim 1, wherein the halogen is F, Cl, Br, or I.

3. The compound according to claim 1, wherein n is 3-8.

4. The compound according to claim 3, wherein n is 5.

5. The compound according to claim 1, wherein m is 2-5.

6. The compound according to claim 5, wherein m is 2.

7. The compound according to claim 1, wherein Q is H.

8. The compound according to claim 1, wherein p is 0.

9. The compound according to claim 1, wherein the aromatic in R is a heteroaromatic ring.

10. The compound according to claim 9, wherein the heteroaromatic ring includes an N, S, or O hetero atom.

11. The compound according to claim 9, wherein the heteroaromatic ring is substituted.

12. The compound according to claim 11, wherein the substituent comprises one or more of hydroxy, saturated or monounsaturated hydrocarbon, (halo)alkoxy, haloalkyl, dihaloalkyl, trihaloalkyl, amine, alkylamine, dialkylamine, nitro, halo, or cyano groups.

13. The compound according to claim 9, wherein the heteroaromatic ring is a multi-ring or fused ring.

14. The compound according to claim 1, wherein the aromatic in R is an aromatic ring which does not include a hetero atom.

15. The compound according to claim 14, wherein the aromatic ring is substituted.

16. The compound according to claim 15, wherein the substituent comprises one or more of hydroxy, saturated or monounsaturated hydrocarbon, (halo)alkoxy, haloalkyl, dihaloalkyl, trihaloalkyl, amine, alkylamine, dialkylamine, nitro, halo, or cyano groups.

17. The compound according to claim 14, wherein the aromatic ring is a multi-ring or fused ring.

18. The compound according claim 1, wherein R is selected from the group consisting of

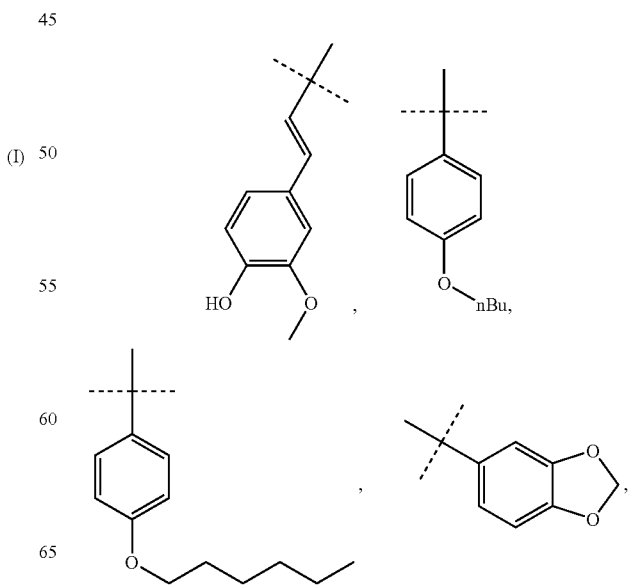

-continued
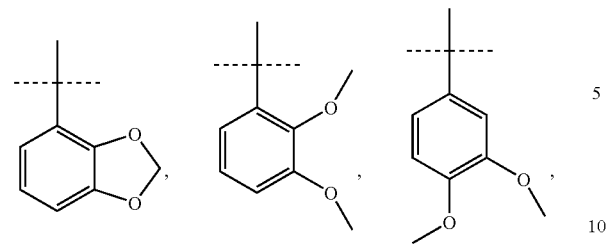
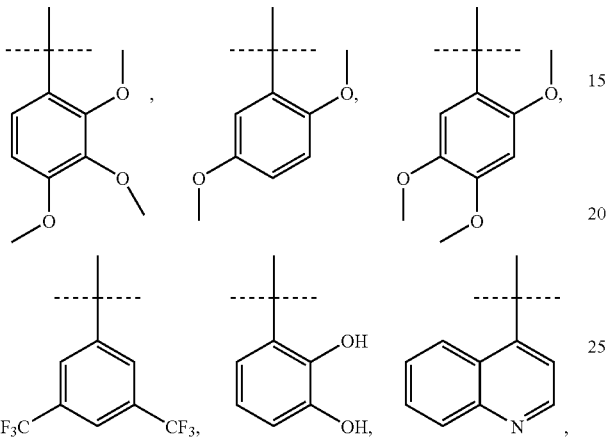
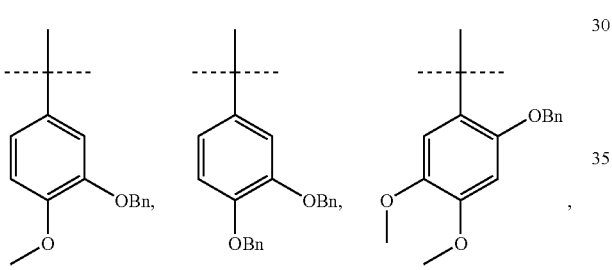
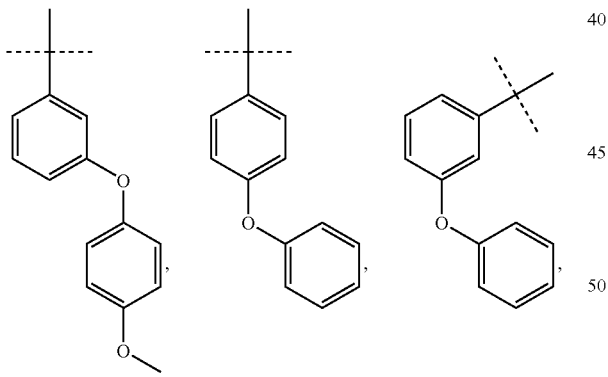
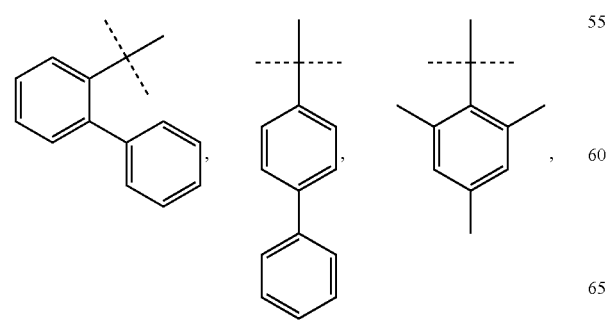
-continued
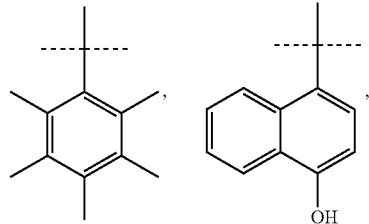
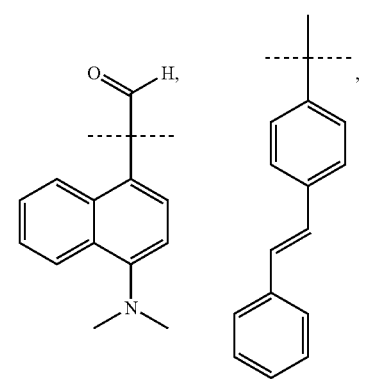
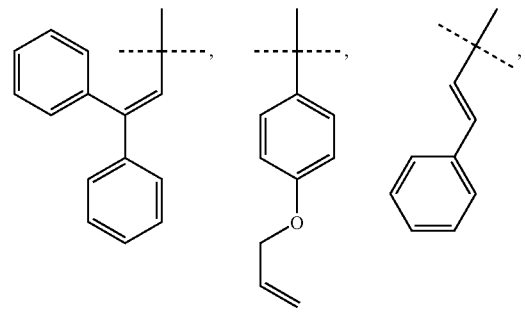
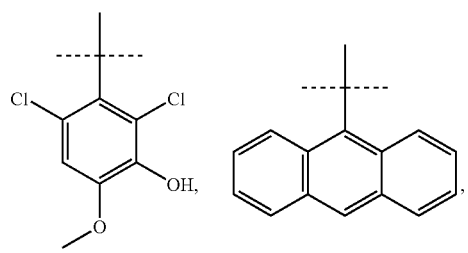
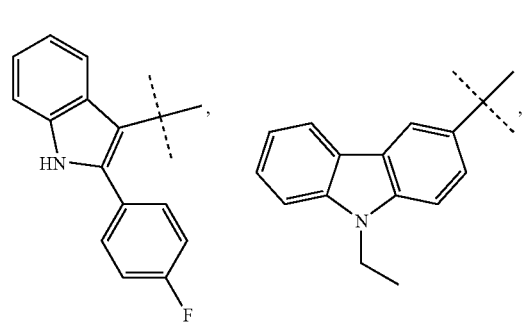

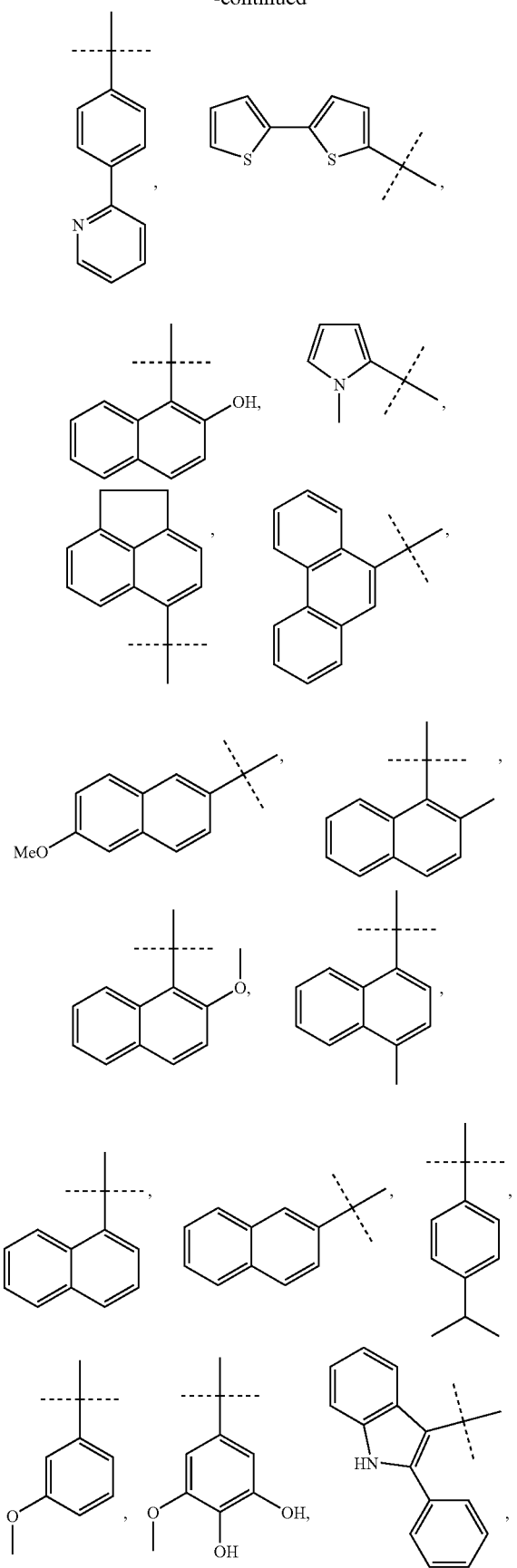
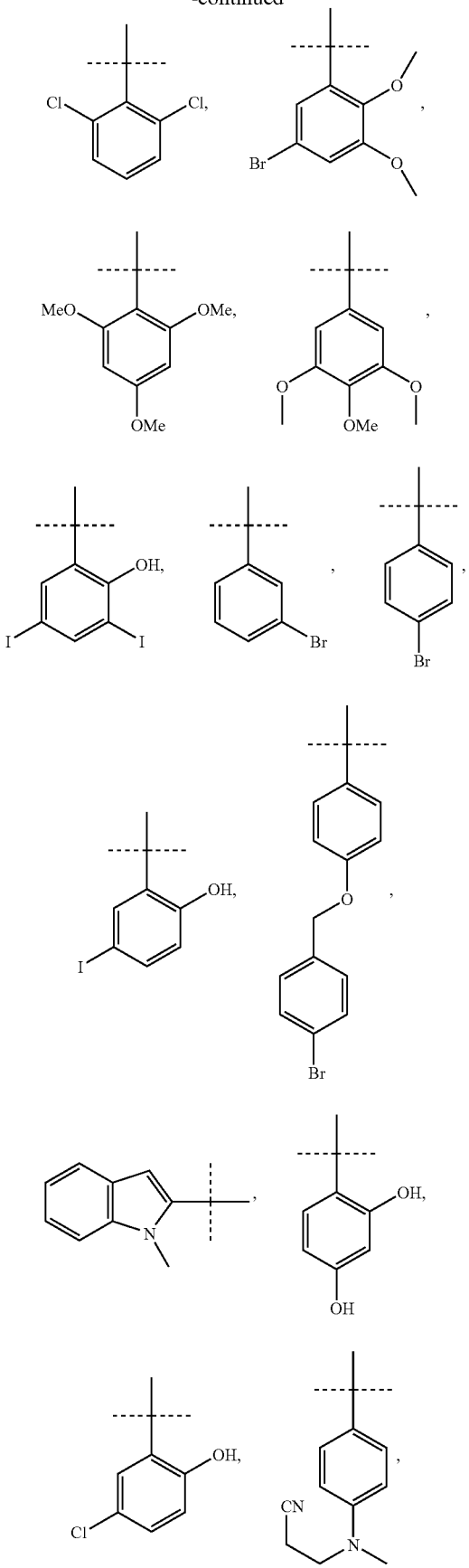

-continued
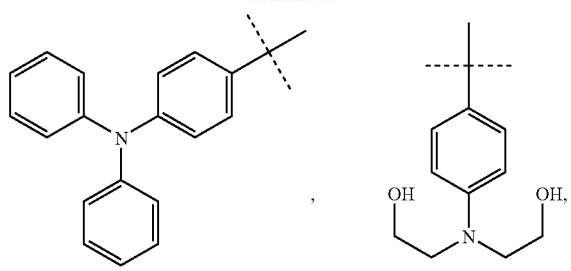
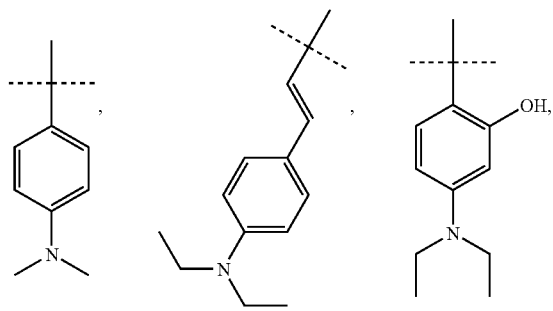
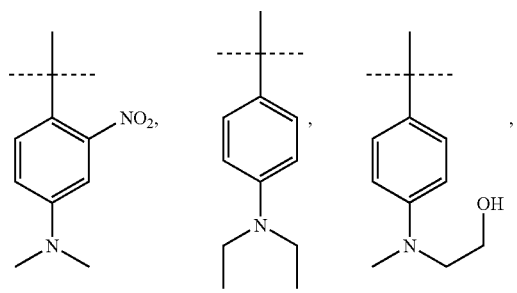
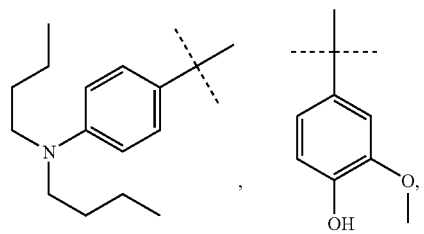
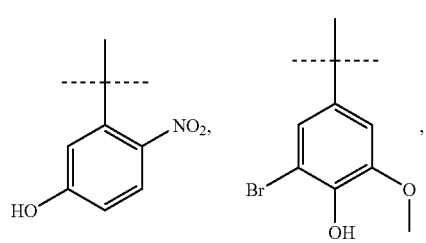
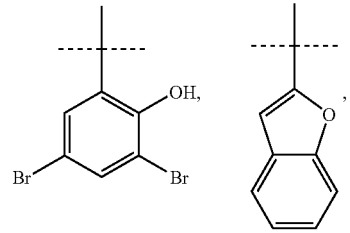
-continued
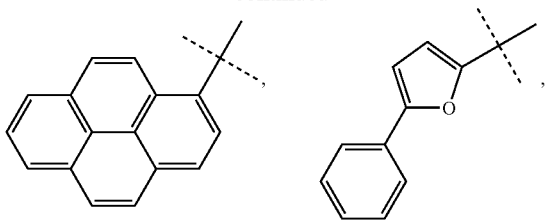
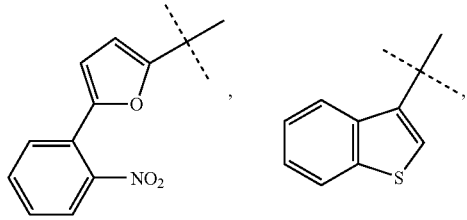
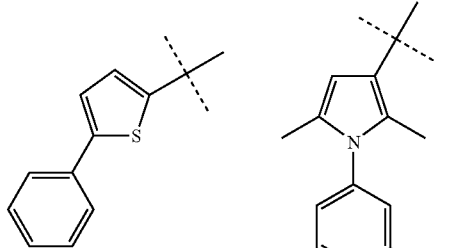
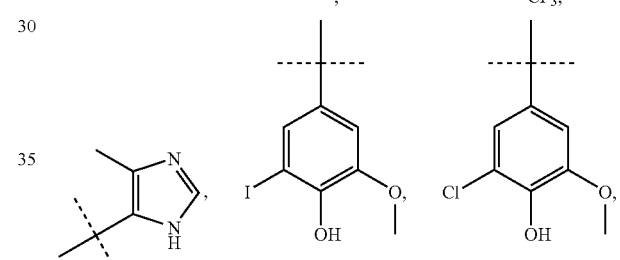
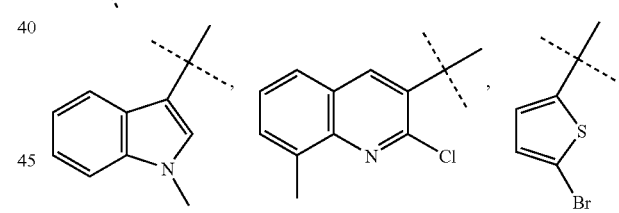
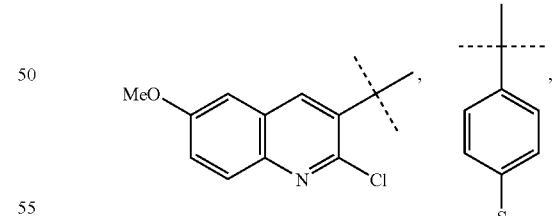
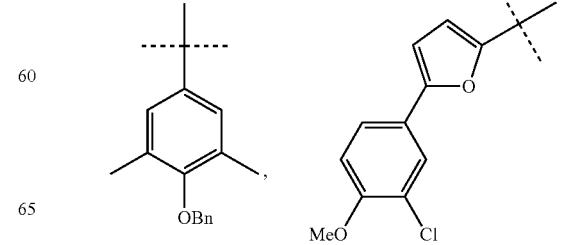

-continued

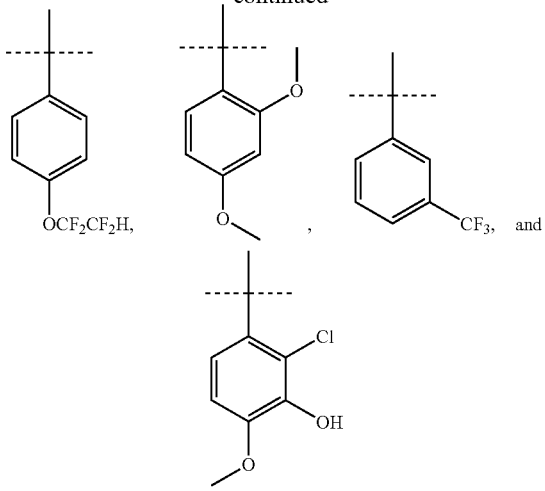

and the bond with the crossing dashed line illustrates the bond formed joining R to the molecule of formula (I).

19. The compound according to claim 1, wherein R is

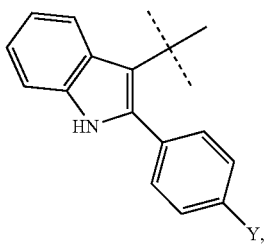

Y is H or halogen, and the bond with the crossing dashed line illustrates the bond formed joining R to the molecule of formula (I).

20. The compound according to claim 19, wherein Y is a halogen selected from the group consisting of F, Cl, Br, and I.

21. The compound according to claim 1, wherein R is

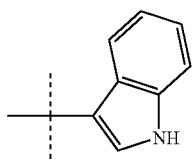

and the bond with the crossing dashed line illustrates the bond formed joining R to the molecule of formula (I).

22. The compound according to claim 1, wherein R is

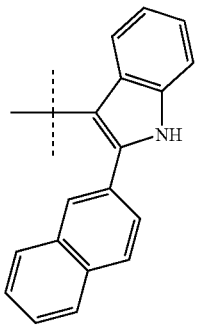

and the bond with the crossing dashed line illustrates the bond formed joining R to the molecule of formula (I).

23. The compound according to claim 1, wherein R is

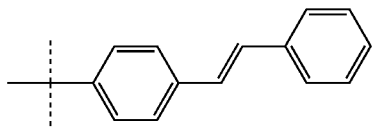

and the bond with the crossing dashed line illustrates the bond formed joining R to the molecule of formula (I).

24. The compound according to claim 1, wherein R is

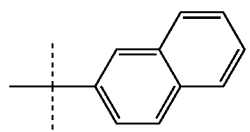

and the bond with the crossing dashed line illustrates the bond formed joining R to the molecule of formula (I).

25. A method of detecting the presence of GTP in a sample, said method comprising:
 introducing a compound according to claim 1 into a sample, wherein the compound does not fluoresce in the absence of a threshold amount of GTP;
 exposing the sample to light at a wavelength suitable to induce fluorescent emissions by the compound; and
 detecting fluorescent emissions by the compound, wherein fluorescence indicates the presence of the threshold amount of GTP.

26. The method according to claim 25, wherein the R is

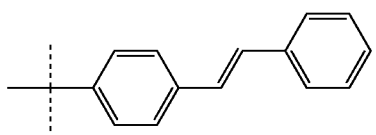

and the bond with the crossing dashed line illustrates the bond formed joining R to the molecule of formula (I).

27. The method according to claim 25, wherein the R is

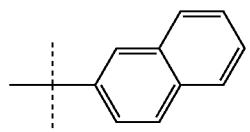

and the bond with the crossing dashed line illustrates the bond formed joining R to the molecule of formula (I).

28. The method according to claim 25, wherein the threshold amount is about $2 \times 10^{-5}$ M GTP.

29. The method according to claim 28, wherein the compound produces substantially no fluorescent emissions in the presence of adenosine, uridine, cytosine, guanosine, AMP, ADP, ATP, UMP, UDP, UTP, CMP, CDP, CTP, GMP, or GDP.

30. The method according to claim 25, wherein the sample comprises a cell extract.

31. The method according to claim 25, wherein the sample comprises whole cells.

32. The method according to claim 25, wherein the whole cells are present in an ex vivo tissue sample.

33. The method according to claim 25, wherein the whole cells are present in an in vitro cell sample.

34. A method of detecting the presence of heparin in a sample comprising:
introducing a compound according to claim 1 into a sample, wherein the compound does not fluoresce in the absence of a threshold amount of heparin;
exposing the sample to light at a wavelength suitable to induce fluorescent emissions by the compound; and
detecting fluorescent emissions by the compound, wherein fluorescence indicates the presence of heparin.

35. The method of claim 34, wherein said fluorescence indicates the presence of the threshold amount of heparin.

36. The method of claim 35, wherein the threshold amount is about 0.1 μM.

37. The method of claim 34, wherein said detecting is quantitative.

38. The method of claim 34, wherein the sample comprises blood plasma.

39. The method of claim 34, wherein the heparin is unfractionated heparin.

40. The method of claim 34, wherein the heparin is low molecular weight heparin.

41. The method of claim 34, wherein R is

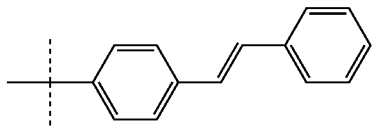

and the bond with the crossing dashed line illustrates the bond formed joining R to the molecule of formula (I).

42. The method of claim 34, wherein R is

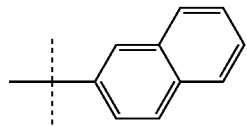

and the bond with the crossing dashed line illustrates the bond formed joining R to the molecule of formula (I).

43. A method of making a compound according to claim 7 said method comprising:
treating the compound of formula (I) having Q=resin under conditions effective to cleave the resin.

44. A method of making a compound of formula (I) according to claim 1, said method comprising:
reacting a compound according to formula (II)

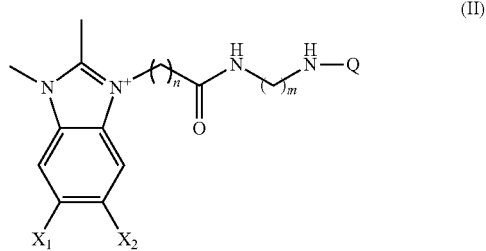

with R—(CO)H under conditions effective to form the compound of formula (I).

45. The method according to claim 44 further comprising:
reacting a resin-bound (aminoalkyl)amine with an intermediate carboxylic acid according to formula (III)

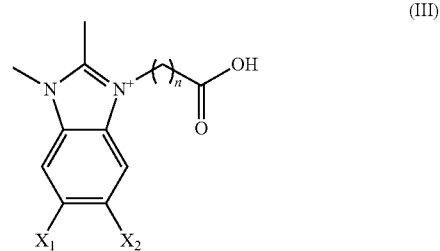

under conditions effective to form the compound according to formula (II).

46. The method according to claim 45 further comprising:
reacting ethyl 6-(trifluoromethylsulfonyloxy)alkanoate with 5,6-dihalo-1,2-dimethyl-benzoimidazole under conditions effective to form the compound according to formula (III).

* * * * *

UNITED STATES PATENT AND TRADEMARK OFFICE
CERTIFICATE OF CORRECTION

PATENT NO. : 8,716,491 B2
APPLICATION NO. : 11/779630
DATED : May 6, 2014
INVENTOR(S) : Young-Tae Chang and Shenliang Wang Page 1 of 1

It is certified that error appears in the above-identified patent and that said Letters Patent is hereby corrected as shown below:

In the Specification

Column 1, Lines 6-12, delete "The subject matter of this application was made with support from the United States Government under National Institute of Health, Grant No. P20GM072029. Components of this work were conducted in a Shared Instrumentation Facility constructed with support from Research Facilities Improvement Grant C06 RR-16572 from the NCRR/NIH. The U.S. Government has certain rights." and insert --This invention was made with government support under GM072029 and RR165720 awarded by National Institutes of Health. The government has certain rights in the invention.--

Signed and Sealed this
Twentieth Day of August, 2019

Andrei Iancu
*Director of the United States Patent and Trademark Office*